(12) United States Patent
Mycek et al.

(10) Patent No.: US 8,694,266 B2
(45) Date of Patent: *Apr. 8, 2014

(54) MULTIMODAL SPECTROSCOPIC SYSTEMS AND METHODS FOR CLASSIFYING BIOLOGICAL TISSUE

(75) Inventors: Mary-Ann Mycek, Ann Arbor, MI (US); Malavika Chandra, Lansdale, PA (US); James Scheiman, Sup Twp, MI (US); Robert H. Wilson, Ann Arbor, MI (US); Diane Simeone, Ann Arbor, MI (US); Barbara McKenna, Ann Arbor, MI (US); Jeremy Taylor, Ann Arbor, MI (US); Oliver Lee, Ann Arbor, MI (US); Leng-Chun Chen, Ann Arbor, MI (US); William Lloyd, Wixom, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,471

(22) Filed: May 16, 2012

(65) Prior Publication Data

US 2012/0245473 A1 Sep. 27, 2012

Related U.S. Application Data

(63) Continuation-in-part of application No. 12/882,131, filed on Sep. 14, 2010, now Pat. No. 8,234,078, which is a continuation-in-part of application No. 12/479,600, filed on Jun. 5, 2009, now Pat. No. 8,239,139.

(60) Provisional application No. 61/487,572, filed on May 18, 2011, provisional application No. 61/242,126, filed on Sep. 14, 2009, provisional application No. 61/058,966, filed on Jun. 5, 2008.

(51) Int. Cl.
*G01N 31/00* (2006.01)
*G01N 33/48* (2006.01)
*G06G 7/58* (2006.01)

(52) U.S. Cl.
USPC ................................. 702/27; 702/19; 703/11

(58) Field of Classification Search
None
See application file for complete search history.

(56) References Cited

U.S. PATENT DOCUMENTS

| | | | |
|---|---|---|---|
| 5,601,087 A | 2/1997 | Gunderson et al. | |
| 6,174,291 B1 | 1/2001 | McMahon et al. | |
| 6,571,118 B1* | 5/2003 | Utzinger et al. | 600/476 |
| 7,231,243 B2* | 6/2007 | Tearney et al. | 600/407 |

OTHER PUBLICATIONS

Volynskaya et al., "Diagnosing breast cancer using diffuse reflectance spectroscopy and intrinsic fluorescence spectroscopy", Journal of Biomedical Optics, Mar./Apr. 2008, pp. 024012-1 to 9, vol. 13(2).

Chandra et al., "Pancreatic tissue assessment using fluorescence and reflectance spectroscopy", Proc. of SPIEOSA Biomedical Optics, 2007, pp. 66281R-1 to 8, SPIE vol. 6628.

Wilson et al., "Photon-tissue interaction model enables quantitative optical analysis of human pancreatic tissues", Optical Society of America, 2010.

Koninger et al., "Overexpressed Decorin in Pancreatic Cancer: Potential Tumor Growth Inhibition and Attenuation of Chemotherapeutic Action", Clin. Cancer Res., Jul. 15, 2004, pp. 4776-4783, vol. 10.

Hruban et al., "An Illustrated Consensus on the Classification of Pancreatic Intraepithelial Neoplasia and Intraductal Papillary Mucinous Neoplasms," Am. J. Surg. Pathol., Aug. 2004, pp. 977-987, vol. 28, No. 8.

Wilson et al., "Optical spectroscopy detects histological hallmarks of pancreatic cancer", Manuscript submitted to Optics Express, Apr. 27, 2009.

Saidi et al., "Mie and Rayleigh modeling of visible-light scattering in neonatal skin", Applied Optics, Nov. 1, 1995, pp. 7410-7418, vol. 34, No. 31.

Van Veen et al., "Diffuse-reflectance spectroscopy from 500 to 1060 nm by correction for inhomogeneously distributed absorbers", Optics Letters, Feb. 15, 2002, pp. 246-248, vol. 27, No. 4.

Chandra et al., "Probing pancreatic disease using tissue optical spectroscopy", Journal of Biomedical Optics, Nov./Dec. 2007, pp. 060501-1 to 3, vol. 12(6).

Vishwanath et al., "Do fluorescence decays remitted from tissues accurately reflect intrinsic fluorophore lifetimes?", Optics Letters, Jul. 1, 2004, pp. 1512-1514, vol. 29, No. 13.

Zonios et al., "Comparative evaluation of two simple diffuse reflectance models for biological tissue applications", Applied Optics, Sep. 20, 2008, pp. 4965-4973, vol. 47, No. 27.

Reif et al., "Analysis of changes in reflectance measurements on biological tissues subjected to different probe pressures", Journal of Biomedical Optics, Jan./Feb. 2008, pp. 010502-1 to 3, vol. 13(1).

Wang et al., "MCML—Monte Carlo modeling of light transport in multi-layered tissues", Computer Methods and Programs in Biomedicine 47, 1995, pp. 131-146.

Cohen et al., "Pancreatic Adenocarcinoma: Regression Analysis to Identify Improved Cytologic Criteria", Diagnostic Cytopathology, 1991, pp. 341-345, vol. 7, No. 4.

Chandra et al., "Quantitative molecular sensing in biological tissues: an approach to non-invasive optical characterization", Optics Express, Jun. 26, 2006, pp. 6157-6171, vol. 14, No. 13.

Hillemanns et al., Lymph node metastasis detection of ovarian cancer by porphyrin fluorescence photodetection: case report, Lasers Med. Sci., 2007, pp. 131-135, vol. 22.

Finlay et al., "Hemoglobin oxygen saturations in phantoms and in vivo from measurements of steady-state diffuse reflectance at a single, short source-detector separation", Medical Physics, Jul. 2004, pp. 1949-1959, vol. 31, No. 7.

(Continued)

*Primary Examiner* — Eric S DeJong
(74) *Attorney, Agent, or Firm* — Howard & Howard Attorneys PLLC

(57) ABSTRACT

Multimodal optical spectroscopy systems and methods produce a spectroscopic event to obtain spectroscopic response data from biological tissue, either ex vivo or in vivo, and compare the response data with a model configured to correlate the measured response data and the most probable attributes of the tissue, thus facilitating classification of the tissue based on those attributes.

13 Claims, 37 Drawing Sheets

(56) References Cited

OTHER PUBLICATIONS

Perelman et al., "Observation of Periodic Fine Structure in Reflectance from Biological Tissue: A New Technique for Measuring Nuclear Size Distribution", Physical Review Letters, Jan. 19, 1998, pp. 627-630, vol. 80, No. 3.

Sears et al., "Image Cytometry as a Discriminatory Tool for Cytologic Specimens Obtained by Endoscopic Retrograde Cholangiopancreatography", Cancer Cytopathology, Apr. 25, 1998, pp. 119-126, vol. 84, No. 2.

Palmer et al., "Monte-Carlo-based model for the extraction of intrinsic fluorescence from turbid media", Journal of Biomedical Optics, Mar./Apr. 2008, pp. 024017-1 to 9, vol. 13(2).

Imamura et al., "Quantitative Analysis of Collagen and Collagen Subtypes I, III, and V in Human Pancreatic Cancer, Tumor-Associated Chronic Pancreatitis, and Alcoholic Chronic Pancreatitis", Pancreas, 1995, pp. 357-364, vol. 11, No. 4.

Chandra et al., "Spectral areas and ratios classifier algorithm for pancreatic tissue classification using optical spectroscopy", Journal of Biomedical Optics, Jan./Feb. 2010, pp. 010514-1 to 3, vol. 15(1).

Fox et al., "Formaldehyde Fixation", The Journal of Histochemistry & Cytochemistry, 1985, pp. 845-853, vol. 33, No. 8.

Vishwanath et al., "Time-resolved photon migration in bi-layered tissue models", Optics Express, Sep. 19, 2005, pp. 7466-7482, vol. 13, No. 19.

Joshi et al., "Improving PET receptor binding estimates from Logan plots using principal component analysis", Journal of Cerebral Blood Flow & Metabolism, 2008, pp. 852-865, vol. 28.

Sefkow et al., "Method for Measuring Cellular Optical Absorption and Scattering Evaluated Using Dilute Cell Suspension Phantoms", Applied Spectroscopy, 2001, vol. 55, No. 11.

Zonios et al., "Diffuse reflectance spectroscopy of human adenomatous colon polyps in vivo", Applied Optics, Nov. 1, 1999, pp. 6628-6637, vol. 38, No. 31.

Ge et al., "Identification of Colonic Dysplasi and Neoplasia by Diffuse Reflectance Spectroscopy and Pattern Recognition Techniques", Applied Spectroscopy, 1998, pp. 833-839, vol. 52, No. 6.

Lin et al., "Cytologic Criteria for Well Differentiated Adenocarcinoma of the Pancreas in Fine-Needle Aspiration Biopsy Specimens", Cancer Cytopathology, Feb. 25, 2003, pp. 44-50, vol. 99, No. 1.

Muller et al., "Intrinsic fluorescence spectroscopy in turbid media: disentangling effects of scattering and absorption", Applied Optics, Sep. 1, 2001, pp. 4633-4646, vol. 40, No. 25.

Reif et al., "Analytical model of light reflectance for extraction of the optical properties in small volumes of turbid media", Applied Optics, Oct. 10, 2007, pp. 7317-7328, vol. 46, No. 29.

Hruban et al., "Pancreatic Intraepithelial Neoplasia", The American Journal of Surgical Pathology, 2001, pp. 579-586, vol. 25, No. 5.

Backman et al., "Polarized Light Scattering Spectroscopy for Quantitative Measurement of Epithelial Cellular Structures In Situ", IEEE Journal of Selected Topics in Quantum Electronics, Jul./Aug. 1999, pp. 1019-1999, vol. 5, No. 4.

\* cited by examiner

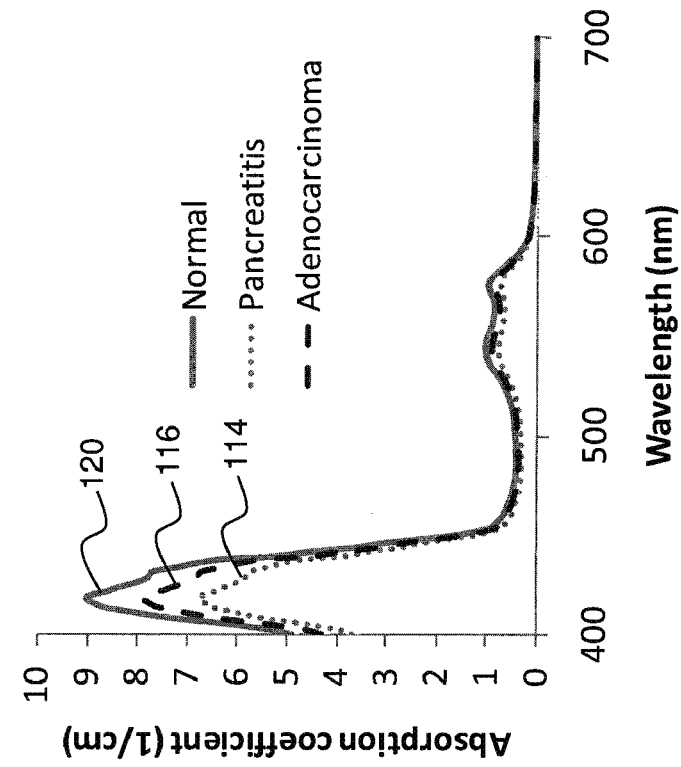
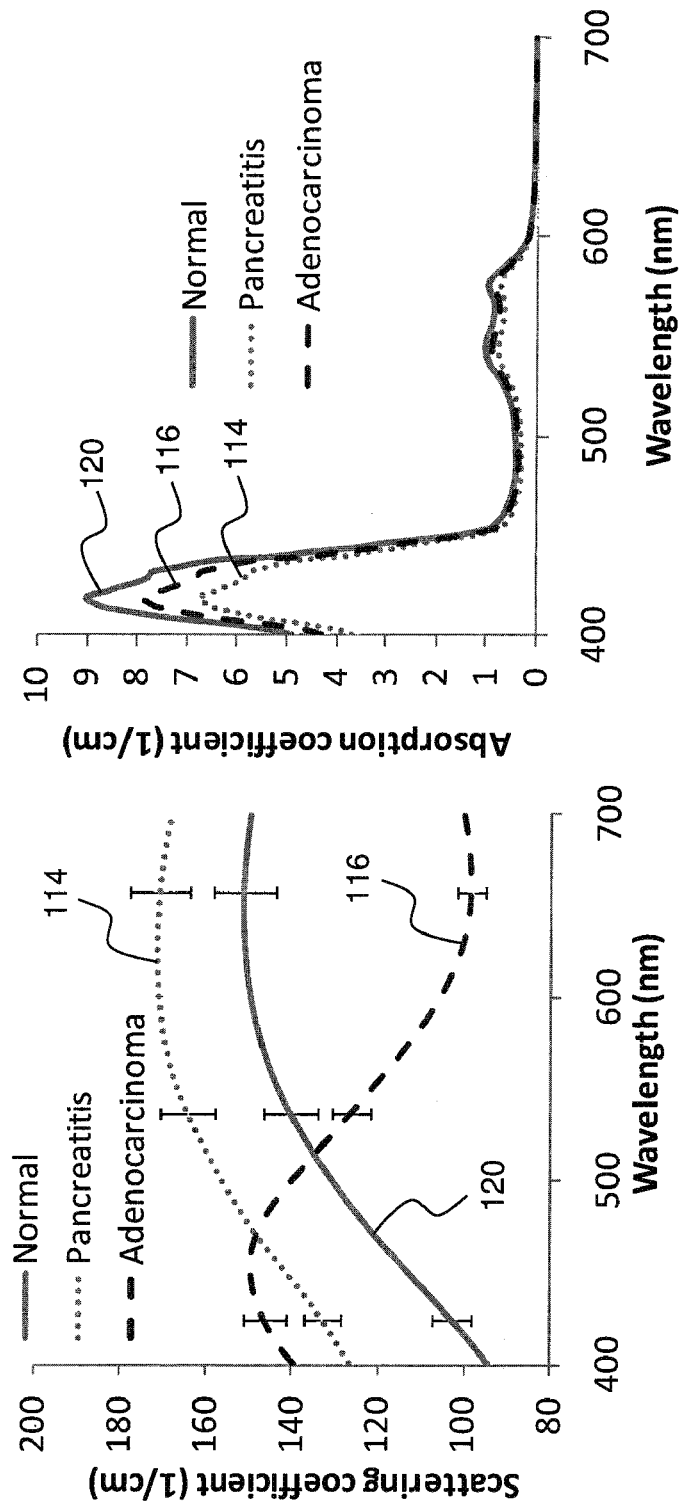
Fig. 2B
Fig. 2A

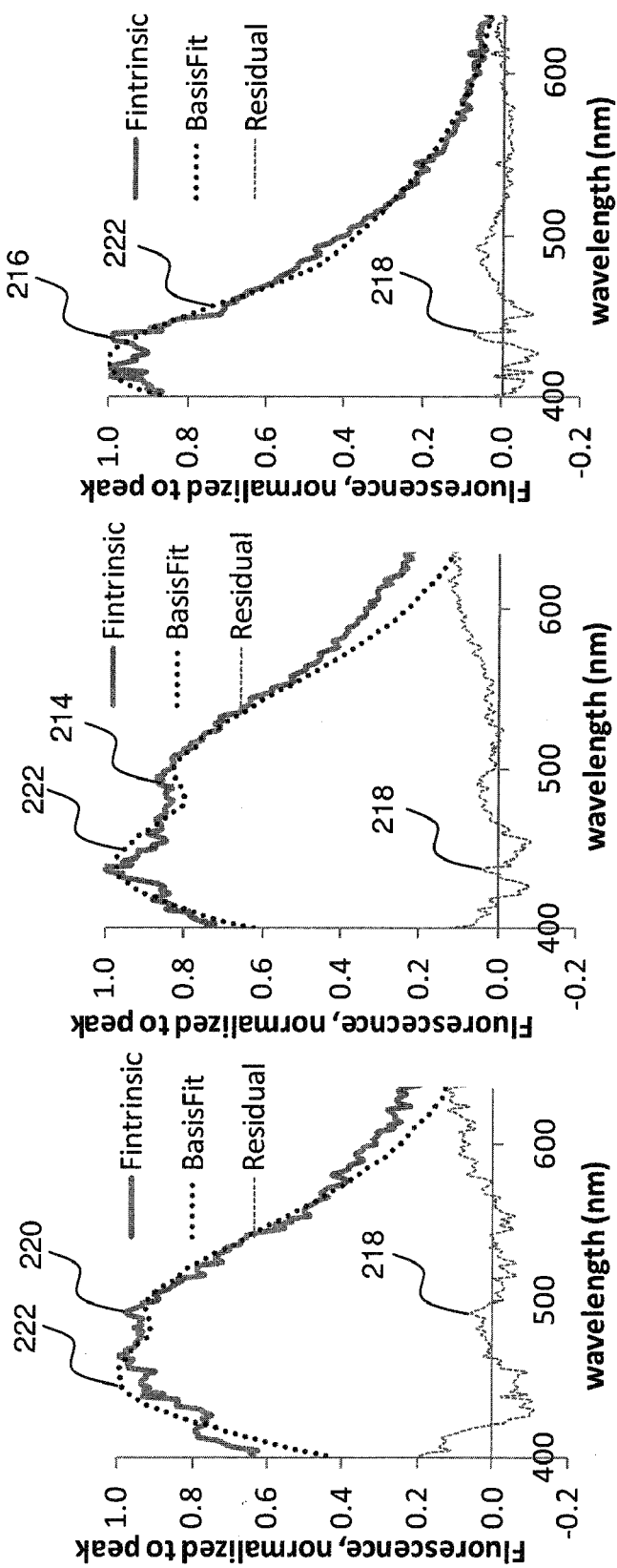

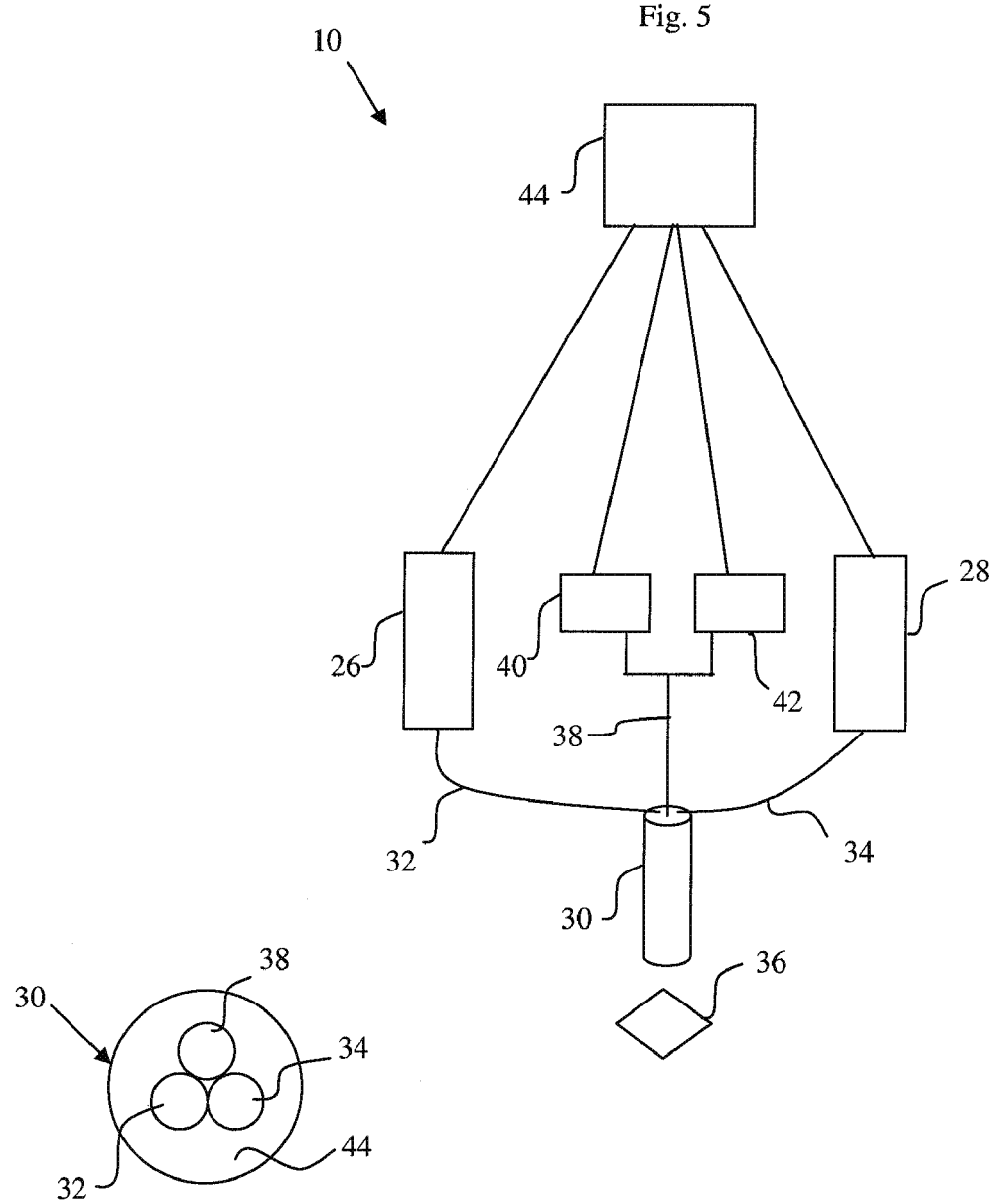

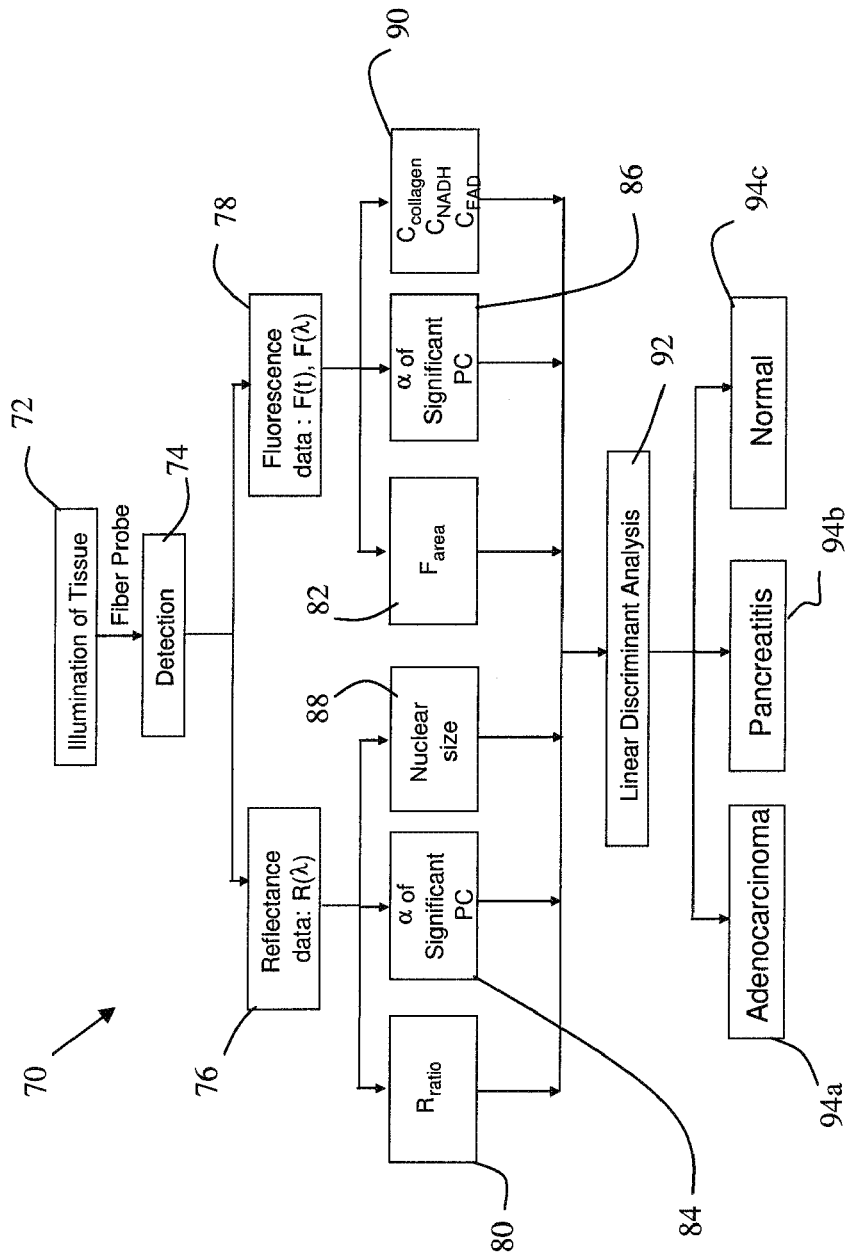

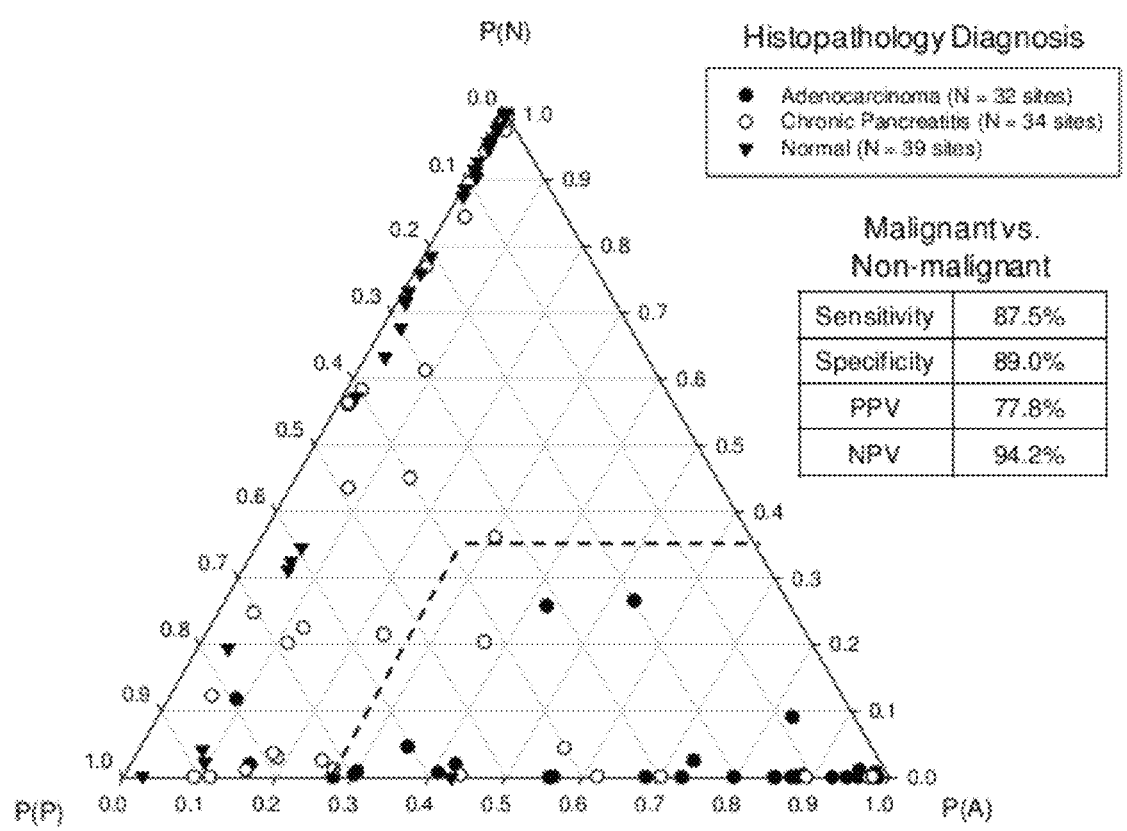

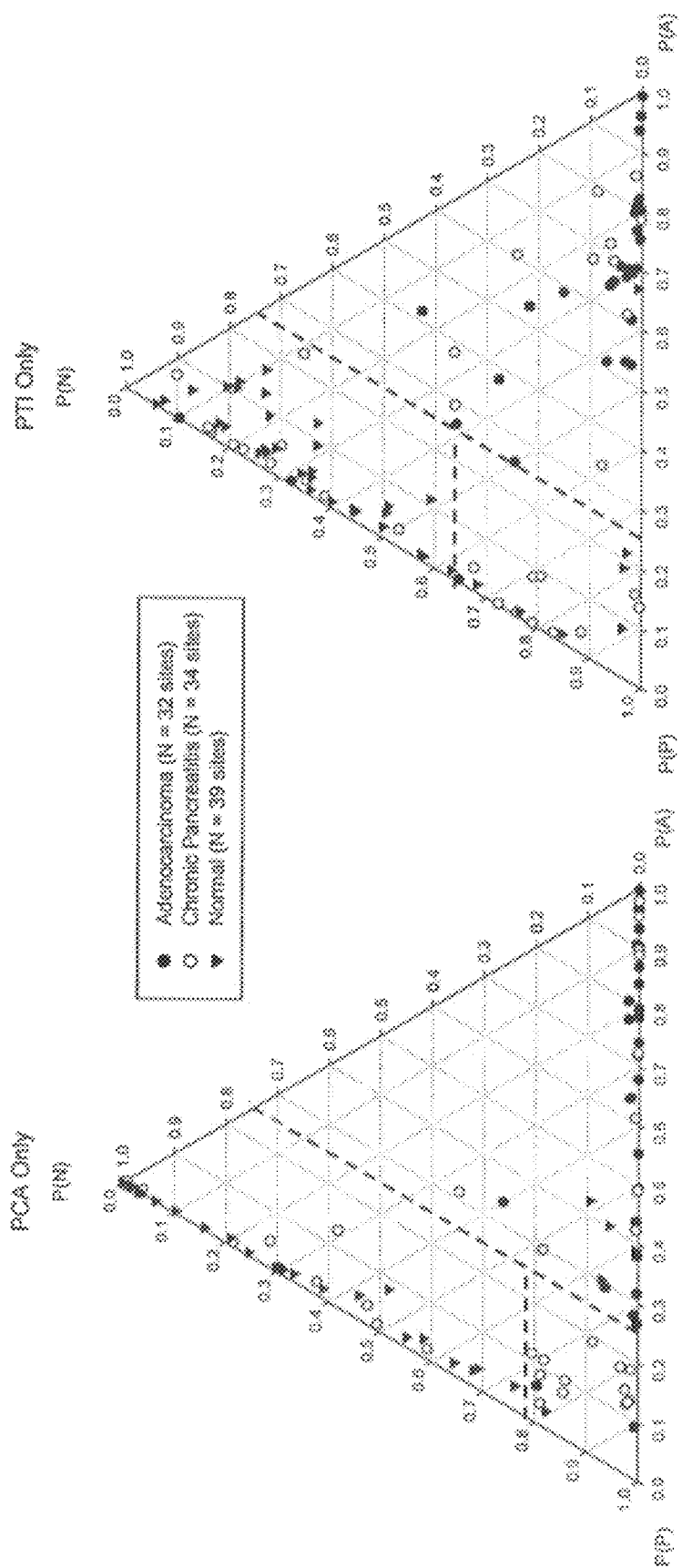
Fig. 30 (a) and (b)

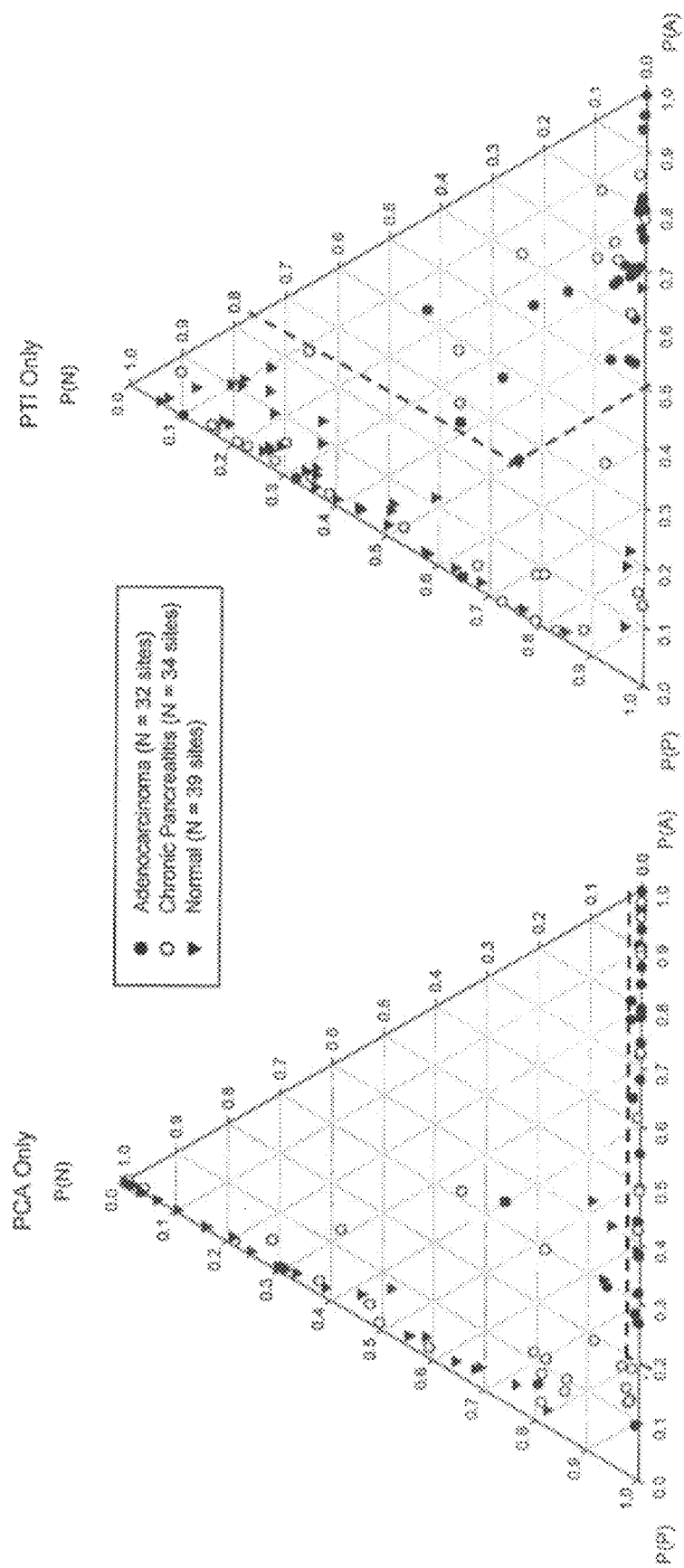
Fig. 30 (c) and (d)

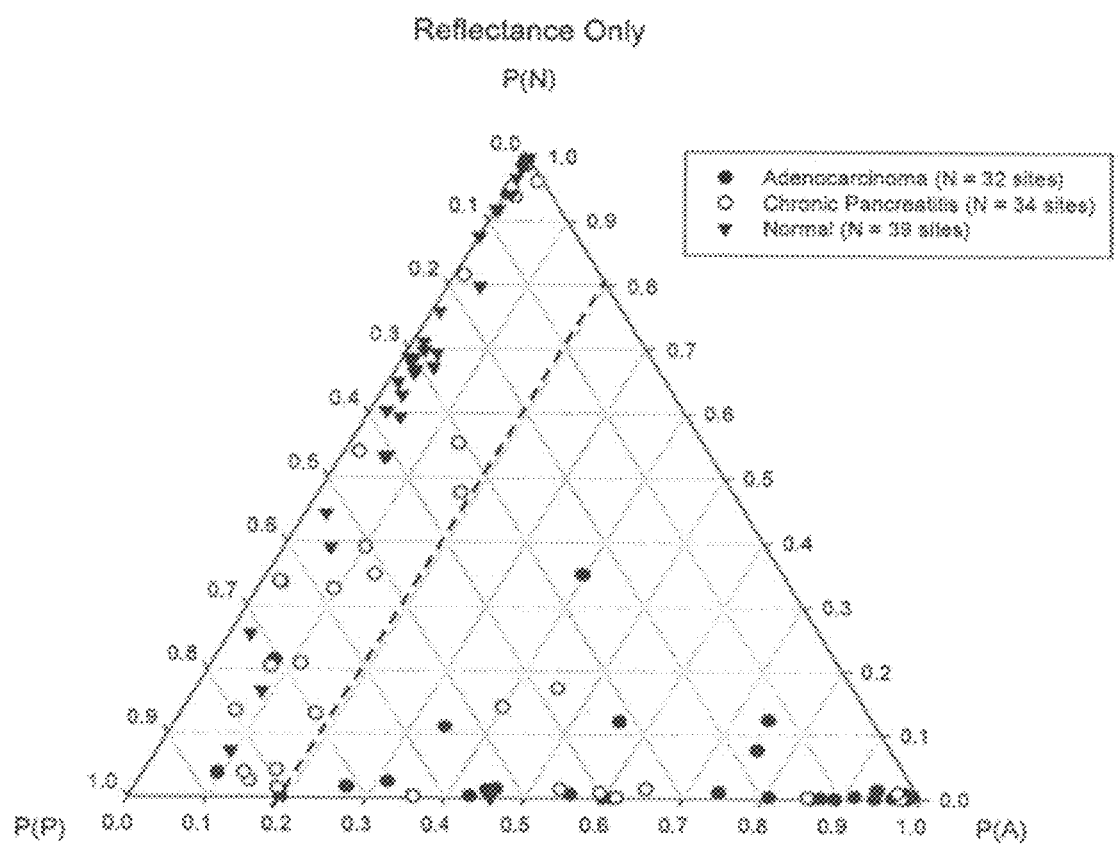

MULTIMODAL SPECTROSCOPIC SYSTEMS AND METHODS FOR CLASSIFYING BIOLOGICAL TISSUE

CROSS-REFERENCE TO RELATED APPLICATION

The instant application claims priority to U.S. Provisional Patent Application Ser. No. 61/487,572, filed May 18, 2011, and as a continuation in part of U.S. Non-Provisional patent application Ser. No. 12/882,131, filed Sep. 9, 2010, which claims priority to U.S. Provisional Patent Application Ser. No. 61/242,126 filed Sep. 14, 2009, and is a continuation in part of U.S. Non-Provisional patent application Ser. No. 12/479,600, filed Jun. 5, 2009, which claims priority to U.S. Provisional Patent Application Ser. No. 61/058,966, filed Jun. 5, 2008, the entire disclosures of which are expressly incorporated herein by reference.

STATEMENT REGARDING FEDERALLY SPONSORED RESEARCH OR DEVELOPMENT

The invention was made with government support under CA114542 awarded by the National Institutes for Health. The government has certain rights in the invention.

FIELD OF THE INVENTION

The present invention generally relates to medical imaging systems and in particular, to employing multimodal spectroscopy in the diagnosis of biological tissue.

BACKGROUND OF THE INVENTION

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference, including any references cited in the articles, patents, patent applications and documents cited herein. Applicants reserve the right to physically incorporate into this application any and all materials and information from any such articles, patents, patent applications, or other documents.

Pancreatic adenocarcinoma has a five-year survival rate of only 6%, making it the fourth-leading cause of cancer death in the United States. "Cancer Statistics 2010," www.cancer.org. Current diagnostic procedures are unable to diagnose the disease in its early stages. T. P. Yeo, et al., "Pancreatic cancer," Current Problems in Cancer 26, 176-275 (2002). In addition, diagnosis is compromised due to an overlap of symptoms with pancreatitis (inflammation of the pancreas). As a result, endoscopic ultrasound-guided fine needle aspiration (EUS-FNA), an established method for the diagnosis of pancreatic adenocarcinoma, has only 54% sensitivity for cancer in the setting of pancreatitis.

A. Fritscher-Ravens et al "Comparison of endoscopic ultrasound-guided fine needle aspiration for focal pancreatic lesions in patients with normal parenchyma and chronic pancreatitis," Am. J. Gastroenterol. 97, 2768-2775 (2002). As many as 9% of patients undergo complicated Whipple surgery to remove a significant portion of their pancreas, only to reveal absence of the disease during pathological examination of the resected specimen. S. C. Abraham et al., "Pancreaticoduodenectomy (Whipple Resections) in Patients Without Malignancy: Are They All 'Chronic Pancreatitis'?," The American Journal of Surgical Pathology 27, 110-120 (2003).

Clearly, the detection of the disease in its early stages and its distinction from pancreatitis would greatly reduce the instances of unnecessary surgery, and more importantly, improve the chances of patient survival.

Multiple studies over the years have employed optical techniques as a means for minimally invasive detection of breast, cervical, colon, and esophageal cancer, among other things. Z. Volynskaya et al., "Diagnosing breast cancer using diffuse reflectance spectroscopy and intrinsic fluorescence spectroscopy," J Biomed Opt 13, 024012 (2008); G. Zonios et al., "Diffuse reflectance spectroscopy of human adenomatous colon polyps in vivo," Applied Optics 38, 6628-6637 (1999); S. K. Chang et al., "Model-based analysis of clinical fluorescence spectroscopy for in vivo detection of cervical intraepithelial dysplasia," J Biomed Opt 11, -(2006); and I. Georgakoudi and M. S. Feld, "The combined use of fluorescence, reflectance, and light-scattering spectroscopy for evaluating dysplasia in Barrett's esophagus," Gastrointestinal Endoscopy Clinics of North America 14, 519-537 (2004).

However, there is little support for applying optical methods for pancreatic cancer detection, possibly owing to the relatively inaccessibility of the pancreas.

Recently, it is understood that Optical Coherence Tomography (OCT) has been applied to both in vivo and ex vivo detection of pancreatic cancer. P. A. Testoni et al., "Intraductal optical coherence tomography for investigating main pancreatic duct strictures," Am J Gastroenterol 102, 269-274 (2007); P. A. Testoni et al., "Optical coherence tomography to detect epithelial lesions of the main pancreatic duct: an Ex Vivo study," Am J Gastroenterol 100, 2777-2783 (2005).

Furthermore, Near-Infrared Spectroscopy and Partial-wave microscopic spectroscopy have also been applied in ex vivo studies. V. R. Kondepati et al., "Near-infrared fiber optic spectroscopy as a novel diagnostic tool for the detection of pancreatic cancer," J Biomed Opt 10, -(2005); H. Subramanian et al., "Partial-wave microscopic spectroscopy detects subwavelength refractive index fluctuations: an application to cancer diagnosis," Opt Lett 34, 518-520 (2009).

In the latter, pancreatic cancer cells on microscopic slides were studied. Four-dimensional elastic light-scattering spectroscopy, and low-coherence enhanced backscattering spectroscopy have been employed for the ex vivo study of duodenal tissue based on a field effect hypothesis that predicts changes in the duodenum owing to the presence of cancer in the pancreas. V. Turzhitsky et al., "Investigating population risk factors of pancreatic cancer by evaluation of optical markers in the duodenal mucosa," Dis Markers 25, 313-321 (2008); Y. Liu et al., "Optical markers in duodenal mucosa predict the presence of pancreatic cancer," Clin Cancer Res 13, 4392-4399 (2007).

A number of chemometric and statistical techniques have been used in the literature to develop tissue classification algorithms employing optical spectroscopy data. These include, multiple linear regression analysis, linear discriminant analysis, backpropagating neural network analysis, principal component analysis, logistic discrimination, partial least squares, multivariate linear regression, and support vector machine. N. Ramanujam et al., "Development of a multivariate statistical algorithm to analyze human cervical tissue fluorescence spectra acquired in vivo," Lasers in Surgery and Medicine 19, 46-62 (1996); Z. F. Ge et al., "Identification of colonic dysplasia and neoplasia by diffuse reflectance spectroscopy and pattern recognition techniques," Applied Spectroscopy 52, 833-839 (1998); G. M. Palmer et al., "Comparison of Multiexcitation Fluoroescence and Diffuse Reflectance Spectroscopy for the Diagnosis of Breast Cancer," Ieee T Bio-Med Eng 50, 1233-1242 (2003); S. K. Chang et al., "Combined reflectance and fluorescence spectroscopy for in vivo detection of cervical pre-cancer," J Biomed Opt 10, 024031 (2005); A. Dhar et al., "Elastic scattering spectroscopy for the diagnosis of colonic lesions: initial results of a novel optical biopsy technique," Gastrointest Endosc 63, 257-261 (2006); S. C. Chu et al., "Comparison of the performance of linear multivariate analysis methods for normal and dyplasia tissues differentiation using autofluorescence spectroscopy," Ieee T Bio-Med Eng 53, 2265-2273 (2006); and G. Salomon et al., "The Feasibility of Prostate Cancer Detection by Triple Spectroscopy," Eur Urol, (2008). Additionally, quantitative photon-tissue interaction models of reflectance and fluorescence have been utilized in optical methods for detecting breast cancer Z. Volynskaya, et al., "Diagnosing breast cancer using diffuse reflectance and intrinsic fluorescence spectroscopy," J. Biomed. Opt. 13, 024012 (2008), colon cancer G. Zonios, et al., "Diffuse reflectance spectroscopy of adenomatous colon polyps in vivo," Appl. Opt. 38, 6628-6637 (1999), cervical cancer S. K. Chang, et al., "Model-based analysis of clinical fluorescence spectroscopy for in vivo detection of cervical intraepithelial dysplasia," J. Biomed. Opt. 11, 024008 (2006), and Barrett's esophagus I. Georgakoudi and M. S. Feld, "The combined use of fluorescence, reflectance, and light-scattering spectroscopy for evaluating dysplasia in Barrett's esophagus," Gastroint. Endosc. Clin. N. Am. 14, 519-537 (2004). Recently, photon-tissue interaction modeling was incorporated into an optical study of murine tumors consisting of human pancreatic cancer cells, in order to quantitatively distinguish different tumor regions V. Krishnaswamy, et al., "Quantitative imaging of scattering changes associated with epithelial proliferation, necrosis, and fibrosis in tumors using microsampling reflectance spectroscopy," J. Biomed. Opt. 14, 014004 (2009).

SUMMARY OF THE INVENTION

The invention is generally directed to systems and methods configured for, among other things, directing electromagnetic radiation or light of a plurality of wavelengths onto biological tissue either ex vivo or in vivo to produce a measurable spectroscopic event; collecting a plurality of spectroscopic response data regarding the biological tissue, which may include fluorescence and reflectance spectra, time-resolved spectroscopy, time-resolved fluorescence spectroscopy or decay measurements; comparing the response data with preset criteria that correlates the collected data with tissue attributes which facilitate a tissue classification, that is, attributes which may be indicative of a particular condition (for example, the presence of a tumor or disease) and/or probative of the relative health of the tissue (for example, normal or abnormal); determining which, if any, of the preset criteria are satisfied; and classifying the tissue based on the tissue attributes identified by the preset criteria satisfied.

The systems and methods described herein are well-suited to be used in conjunction with or as a substitute for random biopsies, since the optical systems and methods are non-invasive, do not require tissue removal, and can be performed in-vivo, or both. Moreover, they are fast (can be applied in real time), are relatively non-expensive, are able to work on microscopic scale, and thus can find very small sites for tissue diagnosis, which may be missed by random biopsies. The systems and methods herein are also well-suited to be used in endoscopic ultrasound-guided procedures and apparatus, or delivered through an endoscope or needle by a trained professional.

In some embodiments, the invention is directed to a method of employing multimodal spectroscopy to classify pancreatic tissue in vivo comprising the steps of: illuminating pancreatic tissue in vivo to produce a measurable spectroscopic event; collecting spectroscopic response data from the spectroscopic event, wherein the response data includes measurements derived from steady-state reflectance, steady-state fluorescence, and time-resolved fluorescence signals associated with the tissue; comparing the response data with a photon-tissue interaction (PTI) model for the reflectance and fluorescence spectra to extract tissue parameters from the measured data and comparing the response data with a multi-exponential decay model of the time-resolved fluorescence in order to extract amplitudes and lifetimes from the measured data; and classifying the tissue as either normal, adenocarcinoma or pancreatitis based on the comparisons.

In some embodiments, the illuminating of the biological tissue sample as described in the aforementioned method is configured to produce a plurality of measurable spectroscopic events. An event may include illumination wavelengths of about 400 nm to about 750 nm to facilitate collecting reflectance signal measurements and another event may include illumination wavelengths of about 355 nm to facilitate collecting fluorescence signal measurements.

In some embodiments of the aforementioned method, the photon-tissue interaction model for the reflectance is modified to include a direct fit of the semi-empirical reflectance equation to the data instead of scaling an average measured "canonical normal" spectrum.

In some embodiments of the aforementioned method, the photon-tissue interaction model for the reflectance is modified to consider the packaging of blood into red blood cells and cylindrical blood vessels.

In some embodiments of the aforementioned method, the photon-tissue interaction model for the reflectance is modified to include expanded ranges of oxy- and deoxy-hemoglobin concentrations that range from about 2 µM to about 2.048 mM, as defined by the formula $[Hb]=(1\ \mu M)(2^k)$, where k is varied from 1-11 when the model is being fit to the data.

In some embodiments of the aforementioned method, the photon-tissue interaction model for the fluorescence is modified such that the absorption and scattering coefficients extracted from the best fit of the reflectance model are both used to correct the fluorescence for attenuation artifacts to obtain the intrinsic fluorescence.

In some embodiments of the aforementioned method, the photon-tissue interaction model for the fluorescence is modified such that the non-normalized fluorescence data is corrected for attenuation artifacts to obtain the intrinsic fluorescence.

In some embodiments of the aforementioned method, the photon-tissue interaction model for the fluorescence is modified wherein the intrinsic fluorescence is fit with a linear combination of basis spectra without blue-shifting the basis spectra.

In some embodiments of the aforementioned method, the photon-tissue interaction model for the reflectance is modified to consider varying absorption from beta-carotene, using a pre-published beta-carotene absorption spectrum.

In some embodiments of the aforementioned method, the photon-tissue interaction model for the reflectance is modified to consider varying the refractive indices of the cell nuclei and the surrounding medium.

In some embodiments of the aforementioned method, the photon-tissue interaction model for the reflectance is modified to consider varying the mean blood vessel radius.

In some embodiments of the aforementioned method, the photon-tissue interaction model for the reflectance is modified wherein the model is fit to non-normalized reflectance data and the amplitude and shift in the semi-empirical equation are allowed to vary.

The invention is also directed to a system of employing multimodal spectroscopy to classify pancreatic tissue in vivo comprising: a probe member comprising a plurality of optical fibers, wherein at least one of the plurality of fibers is configured for illuminating pancreatic tissue in vivo to produce a measurable spectroscopic event and at least one other of the plurality of fibers is configured for collecting spectroscopic response data from the spectroscopic event; and a processing device for analyzing measurements derived from the steady-state reflectance, steady-state fluorescence, and time-resolved fluorescence signals from the spectroscopic response data associated with the tissue, comparing the measurements with a photon-tissue interaction model for the reflectance and a multi-exponential decay model of the time-resolved fluorescence in order to extract amplitudes and lifetimes from the measured data and classifying the tissue as either normal, adenocarcinoma, or pancreatitis based on the comparisons.

The probe member may include at least three optical fibers, wherein two of the three optical fibers are used for illuminating the biological tissue sample. The system may include a display device for displaying the measurements and classification.

The system may include one or more additional processing devices in communication with a database or memory device, data input/output device and display device. The memory device may include data relating to the measurements and models, modified or otherwise, as employed herein.

These and other aspects of the invention will become more readily apparent to those of ordinary skill in the art from the following detailed description when considered in connection with the accompanying figures.

BRIEF DESCRIPTION OF THE DRAWINGS

FIGS. 2A and 2B provide graphs illustrating wavelength-resolved scattering (FIG. 2A) and absorption (FIG. 2B) coefficients of normal pancreatic tissue, pancreatic adenocarcinoma, and pancreatitis, extracted from representative fits of experimental data to the reflectance model;

FIGS. 3A, 3B and 3C provide graphs illustrating intrinsic fluorescence spectra of normal pancreatic tissue (FIG. 3A), pancreatitis (FIG. 3B), and pancreatic adenocarcinoma (FIG. 3C), shown with a representative fit to a linear combination of measured and blue-shifted collagen, NADH, and FAD basis spectra;

FIG. 5 is a schematic diagram of a system constructed in accordance with some embodiments of the invention;

FIG. 6 is a cross sectional view of optical fibers at the distal end of an exemplary probe used with a system constructed accordance with some embodiments of the invention;

FIG. 7 is a flow chart illustrating the manner in which the hybrid algorithm may be employed in some embodiments to classify a pancreatic tissue site into normal, adenocarcinoma, or pancreatitis;

FIG. 29 provides a ternary plot of the optical diagnosis probabilities for distinguishing adenocarcinoma, pancreatitis, and normal pancreatic tissue, using thresholds on the probabilities of adenocarcinoma and normal to achieve optimal classification accuracy for distinguishing malignant (adenocarcinoma) from non-malignant (normal and pancreatitis) human pancreatic tissues;

FIG. 30 provides ternary plots of optical diagnosis probabilities for distinguishing adenocarcinoma, pancreatitis, and normal pancreatic tissue, using the PCA model alone (a, c) and the PTI model alone (b, d), with manual thresholds (a, b) on the diagnosis probabilities to provide optimal classification accuracy for distinguishing malignant (adenocarcinoma) from non-malignant (normal and pancreatitis) human pancreatic tissues, and cost-based thresholds (c, d) on the diagnosis probabilities to distinguish between all three tissue types;

DETAILED DESCRIPTION OF INVENTION

Figure 1A:
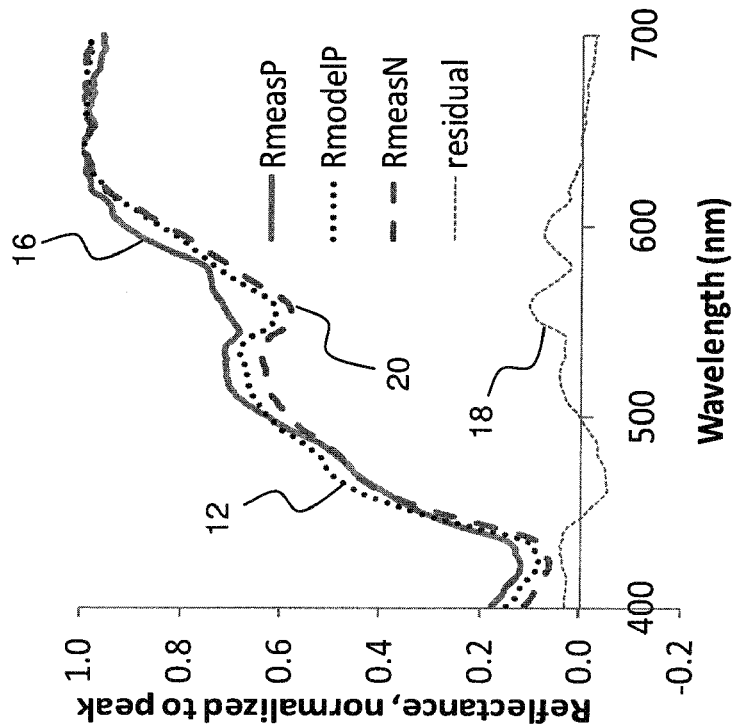
FIGS. 1A and 1B provide graphs illustrating a representative fit of a mathematical model, formed according to some embodiments of the invention, versus average measured result for reflectance spectra of pancreatic adenocarcinoma (FIG. 1A) and pancreatitis (FIG. 1B), with residuals.

Some embodiments of the invention employ multimodal optical spectroscopic systems and methods to obtain data from biological tissue and compare the data with preset criteria configured to aid in the diagnosis of the tissue health or condition, wherein the preset criteria relates the data with the most probable attributes of the tissue. The multimodal spectroscopic systems employed may include fluorescence spectroscopy, reflectance spectroscopy and time-resolved spectroscopy, among others.

In some embodiments, data obtained through multimodal optical spectroscopy is correlated with the results of a microscopic histological examination of a normal tissue sample to develop the preset criteria by which further tissue samples are to be assessed. In particular, the preset criteria may be based on a relationship between spectral data and the histological aspects of the tissue which are most likely to be indicative of a specific attribute so as to lead to a unique classification of the tissue. For example, the preset criteria may ultimately be used to provide attributes such as the NADH content, FAD content, collagen content and/or nuclear size values associated with the tissue, or any other characteristics which are probative of tissue health, indicative of certain conditions, or otherwise provide insight into the relative health of the tissue.

Thus, systems and methods of the invention can be used to facilitate real-time (or near real-time) diagnosis of further tissue samples and may be employed with excised tissue or in vivo. Systems and methods of the invention may be used to ascertain tissue conditions and classify tissue during a surgical procedure. The systems and methods discussed herein may be utilized to guide a biopsy procedure. For example, systems and methods of the invention may be incorporated for a variety of fiber probe configurations through any kind of endoscope or needle in a clinic or other facility or with endoscopic ultrasound-guided fine needle aspiration (EUS-FNA) procedures.

As mentioned above, the preset criteria relate measured data to tissue attributes in a manner which facilitates a tissue classification. Depending on the application, tissue classifications may include normal, abnormal, inflammation, disease or adenocarcinoma, for example. In some embodiments, the measured data may linked by the preset criteria to histological features which are hallmarks of particular tissue conditions such as adenocarcinoma. In this manner, some embodiments of the invention utilize the measured data to quantitatively distinguish between normal and abnormal tissue conditions.

Systems and methods of the invention employ multimodal optical spectroscopy, and may include exposing biological tissue to a source of electromagnetic radiation to produce a spectral event, collecting spectral response data regarding the tissue at a plurality of wavelengths, correlating the spectral response data with the histology of the tissue based on preset criteria, and classifying the tissue condition based on the preset criteria satisfied. In some embodiments, the spectral response data collected includes fluorescence, reflectance and time-resolved fluorescence decay information, but may include any combination of parameters derived from the spectral event or response data that are likely to provide complementary information about the biochemical, architectural and morphological state of the tissue of interest.

The preset criteria may be derived by a variety of methods, such as the empirical data collection and mathematical modeling techniques discussed herein with respect to pancreatic tissue. Although the illustrations and examples herein focus on pancreatic tissues, it should be readily apparent that the invention is not to be limited to pancreatic tissues, and mathematical models of the invention are also of potential use for optical diagnostic applications in other biological tissues. It should be understood that the embodiments of the invention may be useful for various applications and procedures throughout the medical arts. Thus, the techniques and embodiments discussed herein should not be construed as limiting, as analyzing pancreatic tissue to differentiate between normal pancreatic tissue, pancreatitis, and adenocarcinoma is merely an example of a suitable application for the embodiments of the invention.

Illustration I

1. Introduction

Systems and methods discussed herein advantageously provide the ability to quantitatively explain prominent disease-related changes to human pancreatic tissue in terms of biologically meaningful parameters based on spectral data consisting of collected fluorescence and reflectance spectra. The systems and methods of the invention further provide the ability to classify pancreatic tissue as normal, pancreatic or adenocarcinoma. In some embodiments, the preset criteria is derived from mathematical modeling of experimentally measured spectral data used to quantitatively describe differences in the reflectance and fluorescence spectra of normal pancreatic tissue, pancreatic adenocarcinoma, and pancreatitis.

For example, it has been found that pancreatic adenocarcinoma has larger nuclei than benign pancreatic tissue, and both adenocarcinoma and chronic pancreatitis have more collagenous stroma than normal pancreatic tissue. The mathematical model of reflectance quantitatively linked increased nuclear size in adenocarcinoma to changes in the measured reflectance spectra, particularly within the range from about 455 nm to about 525 nm. The fluorescence model quantitatively linked increased collagen content in pancreatitis and adenocarcinoma to changes in the composition of the measured fluorescence spectra. Fitting the reflectance model to the experimental data also enabled the extraction of values for the optical absorption and scattering coefficients of human pancreatic tissues.

The mathematical model of some embodiments provided a quantitative link between optical spectroscopy and tissue histology as shown in Table 1, suggesting a potential clinical application of optical spectroscopy and modeling to minimally invasive early cancer diagnostics in the pancreas.

TABLE 1

| Key histological features of pancreatic tissues detected by optical spectroscopy | | |
|---|---|---|
| Pancreatic tissue | Key histological features (relative to normal pancreatic tissue) | Optical signature found in |
| Adenocarcinoma | Increased nuclear size | Reflectance spectra |
|  | Greater stromal collagen content | Fluorescence spectra |
| Pancreatitis | Greater stromal collagen content | Fluorescence spectra |

2. Clinical Measurements of Tissue Optical Spectra

In this embodiment, a Reflectance and Fluorescence Lifetime Spectrometer (RFLS) was used to obtain reflectance and fluorescence measurements of human pancreatic tissue within about 15 minutes of removal via Whipple resection at the University of Michigan Medical Center. Reflectance measurements were acquired by using a CW tungsten halogen lamp (e.g., HL 2000FHSA, Ocean Optics, Dunedin, Fla.) to deliver white light (about 400 to about 750 nm wavelength) to the tissue; fluorescence measurements utilized a 355 nm pulsed excitation source (e.g., PNV001525-140, JDS Uniphase, San Jose, Calif.). A spectrograph (e.g., MS 125, Oriel Instruments, Stratford, Conn.) and an intensified charge-coupled device (ICCD) camera (e.g., ICCD 2063, Andor Technology, Belfast, Northern Ireland) were used to detect tissue reflectance (about 400 to about 750 nm) and fluorescence (about 360 to about 700 nm) spectra. The light from the lamp and the laser was delivered to the tissue via two separate optical fibers with core diameters of 600 µm. The reflected or emitted fluorescence photons from the tissue were collected and transported to the detectors by a third identical fiber.

Measurements were taken at five sites on each tissue specimen. One pancreatectomy specimen was evaluated from each of two different patients. Each measured site was biopsied under the supervision of a clinical pathologist, and the biopsied samples were evaluated histologically. For the first patient, two of the sites were histologically normal and three were pancreatitis, while for the second patient, all five sites sampled were adenocarcinoma. There were noticeable differences in both the reflectance and fluorescence spectra of the three tissue types, most notably around 500 nm for the reflectance spectra and near 400 nm for the fluorescence spectra.

3. Mathematical Model of Reflectance Spectra: Theory and Results

3.1 Modeling Scattering and Absorption Coefficients of Pancreatic Tissues

The lineshapes of reflectance spectra from biological tissues are known to be primarily dependent on the absorption and scattering coefficients of the media. Absorbers such as blood will attenuate the light, while scatterers such as cell nuclei and collagen fibers will change the paths of the photons, eventually leading some of them back to the tissue surface. Mie theory was used to describe the scattering coefficient $\mu_s$, as a function of wavelength, in terms of the size and density of the scatterers in the tissue. A. Sefkow, et al., "Method for Measuring Cellular Optical Absorption and Scattering Evaluated Using Dilute Cell Suspension Phantoms," Appl. Spectrosc. 55, 1495-1501 (2001); C. F. Bohren and D. R. Huffman, *Absorption and Scattering of Light by Small Particles* (Wiley, 1983); L. T. Perelman, et al., "Observation of Periodic Fine Structure in Reflectance from Biological Tissue: A New Technique for Measuring Nuclear Size Distribution," Phys. Rev. Lett. 80, 627-630 (1998); and I. S. Saidi, et al. "Mie and Rayleigh modeling of visible-light scattering in neonatal skin," Appl. Opt. 34, 7410-7418 (1995).

Two Mie theory terms were used: one for spherical scatterers (cell nuclei) and another for cylindrical scatterers (collagen fibers). For the spherical Mie scattering term, the Van de Hulst approximation was used:

$$\mu_s(\lambda) = \frac{1}{2}\pi N_s L^2 \left[ 1 - \frac{\sin\left(\frac{2\delta}{\lambda}\right)}{\left(\frac{\delta}{\lambda}\right)} + \left(\frac{\sin\left(\frac{\delta}{\lambda}\right)}{\left(\frac{\delta}{\lambda}\right)}\right)^2 \right]; \quad (1)$$

$$\delta = \pi L(n_s - n_m).$$

In Eq. (1), Lo is the scatterer diameter, Ns is the number of scatterers per unit volume, and $n_s$ ($n_m$) is the index of refraction of the scatterer (surrounding medium). The wavelength $\lambda$ is defined as $\lambda_{vac}/n_m$, where $\lambda_{vac}$ is the wavelength of the incident light in vacuum. For all pancreatic tissue types in this study, $n_m$ was assumed to be 1.33 (for water), while $n_s$ was set as a free parameter The values of L and $N_s$ were estimated from histology to be 9 μm and 7×10$^7$ cm$^{-3}$, respectively. The parameter $N_s$ was kept constant for all tissue types. For both pancreatitis and adenocarcinoma, a dilation factor $L_d/Lo$ was applied to the nuclear diameter. The cylindrical scattering term was modeled by a combination of Bessel functions, in which the diameter and refractive index of the collagen fibers were 3 μm and 1.35, respectively. The spherical and cylindrical Mie scattering terms were chosen over the commonly-used approximation $\mu_s = A\lambda^{-b}$ because they are explicit functions of scatterer size. The absorption coefficient $\mu_a$ was modeled as a linear combination of the extinction coefficients of oxy- and deoxy-hemoglobin, weighted according to their concentrations in the tissue:

$$\mu_a(\lambda) = [Hb]\epsilon_{Hb} + [HbO_2]\epsilon_{HbO_2}. \quad (2)$$

G. Zonios, et al., "Diffuse reflectance spectroscopy of adenomatous colon polyps in vivo," Appl. Opt. 38, 6628-6637 (1999).

3.2 Modeling Key Features in Reflectance Spectra of Pancreatitis and Adenocarcinoma The key diagnostic feature of the measured reflectance was increased amplitude between 455 nm and 525 nm in the adenocarcinoma spectra, relative to normal pancreatic tissue spectra. An empirical model, previously shown to be accurate in the case of small source-detector separations, was used to model this feature by describing the reflectance spectra $R^{EMP}_i(\lambda)$ as functions of tissue absorption and scattering:

$$R^{EMP}_i(\lambda) = a\mu'_s(\lambda) \exp\left(-\frac{C_{corr}(\lambda)\mu_a(\lambda)b}{[C_{corr}(\lambda)\mu_a(\lambda)\mu'_s(\lambda)]^c}\right). \quad (3)$$

R. Reif, et al., "Analysis of changes in reflectance measurements on biological tissues subjected to different probe pressures," J. Biomed. Opt. 13, 010502 (2008); R. Reif, et al., "Analytical model of light reflectance for extraction of the optical properties in small volumes of turbid media," Appl. Opt. 46, 7317-7328 (2007).

In Eq. (3), $\lambda_s'(\lambda)$ is the reduced scattering coefficient, equal to $\lambda_s(1-g)$, where g is the anisotropy of the tissue (set to 0.9 for all $\lambda$). The factor $C_{corr}(\lambda)$ describes the confinement of oxy- and deoxy-hemoglobin to cylindrical blood vessels. R. L. P. van Veen et al., "Diffuse-reflectance spectroscopy from 500 to 1060 nm by correction of inhomogeneously distributed absorbers," Opt. Lett. 27, 246-248 (2002). The parameters a, b, and c are fitting constants (related to probe design) whose respective values were estimated to be 0.11, 0.22, and 0.2. These values do not vary significantly when the tissue-probe refractive index mismatch is changed. The value of b is somewhat dependent on probe source-detector separation, but changing b by as much as 50% was found to have very little effect on the modeled pancreatic tissue spectra. Since the reflectance model (Eq. (4)) employed in this study only utilizes ratios (and not raw values) of $R^{EMP}_i$ for different tissue types, it was considered reasonable to approximate a, b, and c as 0.11, 0.22, and 0.2 in Eq. (3). For the remainder of the text, the subscript i in Eq. (3) will be denoted as N for normal pancreatic tissue, P for pancreatitis, or A for pancreatic adenocarcinoma.

To model the reflectance spectra of diseased pancreatic tissue, Eq. (3) was used to generate a wavelength-resolved scaling factor to transform the experimentally measured reflectance spectrum $R^{MEAS}_N(\lambda)$ of normal pancreatic tissue into an accurate model for the adenocarcinoma reflectance spectrum $R^{MODEL}_A(\lambda)$ and the pancreatitis reflectance spectrum $R^{MODEL}_P(\lambda)$, according to the equations:

$$R^{MODEL}_A(\lambda) = R^{MEAS}_N(\lambda)(R^{EMP}_A(\lambda)/R^{EMP}_N(\lambda)); \quad (4)$$

$$R^{MODEL}_P(\lambda) = R^{MEAS}_N(\lambda)(R^{EMP}_P(\lambda)/R^{EMP}_N(\lambda)). \quad (5)$$

Optimal fits of Eqs. (4) and (5) to the respective measured adenocarcinoma and pancreatitis reflectance spectra were determined via minimization of a cost function $C_R$, which was equal to the average magnitude of the difference between the reflectance model and measured reflectance spectrum over the 400-700 nm wavelength range. For each tissue type, every individual measured spectrum was first normalized to peak intensity, then these spectra were averaged and the result was normalized to peak intensity again. All of the modeled reflectance spectra were also normalized to peak intensity.

In the fitting procedure described above, the nuclear dilation factor $L_d/L_o$ for diseased pancreatic tissue (adenocarcinoma and pancreatitis) was varied from 1.0 to 1.9 in steps of 0.1, and the nuclear refractive index $n_{sd}$ of diseased pancreatic tissue was varied from 1.370 to 1.400, in steps of 0.005. The total hemoglobin concentration [Hb]tot was varied from 15 μM to 25 μM for normal pancreatic tissue and 2.5 μM to 25 μM for diseased tissue (in steps of 2.5 μM for all tissue types). The blood oxygen saturation $SO_2$ was varied from 0.1 to 0.9 (in steps of 0.2) for all tissue types. The fitting procedure described above was performed for each of three different values of the nuclear refractive index nsn of normal pancreatic tissue: 1.370, 1.375, and 1.380. This range and these values were identified in part because of the results of studies conducted on freshly excised diseased and normal human tissues [V. Backman, R. Gurjar, K. Badizadegan, L. Itzkan, R. R. Dasari, L. T. Perelman, and M. S. Feld, "Polarized light scattering spectroscopy for quantitative measurement of epithelial cellular structures in situ," IEEE J. Sel. Top. Quantum Electron. 5(4), 1019-1026 (1999).], and in part because we observed that the algorithm extracted physically reasonable values of both $L_d/L_o$ and $n_{sd}$ that did not vary much as $n_{sn}$ was changed. The set of free parameter values that minimized $C_R$ was extracted from each fit, as reported below. The fitting method described here was compared with a nonlinear least-squares method, and t-tests demonstrated that there were no statistically significant differences (p>0.25) between the tissue parameters extracted from the two fitting methods.

In the diagnostically important wavelength range between about 455 and about 525 nm, where the adenocarcinoma reflectance spectra differed significantly from both the normal and pancreatitis spectra, the error in fit between the adenocarcinoma model and measured adenocarcinoma data was less than 5%.

Figure 1B:
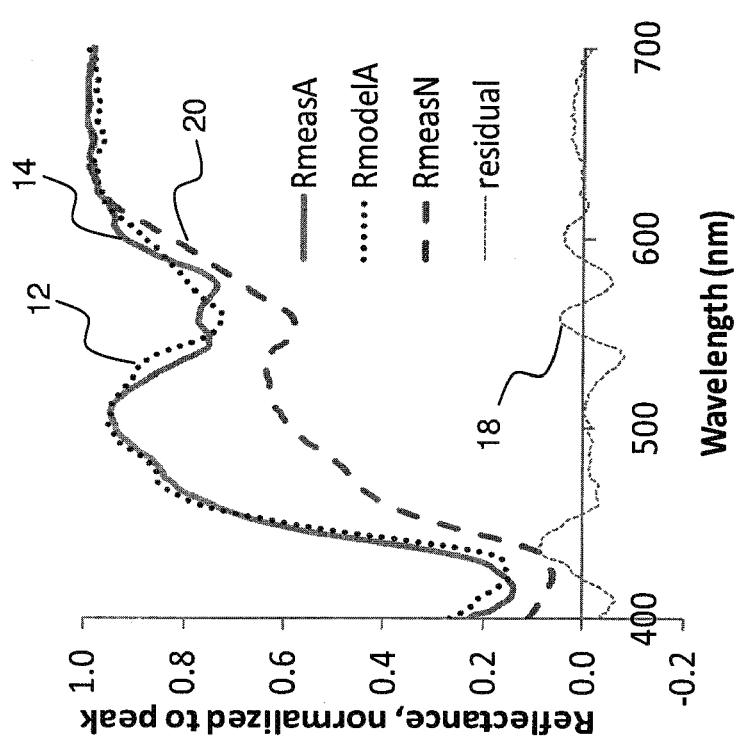

FIGS. 1A and 1B illustrates an aspect of an embodiment of the invention and provides a representative fit of a mathematical model 12 (dotted lines) versus average measured result for reflectance spectra (solid lines) of pancreatic adenocarcinoma (FIG. 1A) 14 and pancreatitis (FIG. 1B) 16, with residuals (small dotted lines) 18. The experimentally obtained reflectance spectrum for normal pancreatic tissue (dashed lines) 20 is shown on both plots for comparison. The optimal fits between the predicted and measured adenocarcinoma reflectance spectra extracted a (mean±standard deviation) value of $L_d/Lo=1.33\pm0.06$ for the nuclear dilation factor and a value of $n_{sd}=1.375$ for the nuclear refractive index. The optimal fits between the predicted and measured pancreatitis reflectance spectra extracted a (mean±standard deviation) value of $L_d/Lo=1.03\pm0.06$ for the nuclear dilation factor and $n_{sd}=1.372\pm0.003$ for the nuclear refractive index. The model revealed that differences in the reflectance spectra of normal pancreatic tissue, pancreatitis, and adenocarcinoma could be quantitatively linked to an increase in nuclear size for adenocarcinoma relative to pancreatitis and normal tissue, a result that is supported by histology [F. Lin, and G. Staerkel, "Cytologic criteria for well differentiated adenocarcinoma of the pancreas in fine-needle aspiration biopsy specimens," Cancer 99(1), 44-50 (2003); M. B. Cohen, D. P. Egerter, E. A. Holly, D. K. Ahn, and T. R. Miller, "Pancreatic adenocarcinoma: regression analysis to identify improved cytologic criteria," Diagn. Cytopathol. 7(4), 341-345 (1991); R. J. Sears, C. W. Duckworth, C. Decaestecker, N. Bourgeois, T. Ledent, J. Deviere, I. Salmon, R. Kiss, and P. Yeaton, "Image cytometry as a discriminatory tool for cytologic specimens obtained by endoscopic retrograde cholangiopancreatography," Cancer 84(2), 119-126 (1998).].

These choices of parameters were in good agreement with results from histology and previous literature. M. Chandra, et al., "Probing pancreatic disease using tissue optical spectroscopy," J. Biomed. Opt. 12, 060501 (2007); M. Chandra, et al., "Pancreatic tissue assessment using fluorescence and diffuse reflectance spectroscopy," Proc. SPIE 6628, 66281R (2007), 8 pgs; T. Imamura, et al., "Quantitative analysis of collagen and collagen subtypes I, III, and V in human pancreatic cancer, tumor-associated chronic pancreatitis, and alcoholic chronic pancreatitis," Pancreas 11, 357-364 (1995). The model revealed that differences in the reflectance spectra of normal pancreatic tissue, pancreatitis, and adenocarcinoma were largely due to an increase in nuclear size for adenocarcinoma relative to pancreatitis and normal tissue.

The spectra from FIGS. 1A and 1B were also compared with a previously published reflectance spectrum taken in vivo from a pancreatic adenocarcinoma xenograft created by injecting human pancreatic cancer cells into the pancreas of a Non-Obese Diabetic/Severe Combined Immunodeficiency (NOD/SCID) mouse. Due to the suppressed immune response in SCID mice, the xenograft had a very low amount of collagen relative to cells. The xenograft also contained more blood than the ex vivo-obtained human pancreatic tissue samples. In spite of these differences, the reflectance spectrum of the xenograft was similar to that of freshly excised human adenocarcinoma from 400-475 nm, a result attributed to the increased size of the cell nuclei in both the xenograft and the ex vivo-obtained adenocarcinoma tissue samples.

3.3 Extracting Scattering and Absorption Coefficients from Reflectance Data

Model fits to experimental data were employed to extract wavelength-resolved absorption and scattering coefficients for each tissue type via Eqs. (1) and (2) and the formula for Mie scattering from cylinders. The results shown in FIGS. 2A and 2B represent a measurement of absorption and scattering coefficients of human pancreatic tissues.

As shown in FIGS. 2A and 2B, wavelength-resolved scattering (FIG. 2A) and absorption (FIG. 2B) coefficients of normal pancreatic tissue (solid lines) 120, pancreatic adenocarcinoma (dashed lines) 116, and pancreatitis (dotted lines) 114, extracted from representative fits of experimental data to the reflectance model. The difference in shape of the adenocarcinoma scattering coefficient can be attributed to the modeling of the adenocarcinoma cellular nuclear diameter and refractive index as being different from those of normal pancreatic tissue and pancreatitis.

The values of the coefficients in FIGS. 2A and 2B are in the range expected for gastrointestinal tissue. K. Vishwanath and M.-A. Mycek, "Do fluorescence decays remitted from tissues accurately reflect intrinsic fluorophore lifetimes?" Opt. Lett. 29, 1512-1514 (2004). Since the absorption coefficient can yield quantitative information about the blood content of the tissue, the mathematical model has the potential to be useful for in vivo studies, in which the presence of blood will likely be more significant.

4. Extracting and Modeling Intrinsic Fluorescence: Theory and Results 4.1 Correcting Fluorescence Data for Scattering- and Absorption-Related Artifacts Once the fits of the reflectance model to the adenocarcinoma and pancreatitis data were obtained, the extracted wavelength-resolved scattering coefficients $\mu_s(\lambda)$ (FIG. 2A) were then used to remove artifacts of scattering and absorption from the measured fluorescence spectra of normal, pancreatitis and adenocarcinoma tissue. To perform this task, a separate Beer-Lambert attenuation factor was constructed for each tissue type by using the extracted $\mu_s(\lambda)$ and $\mu_a(\lambda)$ values specific to that tissue type. The intrinsic fluorescence spectrum $F_{INTRINSIC}(\lambda)$ was then extracted according to the equation:

$$F_{INTRINSIC}(\lambda) = F_{MEAS}(\lambda)\exp([\mu_a(\lambda)+\mu_s'(\lambda)]z). \qquad (6)$$

The variable z represents the average depth that photons will travel in the tissue, and it was estimated from time-resolved Monte Carlo simulations [K. Vishwanath, and M.-A. Mycek, "Time-resolved photon migration in bi-layered tissue models," Opt. Express 13(19), 7466-7482 (2005).] to be 0.064 cm for all tissue types. To obtain this value, time-resolved Monte Carlo simulations were run for pancreatic tissue models whose absorption and scattering coefficients were representative of those shown in FIGS. 2A and 2B. The average depth of photon travel was determined by finding the time at which the greatest number of simulated photons exited the tissue, multiplying that by the speed of light in the medium, and dividing by two to account for the photons' travel back to the surface once they reached their point of greatest depth in the tissue.

4.2 Fitting Intrinsic Fluorescence to Endogenous Fluorophore Component Spectra

Once the intrinsic fluorescence spectra were obtained for each tissue type, their lineshapes could be decomposed into the component spectra of collagen, NADH, and FAD, three principal contributors to tissue autofluorescence in the 400-700 nm wavelength range. For each tissue type, the intrinsic fluorescence spectrum was fit to a linear combination (BasisFit($\lambda$)) of experimentally measured basis spectra of collagen, NADH, and FAD:

$$\text{BasisFit}(\lambda) = C_{COLLAGEN} F_{COLLAGEN}(\lambda) + C_{NADH} F_{NADH}(\lambda) + C_{FAD} F_{FAD}(\lambda). \quad (7)$$

To fit the intrinsic fluorescence spectra (FIGS. 3A, 3B and 3C) to Eq. (7), each of the basis spectra ($F_{COLLAGEN}(\lambda)$, $F_{NADH}(\lambda)$, and $F_{FAD}(\lambda)$) was blue-shifted by about 12 nm, which accounted for the fact that the component spectra were measured in various chemical solvents and not within a biological tissue environment.

FIGS. 3A, 3B and 3C illustrate intrinsic fluorescence spectra (solid lines) of normal pancreatic tissue 220 (FIG. 3A), pancreatitis (FIG. 3B) 214, and pancreatic adenocarcinoma 216 (FIG. 3C), shown with a representative fit to a linear combination 222 (dotted lines) with residuals 218 (small dotted line) of measured and blue-shifted collagen, NADH, and FAD basis spectra.

The deviation of the basis fits to the intrinsic fluorescence spectra of normal pancreatic tissue and pancreatitis around 600 nm may be attributed to the fact that the model does not include porphyrin fluorescence, which is known to peak around 635 nm when excited with 380-440 nm light. P. Hillemanns, et al., "Lymph node metastasis detection of ovarian cancer by porphyrin fluorescence photodetection: case report," Lasers Med. Sci. 22, 131-135 (2007).

The purpose of the fluorescence model was not to obtain an exact fit to every point on the intrinsic fluorescence spectra, but rather to interpret key features of the fluorescence from normal pancreatic tissue, pancreatitis, and pancreatic adenocarcinoma. Since the spectra were normalized to the peak, the intrinsic fluorescence between 500 and 550 nm (where intracellular NADH and FAD emit prominently) is expected to decrease in pancreatitis and adenocarcinoma, where there is increased extracellular stromal collagen content. In this diagnostically-relevant region, the error in fit between Eq. (7) and the intrinsic fluorescence was less than 4% for normal pancreatic tissue and pancreatitis, and less than 8% for adenocarcinoma.

The data from FIGS. 3A, 3B and 3C shows that the mathematical model of intrinsic fluorescence agreed well with histology of tissue samples from patients involved in the study and described in Table 1. The values of the collagen fit coefficients $C_{COLLAGEN}$ (Table 2) correlated well with the amount of collagen incursion amidst the cells in the tissue samples examined via histology.

TABLE 2

Fit coefficients Ci (percentage contributions) for collagen, NADH, and FAD basis spectra to intrinsic fluorescence spectra of normal pancreatic tissue, pancreatitis, and pancreatic adenocarcinoma.

|  | Normal | Pancreatitis | Adenocarcinoma |
| --- | --- | --- | --- |
| $C_{COLLAGEN}$ | 0.6 (35%) | 0.9 (56%) | 0.9 (82%) |
| $C_{NADH}$ | 0.8 (47%) | 0.3 (19%) | 0.1 (9%) |
| $C_{FAD}$ | 0.3 (18%) | 0.4 (25%) | 0.1 (9%) |

The data in FIGS. 3A, 3B and 3C were also compared to the intrinsic fluorescence extracted from a fluorescence spectrum obtained in vivo from a pancreatic adenocarcinoma xenograft in a NOD/SCID mouse. M. Chandra, et al., "Probing pancreatic disease using tissue optical spectroscopy," J. Biomed. Opt. 12, 060501 (2007). Mathematical modeling showed that the xenograft fluorescence could be mostly attributed to intracellular components, a conclusion that made sense given that the xenograft tumor was predominantly comprised of cells.

5. Discussion and Conclusions 5.1 Overview of Mathematical Models Developed

In this illustration of embodiments of the invention, mathematical models of reflectance and intrinsic fluorescence were developed and employed to quantitatively describe the effects of key histologically-observed tissue parameters on the measured optical spectra of pancreatitis and pancreatic adenocarcinoma (relative to normal pancreatic tissue). An empirical mathematical model of reflectance was able to fit the prominent feature in the adenocarcinoma spectrum (increased amplitude from about 455 to about 525 nm, relative to normal pancreatic tissue) with less than 6% error. Fitting the reflectance model to the measured optical spectra enabled the extraction of wavelength-resolved absorption and scattering coefficients of human pancreatic tissues. Obtaining values for the optical coefficients is an important result, because knowledge of these coefficients is essential for accurate computational studies of photon migration in pancreatic tissue models. For example, one such computational method is Monte Carlo simulation, which is accurate throughout optical parameter space for modeling photon transport in biological tissue. L. Wang, et al., "MCML—Monte Carlo modeling of light transport in multi-layered tissues," Computer Methods and Programs in Biomedicine 47, 131-146 (1995); K. Vishwanath and M.-A. Mycek, "Time-resolved photon migration in bi-layered tissue models," Opt. Expr. 13, 7466-7482 (2005).

The optical scattering coefficients extracted from the reflectance fits were used to correct the measured fluorescence spectra in an algorithm that removed tissue absorption and scattering artifacts. The resulting "intrinsic" endogenous fluorescence spectra were fit to a linear combination of basis spectra from native tissue fluorophores (collagen, NADH, FAD) to obtain the relative contributions from both extracellular (collagen, about 400 to about 450 nm emission peak) and intracellular (NADH and FAD, about 500 nm to about 600 nm emission peak) autofluorescence for each tissue type. The relative contribution of collagen was found to be greater in the intrinsic fluorescence spectra of pancreatitis and adenocarcinoma. Since the spectra were normalized to the peak, the pancreatitis and adenocarcinoma spectra exhibited a decrease in amplitude in the about 500 to about 550 nm range, where NADH and FAD emission are prominent. These results were consistent with the increased collagen fibrosis seen in histology of pancreatitis and adenocarcinoma. T. Imamura, et al., "Quantitative analysis of collagen and collagen subtypes I, III, and V in human pancreatic cancer, tumor-associated chronic pancreatitis, and alcoholic chronic pancreatitis," Pancreas 11, 357-364 (1995); J. Koninger, et al., "Overexpressed Decorin in Pancreatic Cancer: Potential Tumor Growth Inhibition and Attenuation of Chemotherapeutic Action," Clin. Cancer Res. 10, 4776-4783 (2004).

5.2 Correlation of Optical Tissue Models with Histology

As seen in FIGS. 1A and 1B, FIGS. 3A, 3B and 3C, and Table 3, empirical models of reflectance and intrinsic fluorescence were able to quantitatively describe the differences between normal pancreatic tissue, adenocarcinoma, and pancreatitis in terms of histologically observed changes in biologically meaningful parameters. The reflectance spectra of cancerous tissue differed most noticeably from normal pancreatic tissue at around 500 nm, a change that could be quantitatively linked, via spherical Mie scattering, to larger cell nuclei in pancreatic adenocarcinoma. Subtle differences in the reflectance spectra at around 400 nm to about 425 nm and about 450 nm to about 550 nm were also found, via modeling of cylindrical Mie scattering, to correlate with the increased number of collagen fibers in both pancreatitis and cancer. These results agree with histology in that both pancreatitis and pancreatic adenocarcinoma are marked by greater collagen content than normal pancreatic tissue, but only adenocarcinoma is characterized by larger cell nuclei. R. H. Hruban, et al., "Pancreatic Intraepithelial Neoplasia: A New Nomenclature and Classification System for Pancreatic Duct Lesions," Am. J. Surg. Path. 25, 579-86 (2001); R. H. Hruban, et al., "An Illustrated Consensus on the Classification of Pancreatic Intraepithelial Neoplasia and Intraductal Papillary Mucinous Neoplasms," Am. J. Surg. Path. 28, 977-87 (2004).

5.3 Comparison of Empirical Reflectance Model with Diffusion Approximation

The empirical reflectance model was compared with the diffusion approximation, which is often employed to extract tissue absorption and scattering properties from experimentally measured tissue reflectance spectra. G. Zonios, et al., "Comparative evaluation of two simple diffuse reflectance models for biological tissue applications," Appl. Opt. 47, 4965-4973 (2008). When the reflectance fitting procedure was employed with a subset of the hemoglobin concentration and blood oxygen saturation ranges, the diffusion approximation model was noticeably less effective than the empirical model for fitting the adenocarcinoma reflectance spectrum. In the diagnostically-relevant wavelength range of 455-525 nm, the error in fit to the measured adenocarcinoma spectrum was less than 6% for the empirical model, but it rose to as high as 13% with the diffusion approximation model. These results were not surprising because the fiber-optic probe in this study had a source-detector separation of only about 660 μm. Using the scattering coefficients $\mu_s$ from FIGS. 1A and 1B and a value of 0.9 for the tissue anisotropy g, it can be shown that the source-detector separation of the probe was often smaller than $1/\mu_s(1-g)$. This condition causes the diffusion approximation to break down [30], but the empirical model is accurate in this regime. R. Reif, et al., "Analytical model of light reflectance for extraction of the optical properties in small volumes of turbid media," Appl. Opt. 46, 7317-7328 (2007).

5.4 Potential of Optical Spectroscopy to Fulfill Unmet Clinical Need

Current methods to detect pancreatic adenocarcinoma are highly invasive and fail to find the disease early or to distin-

TABLE 3

Prominent disease-related changes in histology features and measured optical spectra of pancreatic tissues, along with corresponding changes made to mathematical models of reflectance and fluorescence.

| Pancreatic tissue | Adenocarcinoma | Pancreatitis |
| --- | --- | --- |
| Key histological features (relative to normal pancreatic tissue) | Increased nuclear size Greater stromal collagen content | Greater stromal collagen content |
| Optical signature (relative to normal pancreatic tissue) | Increased amplitude of reflectance spectrum from 455 to 525 nm<br>Spectral lineshape change in intrinsic fluorescence spectrum from 500 to 550 nm | Spectral lineshape change in intrinsic fluorescence spectrum from 500 to 550 nm |
| Mathematically modeled by | Multiplying spherical scatterer diameter $L_o$ by 1.33 for reflectance model<br>Increasing percentage contribution of collagen basis spectrum from 35% to 82% in fit to intrinsic fluorescence | Increasing percentage contribution of collagen basis spectrum from 35% to 56% in fit to intrinsic fluorescence |
| Mean error in fit of model to experimentally measured data in diagnostically relevant region | Less than 6% from 455 to 525 nm for adenocarcinoma reflectance model<br>Less than 8% from 500 to 550 nm for all intrinsic fluorescence models | Less than 4% from 500 to 550 nm for all intrinsic fluorescence models |

The intrinsic fluorescence model showed that for both pancreatitis and adenocarcinoma, there was an increased contribution from the collagen in the stroma, relative to normal pancreatic tissues. This result is consistent with the histological observation that the change from normal pancreatic tissue to both pancreatitis and adenocarcinoma is characterized by increased collagen amidst the cells. However, the intrinsic fluorescence spectra of pancreatitis and cancer were also shown to be different from each other. Whereas the reflectance model was most useful for discriminating pancreatic adenocarcinoma from pancreatitis, the intrinsic fluorescence model was more effective at distinguishing between all three tissue types. In any case, the use of the reflectance data to extract the intrinsic fluorescence lends credence to the idea that combining reflectance and fluorescence spectroscopy has a diagnostic advantage over using just one of these modalities to detect pancreatic cancer.

guish it from inflammation (pancreatitis). Hence, there is great biomedical need for an endoscopic screening procedure for early detection of pancreatic adenocarcinoma. Bimodal reflectance and fluorescence spectroscopy is a potential inroad into addressing this unmet clinical need. In this study, mathematical models of measured reflectance and fluorescence spectra were employed to quantitatively describe differences between normal pancreatic tissue, pancreatic adenocarcinoma, and pancreatitis. By using biomedically relevant parameters, the model provided a link between the results of optical spectroscopy and histology. Features in the reflectance spectra were quantitatively linked to larger cell nuclei in cancer and increased collagen content in both cancer and pancreatitis. The intrinsic fluorescence spectra were fit to a linear combination of collagen, NADH, and FAD basis spectra to show quantitative differences in the contribution of collagen to the measured fluorescence from normal pancreatic tissue, pancreatic adenocarcinoma, and pancreatitis.

Translation to an in vivo setting is feasible because the model can extract the optical absorption coefficient from increased blood content in the tissues. Challenges associated with obtaining an accurate reflectance fit near 425 and 550 nm (where hemoglobin absorption is noticeable) can be resolved by fitting each individual reflectance spectrum to an empirical equation, a photon migration model, or the $P_3$ approximation. M. Muller, et al., "Intrinsic fluorescence spectroscopy in turbid media: disentangling effects of scattering and absorption," Appl. Opt. 40, 4633-4646 (2001); G. M. Palmer and N. Ramanujam, "Monte-Carlo-based model for the extraction of intrinsic fluorescence from turbid media," J. Biomed. Opt. 13, 024017 (2008); J. C. Finlay and T. H. Foster, "Hemoglobin oxygen saturations in phantoms and in vivo from measurements of steady-state diffuse reflectance at a single, short source-detector separation," Med. Phys. 31, 1949-1959 (2004). Another test of the model could involve comparing the intrinsic fluorescence extracted via a Beer-Lambert factor (Eq. (6)) with that obtained with a more detailed photon migration model.

5.5 Illustration 1 Conclusions

The mathematical models of reflectance and fluorescence as discussed herein are useful tools for pancreatic cancer diagnostics because of their ability to quantitatively link the experimental results of optical spectroscopy with those of histopathology. The mathematical model of reflectance is able to quantitatively describe the reflectance spectra of normal pancreatic tissue, pancreatitis, and pancreatic adenocarcinoma in terms of biomedically relevant parameters. The algorithm to model the reflectance was rapid, taking only several seconds to execute. Furthermore, the concept of scaling an average measured normal pancreatic tissue reflectance spectrum to obtain the pancreatitis and adenocarcinoma spectra was found to be helpful with data interpretation due to its intuitive nature. FIGS. 2A and 2B show, among other things, the capability of the reflectance model to extract absorption and scattering coefficients of the aforementioned human pancreatic tissue types. When the fluorescence was corrected for attenuation artifacts (as shown in FIGS. 3A, 3B and 3C), the resulting intrinsic fluorescence spectra revealed differences in collagen content that correlated with histology as shown in Table 2. The, rapid, intuitive, and biomedically relevant nature of these mathematical models suggests that the data analysis procedure outlined herein may be of potential use not only for pancreatic cancer detection, but also for other optical diagnostic applications involving a wider range of biological tissues.

Illustration II

1. Introduction

In other embodiments, four tissue classification algorithms were developed to employ reflectance and fluorescence spectroscopy for differentiating between human pancreatic adenocarcinoma and pancreatitis tissue.

The first approach employed the ratio of measured reflectance at 470 nm to that at 650 nm and wavelength integrated fluorescence intensity (i.e., area under the curve) for tissue classification (i.e., SpARC—Spectral areas and ratios classifier) using Linear Discriminant Analysis (LDA), among other things.

The second was a chemometric approach that employed Principal Component Analysis (PCA) and Linear Discriminant analysis (LDA). In some embodiments, PCA was used to identify the diagnostic features in the spectra and then LDA was employed to classify the data based on these features.

The third method employed a photon-tissue interaction (PTI) model of photon transport in pancreatic tissue, previously developed by the inventors. R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009). The PTI model has been shown to be a relatively accurate means of quantitatively describing key changes in the reflectance and fluorescence spectra of adenocarcinoma and pancreatitis (relative to normal pancreatic tissue). In some embodiments, the quantitative parameters extracted from the model were used to classify tissue using LDA.

The fourth approach was a hybrid model that employed a combination of the chemometric, PTI model and SpARC algorithms.

For purposes of illustrating embodiments of the invention, further exemplary systems and methods of the invention are discussed herein below.

2. Methods 2.1 Human Studies

Reflectance and fluorescence spectra were measured from freshly excised pancreatic tissue obtained during Whipple procedures. Multiple sites were measured on tissues obtained from 12 patients within 30 minutes of excision. A total of 90 sites were measured from all the patients and two measurements were made on each site. After data acquisition from each measurement site, a portion of tissue was removed to link optical measurements with histological analysis.

2.2 Instrumentation

As in the prior example, a clinically compatible, fiber-optic coupled Reflectance and Fluorescence Lifetime Spectrometer (RFLS) was employed for data acquisition. M. Chandra, et al., "Probing pancreatic disease using tissue optical spectroscopy," J Biomed Opt 12, 060501 (2007); M. Chandra, et al., "Quantitative molecular sensing in biological tissues: an approach to non-invasive optical characterization," Optics Express 14, 6157-6171 (2006).

FIG. 5 provides a schematic of a system 10 constructed in accordance with some embodiments of the invention. It should be understood that system 10 components may be separate and in wired or wireless communication with one another. Alternatively, all or most of the components of system 10 may be combined as one instrument. System 10 includes a fluorescence excitation source 26 and a reflectance source 28 which are optically coupled with a probe 30 via independent fibers 32 and 34, respectively, for the communication of light therein. Fluorescence excitation source 26 may be, for example, a pulsed solid state diode laser emitting at 355 nm (e.g., PNV001525-140, JDS Uniphase, San Jose, Calif.) or like device, and reflectance source 28 may be, for example, a tungsten halogen lamp (e.g., HL 2000FHSA, Ocean Optics, Dunedin, Fla.), with a range of 360-2000 nm emission, or like device. Light delivered by fibers 32 and 34 is directed by probe 30 onto tissue 36 to produce one or more measurable spectroscopic responses, which in this embodiment includes reflectance and/or emitted fluorescence photons. Reflectance and emitted fluorescence photons from tissue 36 are delivered via a third fiber 38 disposed in probe 30 and in communication with one or more devices configured for measuring the spectroscopic response. In this embodiment, fiber 38 is in communication with a spectrograph 40 (e.g., MS 125, Oriel Instruments, Stratford, Conn.) or like device for measuring the properties of light and an avalanche photodiode 42 or other photodetector capable of time-resolved spectroscopic measurements, such as time-resolved fluorescence decay. As shown in FIG. 5, fiber 38 is divided so that a first portion of the detected photons is directed to spectrograph 40 and a second portion is directed to avalanche diode 42. In some embodiments, the division of fiber 38 is facilitated by a splitter or filter, such as a neutral density filter.

Spectrograph 40 may also include or be coupled with an intensified charge coupled device (ICCD) camera (e.g., ICCD 2063, Andor Technology, Belfast, Northern Ireland) or like device. Fibers 32, 34 and 36 may comprise 600 µm core optical fibers, although other sized fibers may be used. Alternatively, another material capable of delivering light as described above may be employed. System 10 further includes a data processing system 44 for analyzing the spectral data in accordance with the methods of the invention. For example, the data processing system 44 may be configured to compare the spectral data with the preset criteria, determine whether any preset criteria relating to a condition of tissue 36 is satisfied based on the spectral data, and classify tissue 36 accordingly based on the preset criteria satisfied. Data processing system 44 may also include a display for presenting the results of the analysis, which may be particularly useful when using system 10 during a biopsy or endoscopic procedure.

FIG. 6 illustrates an embodiment of probe 30 according the invention in which fibers 32, 34 and 36 are disposed adjacently in a substantially triangular cross sectional arrangement at distal end 44 of probe 30. It should be readily apparent that more or less fibers in a variety of arrangements may be employed in probe 30. For example, one fiber may be used or a ring of four or more fibers maybe fitted in probe 30. In operation, fluorescence and reflectance excitation of tissue 36 and measurements can be obtained using probe 30 by sequentially blocking light from fiber 32 and 34 using shutters (not shown) or some other apparatus for alternatively covering one fiber at a time while leaving fiber 36 exposed for the detection of tissue fluorescence and reflectance.

Those skilled in the art will readily appreciate that methods and systems of the embodiments of the invention, such as system 10, may include various other elements, such as electrical or optical components, lasers, lamps, oscilloscopes, connectors, connector blocks, relays, pulse conditioners, generators, etc., computer and network related software and hardware, such as programs, operating systems, memory storage devices, input/output devices, processors, servers, data communication links, whether wireless or otherwise, and data transceiving devices. Those skilled in the art will further appreciate that it is within the scope of the invention to include such additional elements and identifying precise types of components is not vital to the full implementation of the systems and methods of the invention.

The acquired fluorescence spectra were corrected for spectral instrument response after background correction. The reflectance spectra were also background subtracted and then scaled by the lamp reflectance spectrum ($R_o$) to obtain the corrected reflectance spectra ($R/R_o$). All spectra were normalized by scaling the peak intensity value to unity.

2.3 Pathology and Inclusion Criterion

Pathology indicated that of the measured sites 17 were adenocarcinoma sites, 22 were pancreatitis sites, and 11 were normal tissue sites. The rest of the sites were either malignant breast cancer that had metastasized to the pancreas (10 sites), intraductal papillary mucinous neoplasm (IPMN—8 sites), pancreatic intraepithelial neoplasia (PanIN—6 sites), serous cyst adenoma (SCA—8 sites), scar or fat tissue or both (5 sites) or a hybrid tissue site having two or more of the above mentioned pathologies (3 sites). These sites were excluded from the data set used for algorithm development. Furthermore, those measurements that were very noisy were also excluded from the data set (4 measurements).

This left a total of 33 adenocarcinoma measurements, 40 pancreatitis measurements, and 22 normal measurements of both fluorescence and reflectance spectra. Tissue algorithm development was undertaken with this set of data of 95 total spectra (Set 1) of both fluorescence and reflectance spectra.

A second set (Set 2) of data was analyzed separately in which six of the pancreatitis sites from patient 10 were also excluded owing to some discrepancy with pathology results. Thus Set 2 comprised of 33 adenocarcinoma measurements, 31 pancreatitis measurements, and 22 normal measurements (86 total spectra) of both fluorescence and reflectance spectra each.

Table 4 shown below indicates the pathology of the measured sites for each patient. The sites with asterisks were included in algorithm development as indicated below while sites without asterisks were excluded.

TABLE 4

Patient-wise histology of the sites from which data was collected

| Patient | N | P | A | PanIN | IPMN | SCA | MBC | Scar/fat/both | P and A[a] | N and A[b] |
|---|---|---|---|---|---|---|---|---|---|---|
| 1 | 2* | 3* | — | — | — | — | — | — | — | — |
| 2 | — | — | 5* | — | — | — | — | — | — | — |
| 3 | — | 5* | — | 1 | — | — | — | 1 | 1 | — |
| 4 | — | 3* | — | — | 1 | — | — | 1 | — | — |
| 5 | — | — | — | — | — | 8 | — | — | — | — |
| 6 | 4* | — | — | 1 | — | — | — | — | — | — |
| 7 | — | — | — | — | 7 | — | — | 1 | — | — |
| 8 | — | 4* | 1* | 1 | — | — | — | — | 1 | 1 |
| 9 | 5* | 1* | 1* | 3 | — | — | — | — | — | — |
| 10 | — | 6** | — | — | — | — | — | 2 | — | — |
| 11 | — | — | 10* | — | — | — | — | — | — | — |
| 12 | — | — | — | — | — | — | 10 | — | — | — |

N: Normal;
P: Pancreatitis;
A: Adenocarcinoma;
PanIN: Pancreatic Intraepithelial Neoplasia;
SCA: Serous Cyst Adenoma;
MBC: metastatic breast carcinoma case
[a] A hybrid tissue site of chronic pancreatitis and adenocarcinoma;
[b] A hybrid tissue site of focal adenocarcinoma at the edge of mostly normal tissue
*These sites were included in the data.
**These sites were both included and excluded from the data for algorithm development

2.4 Leave-One-Out Cross-Validation

A leave-one-out cross-validation was undertaken to test the performance of each of the proposed tissue classification algorithms. For each algorithm, the data were divided into Training and Test data where each spectrum was considered as Test data one at a time, while the remaining spectra were treated as Training data. Thus, each algorithm was implemented 95 times for Set 1 and 86 times for Set 2. Data sensitivity, specificity, positive predictive value (PPV) and negative predictive value (NPV) were calculated.

2.5 Spectral Areas and Ratios Classifier (SpARC) Algorithm

Preliminary examination of the fluorescence and reflectance spectra from a pilot study conducted by us had suggested the use of the ratio of measured Reflectance at 470 nm to that at 650 nm ($R_{ratio}=R_{470}/R_{650}$) and the wavelength integrated fluorescence (area under the curve) as possible tissue classifiers.

The ratio $R_{ratio}=R_{470}/R_{650}$ was calculated for each measured reflectance spectrum and the wavelength integrated fluorescence ($F_{area}$) was calculated for each of the fluorescence spectra. The test data was classified in a two-step procedure where $R_{ratio}$ was first employed to identify adenocarcinoma using LDA on the training data. If the tissue was classified as not adenocarcinoma then $R_{ratio}$ and $F_{area}$ were both employed to classify the test data as either pancreatitis or normal using LDA. The process was repeated for each of the spectra in data Set 1 and data Set 2 (as discussed in the section above regarding "leave-one-out cross-validation").

For purposes of illustrating some embodiments of the invention, exemplary chemometric analysis of the spectra is discussed in further detail below.

2.6 Chemometric Analysis of the Spectra

2.6.1 Principal Component Analysis (PCA)

PCA was employed to express each spectrum as a linear combination of a set of orthogonal basis vectors (or components). A. D. Joshi, et al., "Improving PET receptor binding estimates from Logan plots using principal component analysis," J Cerebr Blood F Met 28, 852-865 (2008). Of these components, the key-features of the data are captured by only a few vectors with high eigenvalues while the vectors corresponding to lower eigenvalues represent noise in the data. However, not all the key features of the spectra are diagnostically relevant (i.e., enabling differentiation between the tissue types). By identifying the few diagnostically relevant components, the dimensionality of the problem is reduced. The diagnostically relevant components are identified by fitting the principal components to the spectra. The components whose coefficients showed greatest difference between tissue types were identified as diagnostically relevant.

The training data spectra $\bar{s}_i \in R^{n \times 1}$ (i=1 to m) for different tissue types were grouped together and arranged row-wise in a matrix $S \in R^{m \times n}$ as shown below:

$$S = \begin{bmatrix} \bar{s}_1^T \\ \bar{s}_2^T \\ \vdots \\ \bar{s}_m^T \end{bmatrix} = \begin{bmatrix} \bar{s}_1^T \\ \vdots \\ \bar{s}_p^T \\ \vdots \\ \bar{s}_{p+q}^T \\ \vdots \\ \bar{s}_{p+q+r}^T \end{bmatrix}, \quad (8)$$

where, p, q and r (p+q+r=m) are the number of spectra for adenocarcinoma, pancreatitis and normal tissue type respectively. Using PCA, the above shown n dimensional training set (corresponding to the n measured wavelengths) with m total spectra can be represented as a linear combination of n basis vectors as shown below:

$$S^T = CX, \quad (9)$$

where, $^T$ is the transpose operator, $C \in R^{n \times n}$ is the matrix of the n principal components, and X is a matrix of the fit coefficients.

$$X = \begin{bmatrix} x_{11} & x_{12} & \cdots & x_{1m} \\ x_{21} & \ddots & & \vdots \\ \vdots & & \ddots & \\ x_{n1} & \cdots & \cdots & \cdots & x_{nm} \end{bmatrix}, \quad (10)$$

Where, an element $x_{ji}$ is the fit-coefficient of the $j^{th}$ component for the $i^{th}$ spectrum.

The principal component matrix C was obtained from S by employing the princomp function in MATLAB. The princomp function first calculates matrix $S_0$ by subtracting the column mean vector from each row of S. Then singular value decomposition is used to calculate the principal components as the eigenvectors of the sample covariance matrix $$\left( \frac{1}{m-1} S_0^T S_0 \right).$$

The columns of X were estimated by fitting the principal components to the spectra using ordinary least squares. The estimated coefficients vectors for each spectrum (i.e. the columns of X) were then separated into three groups based on the tissue type. The principal components for which the coefficients were significantly different between the tissue types were determined based on pair-wise student's T-test (p<0.05). Six such t-tests were performed for the coefficients of each principal component j: The hypothesis tested was that the mean fit-coefficients were significantly different for the jth principal component of (1) Adenocarcinoma and the rest of the tissue types, (2) Normal and the rest of the tissue types, (3) Pancreatitis and the rest of the tissue types, (4) adenocarcinoma and Pancreatitis, (5) Adenocarcinoma and Normal, (6) Pancreatitis and Normal. These principal components were the diagnostically relevant components.

The above analysis was done for both fluorescence (n=492) and reflectance spectra (n=521) separately to determine the components whose coefficients would be used for classification of tissue types in the test data.

Thus, in some embodiments, the steps involved in the algorithm development include: obtaining fluorescence or reflectance spectra at n or a plurality of wavelengths; apply principal component analysis to calculate n or a plurality of components; T-test compares the fit coefficients of each of the n components for each tissue type, that is, tissue with adenocarcinoma, normal tissue or pancreatitis tissue and identifies which components are significant for classifying the tissue types.

2.6.2 Classification of Test Data Using PCA and LDA

Each fluorescence and reflectance spectrum of the test data were then fit to the principal components obtained above (C) and the coefficients of the components that were identified as being diagnostically relevant were used for classifying the test data by employing Linear discriminant analysis (LDA). Z. F. Ge, et al., "Identification of colonic dysplasia and neoplasia by diffuse reflectance spectroscopy and pattern recognition techniques," Applied Spectroscopy 52, 833-839 (1998). The analysis was done by employing the coefficients of a varying number of diagnostically relevant components.

This analysis was repeated for each measured spectrum for leave-one-out cross-validation as described above.

2.8 Hybrid Algorithm: Combination of the Chemometric, PTI Model, and SpARC Algorithms It has been previously shown that a "hybrid" between a pure chemometric model (e.g. PCA) and a physical tissue model can produce increased diagnostic accuracy. Z. Volynskaya, et al., "Diagnosing breast cancer using diffuse reflectance spectroscopy and intrinsic fluorescence spectroscopy," J Biomed Opt 13, 024012 (2008). A hybrid algorithm employing the parameters extracted from the SpARC algorithm, the chemometric approach, and the physical photon-tissue interaction (PTI) model, was used to classify tissue spectra. LDA was employed to this multi-dimensional classification criterion to achieve tissue classification using a leave-one-out cross-validation. The data was divided into Training and Test data using a leave-one-out method. The classifiers corresponding to SpARC, Chemometric and PTI model algorithms were calculated for each of the Training set data and the Test data.

The SpARC algorithm as discussed above was employed to calculate the ratio of reflectance intensities at 470 nm to that at 650 nm ($R_{ratio}=R_{470}/R_{650}$) for each reflectance spectrum and the wavelength integrated fluorescence intensity ($F_{area}$) for each fluorescence spectrum.

The Chemometric algorithm as discussed above was employed to identify the diagnostically relevant principal components (PC) of reflectance and fluorescence spectra in the training set for identifying adenocarcinoma from the rest ($RPC_A$ and $FPC_A$) and for identifying between pancreatitis and normal tissue ($RPC_{P-N}$ and $FPC_{P-N}$).

Once these parameters were extracted, Linear Discriminant Analysis was first employed to classify the Test data as either adenocarcinoma or not adenocarcinoma using all or a subset of L/Lo, $C_{coll}$, $C_{NADH}+C_{FAD}$, $R_{ratio}$, $F_{area}$, and fit-coefficients of $RPC_A$ and $FPC_A$.

Then, if the data was classified as not cancer, LDA employed all or a subset of L/Lo, $C_{coll}$, $C_{NADH}+C_{FAD}$, $R_{ratio}$, $F_{area}$, and fit-coefficients of $RPC_{P-N}$ and $FPC_{P-N}$ to classify the Test data as either pancreatitis or normal tissue type.

This process was repeated in a leave-one-out cross-validation scheme to calculate sensitivity, specificity, PPV and NPV.

2.9 Principal Component Analysis (PCA) of Time-Resolved Fluorescence Data

PCA was employed as described above on the time-resolved fluorescence data acquired from adenocarcinoma, pancreatitis, and normal tissue. The acquired decay traces were smoothed and normalized and the principal components were calculated for the training data. The t-test on the fit-coefficients of each principal component indicated that pancreatitis and normal tissue can be discriminated by using the PCA of time-resolved data.

The analysis was done for distinguishing Pancreatitis from Normal tissue using a leave-one-out cross-validation on data Set 1 and data Set 2 excluding patient 11 data. Data from patient 1 to 10 were collected by measuring the entire spectrum. The data from patient 11 onwards was excluded as it was obtained with a long-pass filter (>500 nm) in front of the avalanche photodiode (thus capturing only a portion of the spectrum). The results are discussed herein below.

3. Results 3.1 SpARC Algorithm for Tissue Classification

Classification of data Set 1 and Set 2 was achieved by using either only $R_{ratio}$ as a classifier (Table 5, Table 6), or only $F_{area}$ as a classifier (Table 7, and Table 8) or a combination of the two (Table 9 and Table 10). The tables list the sensitivity, specificity, PPV, and NPV of the SpARC algorithm in classifying (a) adenocarcinoma from pancreatitis and normal tissue, (b) adenocarcinoma from pancreatitis tissue, (c) adenocarcinoma from normal tissue, (d) pancreatitis from normal tissue and adenocarcinoma tissue (e) normal from adenocarcinoma and pancreatitis tissue. The classification in Tables 9 and 10 was undertaken by first employing $R_{ratio}$ to identify adenocarcinoma and then employing $R_{ratio}$ and $F_{area}$ to distinguish between pancreatitis and normal tissue types. $F_{area}$ was not employed for adenocarcinoma classification as it decreased the classification performance of the algorithm.

TABLE 5

Employing only $R_{ratio}$ for data Set 1 classification

| Tissue Type | Sensitivity (%) | Specificity (%) | PPV (%) | NPV (%) |
|---|---|---|---|---|
| A vs. P and N | 84.8 | 85.5 | 75.7 | 91.4 |
| P vs. A and N | 35.0 | 87.3 | 66.7 | 64.9 |
| N vs. A and P | 81.8 | 74.0 | 48.6 | 93.1 |
| A vs. P | 84.8 | 85.0 | 82.4 | 87.2 |
| A vs. N | 87.9 | 95.5 | 96.7 | 84.0 |
| P vs. N | 57.5 | 81.8 | 85.2 | 51.4 |

N: Normal;
P: Pancreatitis;
A: Adenocarcinoma

TABLE 6

Employing only $R_{ratio}$ for data Set 2 classification

| Tissue Type | Sensitivity (%) | Specificity (%) | PPV (%) | NPV (%) |
|---|---|---|---|---|
| A vs. P and N | 87.9 | 88.7 | 82.9 | 92.2 |
| P vs. A and N | 35.5 | 87.3 | 61.1 | 70.6 |
| N vs. A and P | 72.7 | 73.4 | 48.5 | 88.7 |
| A vs. P | 84.8 | 83.9 | 84.8 | 83.9 |
| A vs. N | 87.9 | 95.5 | 96.7 | 84.0 |
| P vs. N | 51.6 | 72.7 | 72.7 | 51.6 |

N: Normal;
P: Pancreatitis;
A: Adenocarcinoma

TABLE 7

Employing only $F_{area}$ for data Set 1 classification

| Tissue Type | Sensitivity (%) | Specificity (%) | PPV (%) | NPV (%) |
|---|---|---|---|---|
| A vs. P and N | 66.7 | 62.9 | 48.9 | 78.0 |
| P vs. A and N | 57.5 | 69.1 | 57.5 | 69.1 |
| N vs. A and P | 18.2 | 91.8 | 40.0 | 78.8 |
| A vs. P | 66.7 | 62.5 | 59.5 | 69.4 |
| A vs. N | 51.5 | 59.1 | 65.4 | 44.8 |
| P vs. N | 57.5 | 63.6 | 74.2 | 45.2 |

N: Normal;
P: Pancreatitis;
A: Adenocarcinoma

TABLE 8

Employing only $F_{area}$ for data Set 2 classification

| Tissue Type | Sensitivity (%) | Specificity (%) | PPV (%) | NPV (%) |
|---|---|---|---|---|
| A vs. P and N | 66.7 | 60.4 | 51.2 | 74.4 |
| P vs. A and N | 54.8 | 67.3 | 48.6 | 72.5 |
| N vs. A and P | 13.6 | 92.2 | 37.5 | 75.6 |

TABLE 8-continued

Employing only $F_{area}$ for data Set 2 classification

| Tissue Type | Sensitivity (%) | Specificity (%) | PPV (%) | NPV (%) |
|---|---|---|---|---|
| A vs. P | 66.7 | 58.1 | 62.9 | 62.1 |
| A vs. N | 51.5 | 59.1 | 65.4 | 44.8 |
| P vs. N | 54.8 | 59.1 | 65.4 | 48.1 |

N: Normal;
P: Pancreatitis;
A: Adenocarcinoma

TABLE 9

Performance of the SpARC algorithm for data Set 1

| Tissue Type | Sensitivity (%) | Specificity (%) | PPV (%) | NPV (%) |
|---|---|---|---|---|
| A vs. P and N | 84.8 | 85.5 | 75.7 | 91.4 |
| P vs. A and N | 50.0 | 83.6 | 69.0 | 69.7 |
| N vs. A and P | 72.7 | 82.2 | 55.2 | 90.9 |
| A vs. P | 84.8 | 85.0 | 82.4 | 87.2 |
| A vs. N | 87.9 | 95.5 | 96.7 | 84.0 |
| P vs. N | 70.0 | 72.7 | 82.4 | 57.1 |

N: Normal;
P: Pancreatitis;
A: Adenocarcinoma

TABLE 10

Performance of the SpARC algorithm for data Set 2

| Tissue Type | Sensitivity (%) | Specificity (%) | PPV (%) | NPV (%) |
|---|---|---|---|---|
| A vs. P and N | 87.9 | 88.7 | 82.9 | 92.2 |
| P vs. A and N | 51.6 | 87.3 | 69.6 | 76.2 |
| N vs. A and P | 72.7 | 81.3 | 57.1 | 89.7 |
| A vs. P | 84.8 | 83.9 | 84.8 | 83.9 |
| A vs. N | 87.9 | 95.5 | 96.7 | 84.0 |
| P vs. N | 64.5 | 72.7 | 76.9 | 59.3 |

N: Normal;
P: Pancreatitis;
A: Adenocarcinoma

3.2 Chemometric Classification

The t-tests performed as described above indicated that the principal components of the reflectance and fluorescence spectra that were diagnostically relevant for classifying Adenocarcinoma from Pancreatitis and Normal ($RPC_A$ and $FPC_A$) were not the same as for classifying Pancreatitis from Normal. This indicated that it may be necessary to separate the classification algorithm into a two-step process where first Adenocarcinoma sites are identified in the Test data and then the rest of the data is classified into Normal and Pancreatitis.

3.2.1 Classifying Adenocarcinoma Vs. Pancreatitis and Normal Tissue

Four diagnostically relevant principal components, two each from reflectance and fluorescence were identified by finding those components, in the first ten principal components, for which the t-test between adenocarcinoma and the remaining tissue types' fit-coefficents gave a p-value<0.05. LDA was then used to classify the test data into adenocarcinoma or not adenocarcinoma based on the fit-coefficient values for all or a subset of these four principal component values ($RPC_A1$, $RPC_A2$, $FPC_A1$, $FPC_A2$).

If a tissue type was classified as not adenocarcinoma in this part of the algorithm then it was classified as either normal or pancreatitis as described below.

3.2.2 Classifying Pancreatitis Vs. Normal Tissue

Four diagnostically relevant principal components, two each from reflectance and fluorescence were identified by finding those components, in the first ten principal components, for which the t-test between normal and pancreatitis fit-coefficients gave a p-value<0.05. LDA was then used to classify test data into normal and pancreatitis based on the fit-coefficient values for all or a subset of these four principal component values ($RPC_{P-N}1$, $RPC_{P-N}2$, $FPC_{P-N}1$, $FPC_{P-N}2$). The chemometric algorithm was validated by employing the leave-one-out technique.

Table 11 and Table 12 list the classification performance of the chemometric algorithm if only the fit-coefficients of diagnostically relevant reflectance principal components are employed for tissue classification ($RPC_A1$, $RPC_A2$, $RPC_{P-N}1$, $RPC_{P-N}2$).

Table 13 and Table 14 list the classification performance of the chemometric algorithm if only the fit-coefficients of diagnostically relevant principal components of the fluorescence spectra are employed for tissue classification ($FPC_A1$, $FPC_A2$, $FPC_{P-N}1$, $FPC_{P-N}2$). In Table 14 values are missing due to the absence of any diagnostically relevant, $FPC_{P-N}1$, $FPC_{P-N}2$ for distinguishing between normal and pancreatitis for certain Test data. This shows that chemometric analysis of fluorescence spectra could not be used alone for tissue classification.

Table 15 and Table 16 list the classification performance of the chemometric algorithm if the fit-coefficients of all diagnostically relevant principal components of reflectance and fluorescence spectra are employed for tissue classification ($RPC_A1$, $RPC_A2$, $FPC_A1$, $FPC_A2$, $RPC_{P-N}1$, $RPC_{P-N}2$, $FPC_{P-N}1$, and $FPC_{P-N}2$).

TABLE 11

Performance of the chemometric algorithm using Reflectance spectra only for data Set 1 ($RPC_A1$, $RPC_A2$, $RPC_{P-N}1$, $RPC_{P-N}2$)

| Tissue Type | Sensitivity (%) | Specificity (%) | PPV (%) | NPV (%) |
|---|---|---|---|---|
| A vs. P and N | 93.9 | 83.9 | 75.6 | 96.3 |
| P vs. A and N | 52.5 | 90.9 | 80.8 | 72.5 |
| N vs. A and P | 77.3 | 84.9 | 60.7 | 92.5 |
| A vs. P | 90.9 | 77.5 | 76.9 | 91.2 |
| A vs. N | 93.9 | 86.4 | 91.2 | 90.5 |
| P vs. N | 70.0 | 77.3 | 84.8 | 58.6 |

N: Normal;
P: Pancreatitis;
A: Adenocarcinoma

TABLE 12

Performance of the chemometric algorithm using Reflectance spectra only for data Set 2 ($RPC_A1$, $RPC_A2$, $RPC_{P-N}1$, $RPC_{P-N}2$)

| Tissue Type | Sensitivity (%) | Specificity (%) | PPV (%) | NPV (%) |
|---|---|---|---|---|
| A vs. P and N | 87.9 | 86.8 | 80.6 | 92.0 |
| P vs. A and N | 54.8 | 87.3 | 70.8 | 77.4 |
| N vs. A and P | 68.2 | 82.8 | 57.7 | 88.3 |
| A vs. P | 87.9 | 80.6 | 82.9 | 86.2 |
| A vs. N | 93.9 | 86.4 | 91.2 | 90.5 |
| P vs. N | 74.2 | 68.2 | 76.7 | 65.2 |

N: Normal;
P: Pancreatitis;
A: Adenocarcinoma

TABLE 13

Performance of the chemometric algorithm using Fluorescence spectra only for data Set 1 (FPC$_A$1, FPC$_A$2, FPC$_{P-N}$1, FPC$_{P-N}$2)

| Tissue Type | Sensitivity (%) | Specificity (%) | PPV (%) | NPV (%) |
|---|---|---|---|---|
| A vs. P and N | 78.8 | 82.3 | 70.3 | 87.9 |
| P vs. A and N | 32.5 | 78.2 | 52.0 | 61.4 |
| N vs. A and P | 50.0 | 69.9 | 33.3 | 82.3 |
| A vs. P | 78.8 | 80.0 | 76.5 | 82.1 |
| A vs. N | 81.8 | 81.8 | 87.1 | 75.0 |
| P vs. N | 42.5 | 54.5 | 63.0 | 34.3 |

N: Normal;
P: Pancreatitis;
A: Adenocarcinoma

TABLE 14

Performance of the chemometric algorithm using Fluorescence spectra only for data Set 2 (FPC$_A$1, FPC$_A$2, FPC$_{P-N}$1, FPC$_{P-N}$2)

| Tissue Type | Sensitivity (%) | Specificity (%) | PPV (%) | NPV (%) |
|---|---|---|---|---|
| A vs. P and N | 69.7 | 81.1 | 69.7 | 81.1 |
| P vs. A and N | * | * | * | * |
| N vs. A and P | * | * | * | * |
| A vs. P | 69.7 | 77.4 | 76.7 | 70.6 |
| A vs. N | 72.7 | 77.3 | 82.8 | 65.4 |
| P vs. N | * | * | * | * |

N: Normal;
P: Pancreatitis;
A: Adenocarcinoma;
* No significant PC for classification

TABLE 15

Performance of the chemometric algorithm for data Set 1 Employing RPC$_A$1, RPC$_A$2, FPC$_A$1, FPC$_A$2, RPC$_{P-N}$1, RPC$_{P-N}$2, FPC$_{P-N}$1, and FPC$_{P-N}$2

| Tissue Type | Sensitivity (%) | Specificity (%) | PPV (%) | NPV (%) |
|---|---|---|---|---|
| A vs. P and N | 90.9 | 83.9 | 75.0 | 94.5 |
| P vs. A and N | 52.5 | 87.3 | 75.0 | 71.6 |
| N vs. A and P | 63.6 | 82.2 | 51.9 | 88.2 |
| A vs. P | 87.9 | 82.5 | 80.6 | 89.2 |
| A vs. N | 93.9 | 85.7 | 91.2 | 90.0 |
| P vs. N | 67.5 | 63.6 | 77.1 | 51.9 |

N: Normal;
P: Pancreatitis;
A: Adenocarcinoma

TABLE 16

Performance of the chemometric algorithm for data Set 2 Employing RPC$_A$1, RPC$_A$2, FPC$_A$1, FPC$_A$2, RPC$_{P-N}$1, RPC$_{P-N}$2, FPC$_{P-N}$1, and FPC$_{P-N}$2

| Tissue Type | Sensitivity (%) | Specificity (%) | PPV (%) | NPV (%) |
|---|---|---|---|---|
| A vs. P and N | 87.9 | 88.7 | 82.9 | 92.2 |
| P vs. A and N | 58.1 | 85.5 | 69.2 | 78.3 |
| N vs. A and P | 63.6 | 82.8 | 56.0 | 86.9 |
| A vs. P | 87.9 | 87.1 | 87.9 | 87.1 |
| A vs. N | 93.9 | 86.4 | 91.2 | 90.5 |
| P vs. N | 71.0 | 63.6 | 73.3 | 60.9 |

N: Normal;
P: Pancreatitis;
A: Adenocarcinoma

Table 17 and Table 18 list the classification performance of the chemometric algorithm if the fit-coefficients of the following diagnostically relevant principal components of reflectance and fluorescence spectra are employed for tissue classification (RPC$_A$1, RPC$_A$2, FPC$_A$1, RPC$_{P-N}$1, RPC$_{P-N}$2, FPC$_{P-N}$1, and FPC$_{P-N}$2) i.e. FPC$_A$2 was not employed for adenocarcinoma classification. This algorithm showed the best adenocarcinoma classification.

TABLE 17

Performance of the chemometric algorithm for data Set 1 Employing RPC$_A$1, RPC$_A$2, FPC$_A$1, RPC$_{P-N}$1, RPC$_{P-N}$2, FPC$_{P-N}$1, and FPC$_{P-N}$2

| Tissue Type | Sensitivity (%) | Specificity (%) | PPV (%) | NPV (%) |
|---|---|---|---|---|
| A vs. P and N | 93.9 | 85.5 | 77.5 | 96.4 |
| P vs. A and N | 52.5 | 85.5 | 72.4 | 71.2 |
| N vs. A and P | 63.6 | 83.6 | 53.8 | 88.4 |
| A vs. P | 93.9 | 80.0 | 79.5 | 94.1 |
| A vs. N | 93.9 | 86.4 | 91.2 | 90.5 |
| P vs. N | 67.5 | 63.6 | 77.1 | 51.9 |

N: Normal;
P: Pancreatitis;
A: Adenocarcinoma

TABLE 18

Performance of the chemometric algorithm for data Set 2 Employing RPC$_A$1, RPC$_A$2, FPC$_A$1, RPC$_{P-N}$1, RPC$_{P-N}$2, FPC$_{P-N}$1, and FPC$_{P-N}$2

| Tissue Type | Sensitivity (%) | Specificity (%) | PPV (%) | NPV (%) |
|---|---|---|---|---|
| A vs. P and N | 93.9 | 88.7 | 83.8 | 95.9 |
| P vs. A and N | 54.8 | 87.3 | 70.8 | 77.4 |
| N vs. A and P | 63.6 | 82.8 | 56.0 | 86.9 |
| A vs. P | 90.9 | 87.1 | 88.2 | 90.0 |
| A vs. N | 93.9 | 86.4 | 91.2 | 90.5 |
| P vs. N | 71.0 | 63.6 | 73.3 | 60.9 |

N: Normal;
P: Pancreatitis;
A: Adenocarcinoma 3.4 Hybrid Algorithm for Tissue Classification: Combination of Chemometric, PTI Model and SpARC Algorithms.

The Hybrid algorithm was also a two-step algorithm that first identified a Test data as adenocarcinoma or not. If not, the data was then classified as either pancreatitis or normal.

FIG. 7 provides a flow chart 70 which illustrates, among other things, an example of the manner in which the hybrid algorithm can be employed to classify a pancreatic tissue site into normal, adenocarcinoma, or pancreatitis. In this example, a fiber optic probe, such as the probe discussed previously, delivers excitation light from the fluorescence and reflectance sources to the tissue site to produce a spectroscopic event. The fluorescence and reflectance signals, that is, the emitted reflectance spectrum (R(λ)), fluorescence spectrum (F(λ)), and time-resolved fluorescence decay (F(t)), are then collected by the probe and delivered to the detectors. The SpARC algorithm is employed to calculate the R$_{ratio}$ (=R$_{470}$/R$_{650}$) for the reflectance spectrum and the wavelength integrated fluorescence intensity (F$_{area}$) for the fluorescence spectrum. The Chemometric algorithm is then employed to calculate the fit-coefficients (α) for the diagnostically significant principal components (PC) of the reflectance and fluorescence spectra and time-resolved fluorescence decay. It should be noted that for each set of measurements of reflectance and fluorescence spectra, the PTI model algorithm extracted the parameters nuclear size (L/L$_o$), C$_{coll}$, C$_{NADH}$, and C$_{FAD}$. Linear Discriminant Analysis (LDA) is then employed to this multi-dimensional classification criterion to achieve tissue classification using a leave-one-out cross-validation.

Table 25 and Table 26 list the sensitivity, specificity, PPV, and NPV of the Hybrid algorithm in classifying pancreatic tissue (for data Set 1 and Set 2). In this case all the classifiers from SpARC (R$_{ratio}$ and F$_{area}$) and Chemometric (RPC$_A$1, RPC$_A$2, FPC$_A$1, FPC$_A$2, RPC$_{P-N}$1, RPC$_{P-N}$2, FPC$_{P-N}$1, and FPC$_{P-N}$2), and PTI model (L/Lo, C$_{coll}$, C$_{NADH}$+C$_{FAD}$) algorithms were employed for tissue classification. However, a sub-set of these classifiers could also be used.

TABLE 25

Performance of the Hybrid algorithm for data Set 1
All classifiers from Chemometric, PTI model and SpARC algorithm included

| Tissue Type | Sensitivity (%) | Specificity (%) | PPV (%) | NPV (%) |
| --- | --- | --- | --- | --- |
| A vs. P and N | 84.8 | 95.2 | 90.3 | 92.2 |
| P vs. A and N | 65.0 | 85.5 | 76.5 | 77.0 |
| N vs. A and P | 72.7 | 80.8 | 53.3 | 90.8 |
| A vs. P | 84.8 | 92.5 | 90.3 | 88.1 |
| A vs. N | 90.9 | 86.4 | 90.9 | 86.4 |
| N vs. P | 72.5 | 72.7 | 82.9 | 59.3 |

N: Normal;
P: Pancreatitis;
A: Adenocarcinoma

TABLE 26

Performance of the Hybrid algorithm for data Set 2
All classifiers from Chemometric, PTI model and SpARC algorithm included

| Tissue Type | Sensitivity (%) | Specificity (%) | PPV (%) | NPV (%) |
| --- | --- | --- | --- | --- |
| A vs. P and N | 87.9 | 92.5 | 87.9 | 92.5 |
| P vs. A and N | 48.4 | 87.3 | 68.2 | 75.0 |
| N vs. A and P | 68.2 | 75.0 | 48.4 | 87.3 |
| A vs. P | 84.8 | 87.1 | 87.5 | 84.4 |
| A vs. N | 87.9 | 81.8 | 87.9 | 81.8 |
| N vs. P | 58.1 | 68.2 | 72.0 | 53.6 |

N: Normal;
P: Pancreatitis;
A: Adenocarcinoma

Figure 4A:
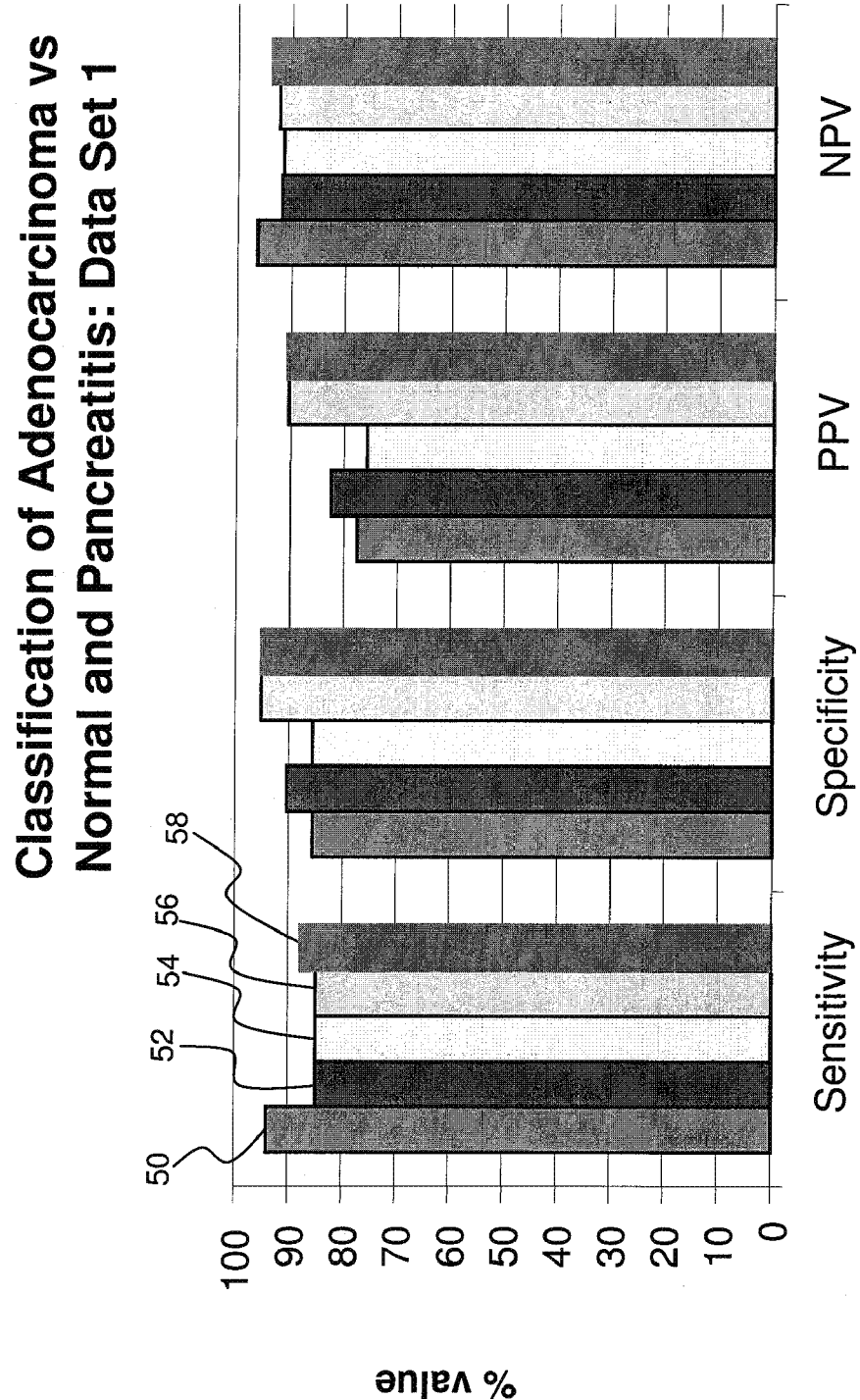
FIGS. 4A and 4B provide bar graphs illustrating the performance of the various modeling methods employed by some embodiments of the invention, namely, chemometric, PTI model, SpARC, and hybrid tissue classification algorithms in identifying adenocarcinoma tissue.
Figure 4B:
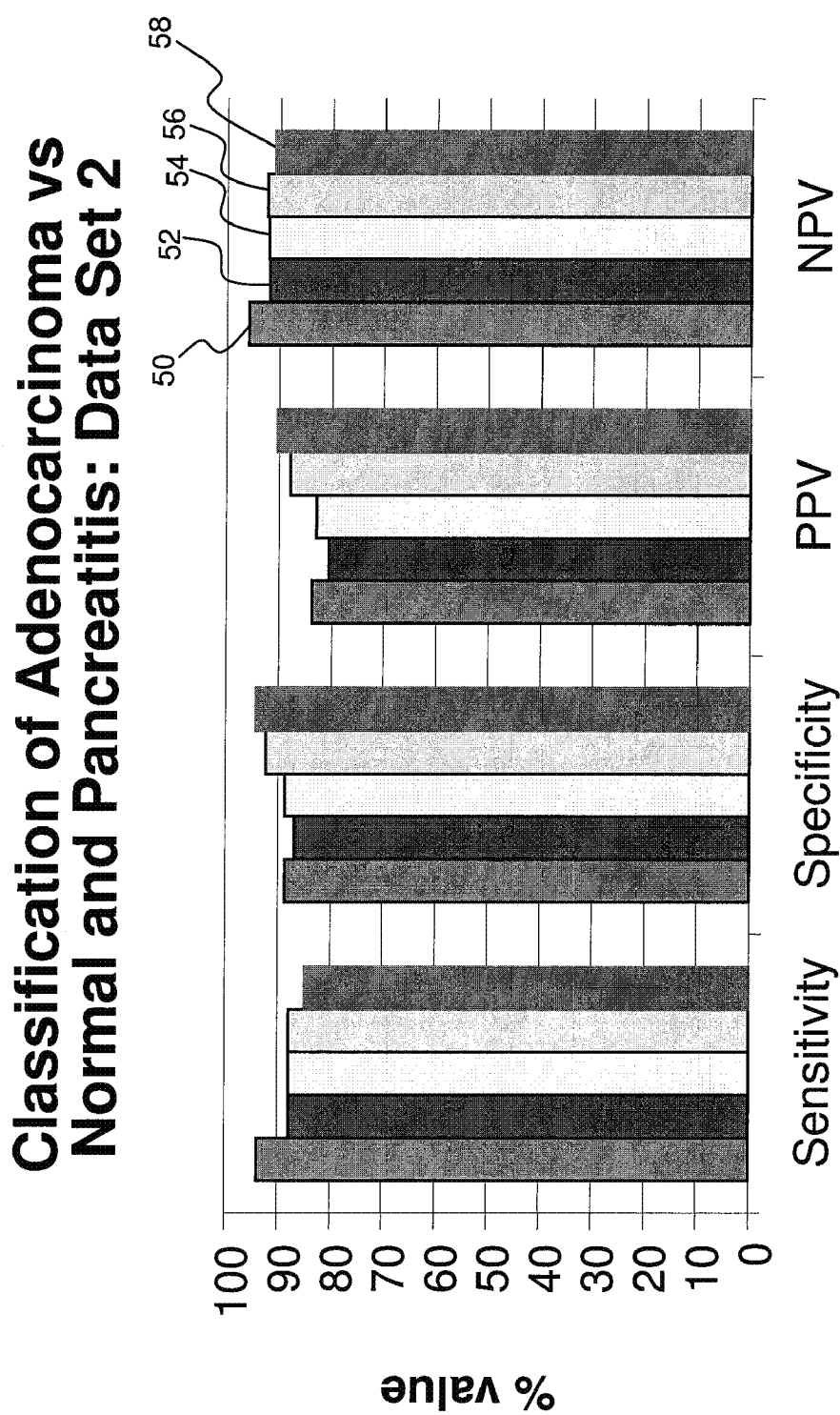

The bar plots in FIGS. 4A and 4B summarize the performance of each of the developed algorithms in identifying adenocarcinoma tissue for data Set 1 and Set 2. The chemometric algorithm represented here as the first column 50 of each grouping of columns employed RPC$_A$1, RPC$_A$2, FPC$_A$1, RPC$_{P-N}$1, RPC$_{P-N}$2, FPC$_{P-N}$1, and FPC$_{P-N}$2 for classification (as shown in Table 17 and Table 18). The PTI model algorithm represented as the second column 52 of each grouping employed L/Lo, C$_{coll}$, and C$_{NADH}$+C$_{FAD}$ for classification (Table 23 and Table 24). The SpARC algorithm represented as the third column 54 of each grouping employed R$_{ratio}$ for adenocarcinoma identification and R$_{ratio}$ and F$_{area}$ for classification of Test data as either pancreatitis or normal tissue (see Table 9 and Table 10). The hybrid algorithm is represented as the fourth column 56 of each grouping of columns. The performance of a second hybrid algorithm employing only a subset of the classifiers is also shown as the fifth column 58 of each grouping. In this case only R$_{ratio}$, RPC$_A$1, RPC$_A$2, FPC$_A$1, L/Lo, C$_{coll}$, and C$_{NADH}$+C$_{FAD}$ were employed for adenocarcinoma classification. For classification of the Test data as either pancreatitis or normal all the classifiers were employed (R$_{ratio}$, F$_{area}$, RPC$_{P-N}$1, RPC$_{P-N}$2, FPC$_{P-N}$1, FPC$_{P-N}$2, L/Lo, C$_{coll}$, and C$_{NADH}$+C$_{FAD}$). The plot shows that a combination of the developed algorithms shows the most promise for pancreatic tissue classification.

3.5 Classifying Pancreatitis Vs. Normal Tissue Using PCA and LDA on Time-Resolved Fluorescence Data The fit-coefficients of the 1$^{st}$ and 7$^{th}$ principal components were identified as diagnostically relevant for classifying pancreatitis and normal tissue. LDA was then employed to classify test data into normal and pancreatitis based on these fit-coefficient values for these diagnostically relevant principal component values.

The chemometric algorithm was validated by employing the leave-one-out technique as described above. Table 27 lists sensitivity, specificity, PPV, and NPV of the chemometric algorithm in classifying pancreatitis from normal tissue using time-resolved fluorescence data (Set 1 and Set 2). This algorithm appears to have performed the best amongst the developed algorithm for classifying between normal and pancreatitis tissue but may need further study and/or refinement.

TABLE 27

Performance of the time-resolved fluorescence data chemometric algorithm in classifying pancreatitis and normal tissue

| Data Set* | Sensitivity (%) | Specificity (%) | PPV (%) | NPV (%) |
| --- | --- | --- | --- | --- |
| Set 1 | 75.0 | 81.8 | 88.2 | 64.3 |
| Set 2 | 71.0 | 81.8 | 84.6 | 66.7 |

*Patient 11 data from both data set 1 and data set 2 were excluded due to difference in data acquisition parameters Time-resolved data will be collected with a long-pass filter (>500 nm) in front of the detector (patient 11 onwards). This will enable us to capture only a portion of the emitted fluorescence spectrum and assess its diagnostic information.

The chemometric analysis of time-resolved fluorescence data shows promise as a possible method of classifying pancreatic tissue data. It may be used in the hybrid algorithm in conjunction with the other developed algorithms for pancreatic tissue classification.

4. Discussion and Conclusion

In all the algorithms the combination of classifiers extracted from both reflectance and fluorescence performed better than using information from either just reflectance or just fluorescence. The performance of the four developed tissue classification algorithms (Chemometric, PTI model, SpARC, and Hybrid) all show promise for pancreatic tissue classification using optical spectroscopy. The sensitivity and specificity of the algorithms for adenocarcinoma identification are comparable and in some cases better than reported literature performance of EUS-FNA which is generally considered the diagnostic standard.

Illustration III

1. Introduction

In this Illustration, Reflectance and Fluorescence spectroscopy were employed to differentiate between human pancreatic adenocarcinoma and chronic pancreatitis tissue using tissue classification algorithms that employed Principal Component Analysis (PCA) and Linear Discriminant analysis (LDA). Principal component analysis was used to identify the diagnostic features in the spectra and then LDA was employed to classify the data based on these features. This Illustration involves the development of a tissue diagnostic algorithm on an enhanced data set. Preliminary PCA analysis was also conducted on time-resolved fluorescence decay measurements from these tissues.

2. Methods 2.1 Human Studies

Reflectance and fluorescence spectra and time-resolved fluorescence decays were measured from freshly excised pancreatic tissue obtained during Whipple procedures. Multiple sites were measured on tissues obtained from 12 patients within 30 minutes of excision. A total of 90 sites were measured from all the patients and two measurements were made on each site. After data acquisition from each measurement site, a portion of tissue was removed to link optical measurements with histological analysis. The study was approved by the Institutional Review Board of the University of Michigan and patient consent was obtained prior to data acquisition.

2.2 Instrumentation

The clinically compatible, fiber-optic coupled RFLS, such as system 10 described herein, was employed for data acquisition.

2.3 Pathology and Inclusion Criterion

Pathology indicated that of the measured sites 17 were adenocarcinoma sites, 22 were chronic pancreatitis sites, and 11 were normal tissue sites. The rest of the sites were either malignant breast cancer that had metastasized to the pancreas (10 sites), intraductal papillary mucinous neoplasm (IPMN—8 sites), pancreatic intraepithelial neoplasia (PanIN—6 sites), serous cyst adenoma (SCA—8 sites), scar or fat tissue or both (5 sites) or a hybrid tissue site having two or more of the above mentioned pathologies (3 sites). These sites were excluded from the data set used for algorithm development. Furthermore, those measurements that were very noisy were also excluded from the data set (4 measurements). This left a total of 33 adenocarcinoma measurements, 40 chronic pancreatitis measurements, and 22 normal measurements of both fluorescence and reflectance spectra. Tissue algorithm development was undertaken with this set of data of 95 total measurements each (Set 1) of both fluorescence and reflectance spectra.

The time-resolved fluorescence data were measured either by detecting all emitted fluorescence photons (pancreatitis=31 measurements, normal=16 measurements, and adenocarcinoma=4 measurements) or by only detecting fluorescence photons emitted at >500 nm wavelength by placing a long-pass filter in front of the APD that cut on at 500 nm (adenocarcinoma=20 measurements).

2.4 Development of the Tissue Classification Algorithm

Figure 8:
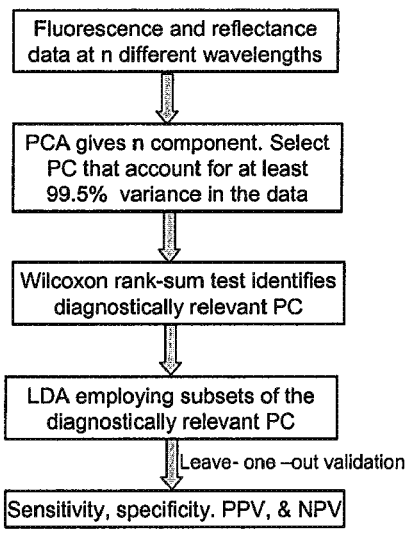
FIG. 8 illustrates a flow chart of steps in the tissue classification algorithm development process according to some embodiments of the invention and in connection with Illustration III.

FIG. 8 illustrates the steps involved in the tissue classification algorithm development process according to some embodiments. The acquired spectra were first analyzed using Principal component analysis (PCA). The Principal components (PC) that accounted of at least 99.5% of the variance in the data were identified. Wilcoxon-rank sum tests were undertaken on the fit-coefficients of these P) for each tissue type to identify the diagnostically relevant PC as described in Section 2.4.1 of this Illustration. Linear Discriminant Analysis (LDA) was then undertaken using various subsets of the diagnostically relevant PC (Section 2.4.2) to classify the spectral data employing a leave-one-out cross validation.

2.4.1. Principal Component Analysis (PCA) of the Spectra

PCA was employed to express each spectrum as a linear combination of a set of orthogonal basis vectors (or components) as discussed in the following: A. D. Joshi, J. A. Fessler, and R. A. Koeppe, "Improving PET receptor binding estimates from Logan plots using principal component analysis," Journal of Cerebral Blood Flow and Metabolism 28, 852-865 (2008). Of these components, the key-features of the data are captured by only a few vectors with high eigenvalues while the vectors corresponding to lower eigenvalues represent noise in the data. However, not all the key features of the spectra are diagnostically relevant (i.e. enabling differentiation between the tissue types). By identifying the few diagnostically relevant components, the dimensionality of the problem is reduced. The diagnostically relevant components were identified by fitting the principal components to the spectra. The components whose coefficients showed difference between tissue types were identified as diagnostically relevant.

The data spectra $\bar{s}_i \in R^{n \times 1}$ (i=1 to m) for different tissue types were grouped together and arranged row-wise in a matrix $S \in R^{m \times n}$ as shown below:

$$S = \begin{bmatrix} \bar{s}_1^T \\ \bar{s}_2^T \\ \vdots \\ \bar{s}_m^T \end{bmatrix} = \begin{bmatrix} \bar{s}_1^T \\ \vdots \\ \bar{s}_p^T \\ \vdots \\ \bar{s}_{p+q}^T \\ \vdots \\ \bar{s}_{p+q+r}^T \end{bmatrix}, \quad (11)$$

where, p, q and r (p+q+r=m) are the number of spectra for adenocarcinoma, chronic pancreatitis and normal tissue type respectively. Using PCA, the above shown n dimensional training set (corresponding to the n measured wavelengths) with m total spectra can be represented as a linear combination of n basis vectors as shown below:

$$S^T = CX, \quad (12)$$

where, $^T$ is the transpose operator, $C \in R^{n \times n}$ is the matrix of the n principal components, and X is a matrix of the fit coefficients.

$$X = \begin{bmatrix} x_{11} & x_{12} & \ldots & x_{1m} \\ x_{21} & \ddots & & \vdots \\ \vdots & & \ddots & \\ x_{n1} & \ldots & \ldots & x_{nm} \end{bmatrix}, \quad (13)$$

Where, an element $x_{ji}$ is the fit-coefficient of the $j^{th}$ component for the $i^{th}$ spectrum.

The principal component matrix C was obtained from S by employing the princomp function in MATLAB, which is incorporated herein by reference. The princomp function first calculates matrix $S_o$ by subtracting the column mean vector from each row of S. Then singular value decomposition is used to calculate the principal components as the eigenvectors of the sample covariance matrix $$\left(\frac{1}{m-1}S_0^T S_0\right).$$

Four Wilcoxon rank-sum tests were performed for the coefficients of the first 10 principal components: The hypothesis tested was that the mean fit-coefficients were significantly different for the principal component of (1) Adenocarcinoma (A) and the rest of the tissue types (2) A and chronic Pancreatitis (P), (3) A and Normal (N), (4) P and N. The principal components for which p-value was <0.05 were considered the diagnostically relevant components. The above analysis was done for both fluorescence (n=492) and reflectance spectra (n=521) separately to determine the principal components whose coefficients would be used for classification of tissue types (RPC: diagnostically relevant Reflectance PC, FPC: diagnostically relevant Fluorescence PC).

2.4.2. Linear Discriminant Analysis

Linear Discriminant Analysis (LDA) was employed using SPSS software, which is incorporated herein by reference, to distinguish between tissue types using the diagnostically relevant RPC and FPC. LDA employed a linear combination of the classification variables to distinguish between different tissue types. The analysis was undertaken by employing three different sets of diagnostically relevant PC variables: reflectance PC only, fluorescence PC only, or a combination of the reflectance and fluorescence PC variables. In the latter case, a stepwise DA was performed using minimization of Wilks' Lambda ($\Lambda$) criterion to assess the discriminating power of the variables and to select the best set of variables from diagnostically relevant RPC and FPC for classification. At each step, variables were considered for the classification algorithm only if the p-value representing the discrimination added by the variable satisfied the P-to-enter significance criterion (set as ≤0.05). Out of those variables, the variable that minimized the $\Lambda$ was selected. At the next step, all variables that had already entered the algorithm were re-assessed to see if any of them no longer sufficiently discriminated between the classification groups (measured by P-to-remove value≥0.25). This was repeated until no variables satisfied the P-to-enter criterion. The variables retained at the end by the stepwise analysis were then employed to classify the data.

A leave-one-out cross-validation was undertaken to test the performance of each of the proposed tissue classification algorithms. For each algorithm, the data were divided into Training and Test data where each data was considered as Test data one at a time, while the remaining measurements were treated as Training data. The classifiers were then employed to classify the Test data using LDA. Each algorithm was implemented 95 times and sensitivity, specificity, positive predictive value (PPV) and negative predictive value (NPV) were calculated.

2.5. Time-Resolved Fluorescence Measurements

Tissue classification using time-resolved fluorescence measurements acquired without a long-pass filter in front of the APD was restricted to normal and pancreatitis tissue measurements. This was because only four of the adenocarcinoma time-resolved fluorescence measurements were acquired without a long-pass filter. PCA was undertaken on the pancreatitis and normal tissue time-resolved fluorescence decays measured without the long-pass filter, with the premise that the shape of the decay curve should reflect changes in decay time for different tissue types, assuming the instrument response is not changing over the measurements. PCA was also carried out on the fluorescence and reflectance spectral data for the same subset of pancreatitis and normal data and LDA was performed to distinguish between pancreatitis and normal tissue sites using either only spectral data PC, or time-resolved data PC, or a combination of the two.

3. Results 3.1. Classification Using Reflectance Parameters

Table 28 lists the sensitivity, specificity, PPV and NPV for classifying tissue types using only the diagnostically relevant reflectance PC. For example, for classifying between Adenocarcinoma and chronic pancreatitis RPC1, RPC2, RPC7, and RPC8 were employed.

TABLE 28

Classification using Reflectance spectra PC

| Tissue Type | Sensitivity (%) | Specificity (%) | PPV (%) | NPV (%) | Components |
|---|---|---|---|---|---|
| A vs. P & N | 94 | 84 | 76 | 96 | RPC1, RPC2 |
| A vs. P | 79 | 88 | 84 | 83 | RPC1, RPC2, RPC7, RPC8 |
| A vs. N | 94 | 86 | 91 | 90 | RPC1, RPC2 |
| P vs. N | 80 | 82 | 89 | 69 | RPC1, RPC3, RPC5, RPC7, |

A: Adenocarcinoma;
N: Normal;
P: Pancreatitis 3.2. Classification Using Fluorescence Parameters Table 29 lists the sensitivity, specificity, PPV and NPV for classifying tissue types using only the diagnostically relevant fluorescence PC (Table 2). For example, for classifying between Adenocarcinoma and chronic Pancreatitis FPC1, FPC2, FPC6, and FPC11 were employed.

TABLE 29

Classification using Fluorescence spectra PC

| Tissue Type | Sensitivity (%) | Specificity (%) | PPV (%) | NPV (%) | Components |
|---|---|---|---|---|---|
| A vs. P & N | 79 | 79 | 67 | 88 | FPC1, FPC4, FPC6, FPC11 |
| A vs. P | 85 | 70 | 70 | 85 | FPC1, FPC2, FPC6, FPC11 |
| A vs. N | 76 | 91 | 93 | 71 | FPC1, FPC4, FPC8, FPC9 |
| P vs. N | 63 | 68 | 78 | 50 | FPC2, FPC7, FPC8, FPC9 |

A: Adenocarcinoma;
N: Normal;
P: Pancreatitis 3.3. Classification Using Fluorescence and Reflectance Parameters Table 30 lists the sensitivity, specificity, PPV and NPV for classifying tissue types using both diagnostically relevant fluorescence PC and reflectance PC, where a step-wise LDA was performed (as described in section 2.4.2) to further select classification variables from all the diagnostically relevant fluorescence and reflectance PC. The last column in Table 3 indicates the PCs used for the classification procedure. The results in Table 3 indicate that a combination of reflectance and fluorescence parameters will have a better sensitivity and specificity for identifying adenocarcinoma.

TABLE 30

Classification using Fluorescence and Reflectance spectra PC

| Tissue Type | Sensitivity (%) | Specificity (%) | PPV (%) | NPV (%) | Components |
|---|---|---|---|---|---|
| A vs. P & N | 91 | 90 | 83 | 95 | RPC1, RPC2, FPC1, FPC4, FPC6 |
| A vs. P | 82 | 85 | 82 | 85 | RPC1, RPC2, RPC8, FPC1 |
| A vs. N | 94 | 86 | 91 | 90 | RPC1, RPC2 |
| P vs. N | 83 | 86 | 92 | 73 | RPC1, RPC5, RPC7 |

A: Adenocarcinoma;
N: Normal;
P: Pancreatitis

Figure 9:
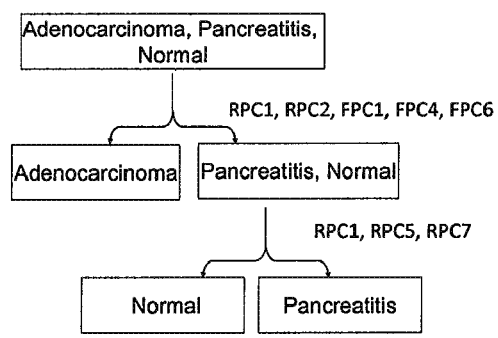
FIG. 9 illustrates a flow chart of a proposed tissue classification algorithm schematic for unknown data in accordance with some embodiments of the invention and in connection with Illustration III.

Based on the results in Table 30, data from an unknown tissue site could be classified in a two-step process where first it could be classified by employing RPC1, RPC2, FPC1, and FPC4, FPC6 into adenocarcinoma or not adenocarcinoma. If the data is classified as not cancer then RPC1, RPC5, and RPC7 could be employed to further classify the data into normal or chronic pancreatitis as shown in FIG. 9. In a clinical setting, such a classification procedure could be undertaken in a few seconds, giving a quick classification scheme to either guide EUS-FNA or for margin detection during pancreatic surgery.

3.4. Classification Using Time-Resolved Fluorescence Data

While the sample size of the adenocarcinoma data was not large enough to draw reliable conclusions, a Wilcoxon rank sum test of the decay times of normal and pancreatitis tissue indicated a difference in the mean decay times of the tissues (p-value=0.0064).

Tale 31 lists the algorithm performance for distinguishing pancreatitis from normal tissue using spectral PC only, time-resolved PC only, or a combination of the two (step-wise LDA; P-to-enter=0.08; P-to-remove=0.1). A combination of both spectral and temporal information improved the classification performance.

The time-resolved data are now being measured for fluorescence photons emitted at >500 nm wavelength as in that region, collagen emission is not dominating the fluorescence. It is thought that this might improve detection of changes in decay time due to cellular autofluorescence (NAD(P)H or FAD) to see if that enhances the difference between the various tissue types. Preliminary results show a difference between the decay times measured from adenocarcinoma with and without the long-pass filter (p-value=0.0021).

TABLE 31

Classification P vs. N using spectral and temporal PC

| Tissue Type | Sensitivity (%) | Specificity (%) | PPV (%) | NPV (%) | Components |
|---|---|---|---|---|---|
| P vs. N | 81 | 81 | 89 | 68 | RPC1, RPC5, RPC7 |
| P vs. N | 71 | 94 | 96 | 63 | TRPC1, TRPC5 |
| P vs. N | 87 | 94 | 96 | 79 | RPC1, RPC5, RPC7, TRPC5 |

N: Normal;
P: Pancreatitis

4. Discussions and Conclusion

The combination of classifiers extracted from both reflectance and fluorescence performed better than using information from either just reflectance or just fluorescence. The median (range) of reported performance of EUS-FNA, the current accepted diagnostic standard are sensitivity: 83% (54-95%), specificity: 100% (71-100%), NPV: 72% (16-92%), and PPV: 100 (92-100%) for adenocarcinoma distinction from normal tissue and chronic pancreatitis. Maximum sensitivity, specificity, PPV, and NPV of the developed chemometric tissue classification algorithm for correctly identifying adenocarcinoma were: 91%, 90%, 83%, 95%, respectively. The classification performance of the chemometric algorithm for adenocarcinoma identification is comparable and in some cases better than reported performance of EUS-FNA. We note that the results exceed the NPV for EUS-FNA, which can be unreliable for ruling out malignancy. In the setting of pancreatitis, i.e. when the patient has adenocarcinoma and pancreatitis, the sensitivity of the chemometric algorithm (82%) is well above that of EUS-FNA (54%) for distinguishing adenocarcinoma from pancreatitis, which is an unmet clinical need in pancreatic cancer detection. Thus, the performance of the developed tissue classification algorithms shows promise for pancreatic tissue classification using optical spectroscopy. In a clinical setting such a classification procedure could be undertaken for rapid tissue classification scheme either guide EUS-FNA or for margin detection during pancreatic surgery.

The average fluorescence decay times for normal and pancreatitis tissue were found to differ (p<0.01). Classification algorithms that incorporated time-resolved fluorescence PC along with and reflectance and fluorescence spectral PC had the best classification performance for distinguishing between normal and pancreatitis tissue types indicating that inclusion of time-resolved data in the analysis could potentially improve the classification performance of the developed tissue classification algorithms.

Illustration IV

A photon-tissue interaction (PTI) model was utilized to analyze 96 pairs of diffuse reflectance and fluorescence spectra obtained from freshly excised human pancreatic tissues. For each pair of spectra, the PTI model extracted a nuclear size parameter from the measured reflectance, as well as the relative contributions of native tissue fluorophores (collagen, NADH, FAD) to the measured fluorescence. All four of the aforementioned parameters extracted from the PTI model were shown to be statistically significant for distinguishing pancreatic adenocarcinoma from normal pancreatic tissue and pancreatitis.

Reflectance and fluorescence spectra were measured from 50 pancreatic tissue sites, and after the RFLS measurements took place, a section was taken from each of these sites and sent to histology for diagnosis by a pathologist. Of the 50 sites used in this study, 11 were diagnosed by pathology as histologically normal, 22 were diagnosed as pancreatitis, and 17 were diagnosed as adenocarcinoma. From each of these sites (except for one adenocarcinoma site), two reflectance and two fluorescence spectra were taken. Three of the spectra were removed from the data set due to low SNR, resulting in 96 pairs of reflectance and fluorescence spectra that were individually fit using the PTI algorithm.

The PTI model has been described in detail elsewhere, see R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009) for example, as well as herein. In short, an empirical model of reflectance as a function of the tissue scattering and absorption coefficients is employed to construct a wavelength-resolved scaling factor to transform an average measured "canonical normal" pancreatic tissue reflectance spectrum. A model spectrum resulting from this transformation was then fit to each individual measured reflectance spectrum via minimization of the cost function $|R_{model}(\lambda) - R_{measured}(\lambda)|$.

In the fitting procedure, the reduced scattering coefficient of the tissue ($\mu_s(1-g)$, where g is the tissue anisotropy) was modeled as the sum of two Mie theory terms: one for spherical scatterers (cell nuclei) and one for cylindrical scatterers (collagen fibers). The cylindrical Mie scattering term was kept constant, but in the spherical scattering term, the ratio L/Lo of the diameter of the cell nuclei in the model to that of normal pancreatic tissue was varied from 1.0 to 1.5 in steps of 0.1. The refractive indices $n_s$ and $n_c$ of the spherical and cylindrical scatterers were also kept constant. The absorption coefficient was modeled as a linear combination of oxy- and deoxy-hemoglobin. The total hemoglobin concentrations of the "canonical normal" reflectance spectrum ($[Hb]_{tot,N}$) and the modeled spectrum ($[Hb]_{tot,model}$) were both varied from 2.5 µM to 25 µM in steps of 2.5 µM. The blood-oxygen saturation of the normal reflectance spectrum ($SO_{2,N}$) and the modeled spectrum ($SO_{2,model}$) were both varied from 0.1 to 0.9 in steps of 0.2. The values of L/Lo, $[Hb]_{tot,N}$, $[Hb]_{tot,model}$, $SO_{2,N}$, and $SO_{2,model}$ that minimized the cost function were extracted from the fit of the reflectance model to each individual measured reflectance spectrum.

Once the model described above was fit to an individual measured reflectance spectrum, the reduced scattering coefficient $\mu_s(1-g)$ extracted from the best fit was put into a Beer-Lambert factor of the form $\exp[\mu_a+(\lambda_s(1-g))z]$ to correct the corresponding measured fluorescence spectrum for attenuation artifacts. In this equation, the average path length z of a fluorescent photon in the tissue was taken to be 0.064 cm for all tissue types; this value had been estimated previously from Monte Carlo simulations. In order to avoid undercorrection or over-correction, the values of $[Hb]_{tot,model}$ and $SO_{2,model}$ were allowed to vary in this procedure as well. The resulting "intrinsic" fluorescence spectrum $F_{intrinsic}(\lambda)$ was then fit to a linear combination BasisFit($\lambda$) of the basis spectra of three endogenous tissue fluorophores: collagen, NADH, and FAD. These basis spectra were blue-shifted by 12 nm to account for the fact that they were measured in chemical solvents and not a biological tissue environment. The best fit was determined via minimization of the cost function |BasisFit($\lambda$)−$F_{intrinsic}(\lambda)$| from 400-638 nm [12]. The fit coefficients $C_{coll}$, $C_{nadh}$, and $C_{fad}$ extracted from this fit were then normalized via division by their sum, in order to obtain the percentage contributions % COLL, % NADH, and % FAD from the constituent endogenous fluorophores. These percentages summed to 1 for each measured fluorescence spectrum.

A two-tailed t-test was performed for each parameter, L/Lo, % COLL, % NADH, and % FAD, to see if the differences in the parameter were statistically significant for distinguishing pancreatic adenocarcinoma from normal pancreatic tissue, distinguishing pancreatic adenocarcinoma from pancreatitis, and distinguishing malignant pancreas (adenocarcinoma) from benign pancreas (normal pancreatic tissue and pancreatitis). For each of these three cases, all four parameters were found to be statistically significant (p<0.05). When these four parameters were used as inputs to a Linear Discriminant Analysis (LDA) algorithm for classification of the individual tissue spectra as either "adenocarcinoma" or "normal and pancreatitis", 31 of the 33 adenocarcinoma spectra were classified correctly and 52 of the 62 "normal and pancreatitis" spectra were classified correctly. The sensitivity, specificity, positive predictive value, and negative predictive value of the PTI-LDA algorithm were 93.9%, 83.9%, 75.6%, and 96.2%, respectively. These results show the potential of the PTI model to extract diagnostically-relevant biological parameters from measured reflectance and fluorescence spectra of human pancreatic tissues, among other things. The potential of the PTI algorithm to correctly distinguish pancreatic adenocarcinoma from pancreatitis is further illustrated by this Illustration.

Illustration V

1. Introduction

This Illustration provides an assessment of the diagnostic accuracy of algorithms developed for pancreatic tissue classification using data from fiber-optic probe-based bi-modal optical spectroscopy, an approach that would be compatible with minimally-invasive diagnostic procedures for early cancer detection in the pancreas. A total of 95 fluorescence and 95 reflectance spectra were considered from 50 freshly excised tissue sites (including human pancreatic adenocarcinoma, chronic pancreatitis (inflammation), and normal tissues) on 9 patients. Classification algorithms using linear discriminant analysis were developed to distinguish among tissues and leave-one-out cross validation was employed to assess the classifiers' performance. The SpARC (Spectral Areas and Ratios Classifier) algorithm employed a combination of reflectance and fluorescence data and had the best performance, with sensitivity, specificity, negative predictive value, and positive predictive value for correctly identifying adenocarcinoma being 85%, 90%, 92%, and 82%, respectively. These results exceed the performance of EUS-FNA, which is insensitive to distinguishing adenocarcinoma from pancreatitis and is unreliable at ruling out malignancy in the pancreas.

2. Methods 2.1 Human Studies

In this illustration, pancreatic tissue classification algorithms employing fluorescence data alone, reflectance data alone, or a combination of the two, were used to determine whether both reflectance and fluorescence information were necessary for optimal tissue classification. Optical spectra were measured from freshly excised pancreatic tissues obtained during surgery. A system such as system 10 discussed herein was employed to study 50 tissue sites from 9 patients within 30 minutes of tissue excision. After optical data acquisition from each measurement site, tissue at the site was removed for histopathological analysis. The study was approved by the Institutional Review Board of the University of Michigan (U of M) Medical School and patient consent was obtained prior to data acquisition.

2.2 Methods for Classification

Acquired fluorescence spectra in the 360-750 nm range were corrected for spectral instrument response after background correction. Reflectance spectra were background subtracted (R) and then scaled by the lamp reflectance spectrum ($R_o$) to obtain corrected reflectance spectra (R/$R_o$) in the 400-750 nm spectral range. All spectra were then normalized by scaling the peak intensity value to unity. Tissue algorithm development was undertaken with 95 fluorescence measurements and 95 reflectance measurements: 33 fluorescence and reflectance measurements were made on 17 adenocarcinoma sites, 40 were made on 22 pancreatitis sites, and 22 were made on 11 normal sites.

Figure 10:
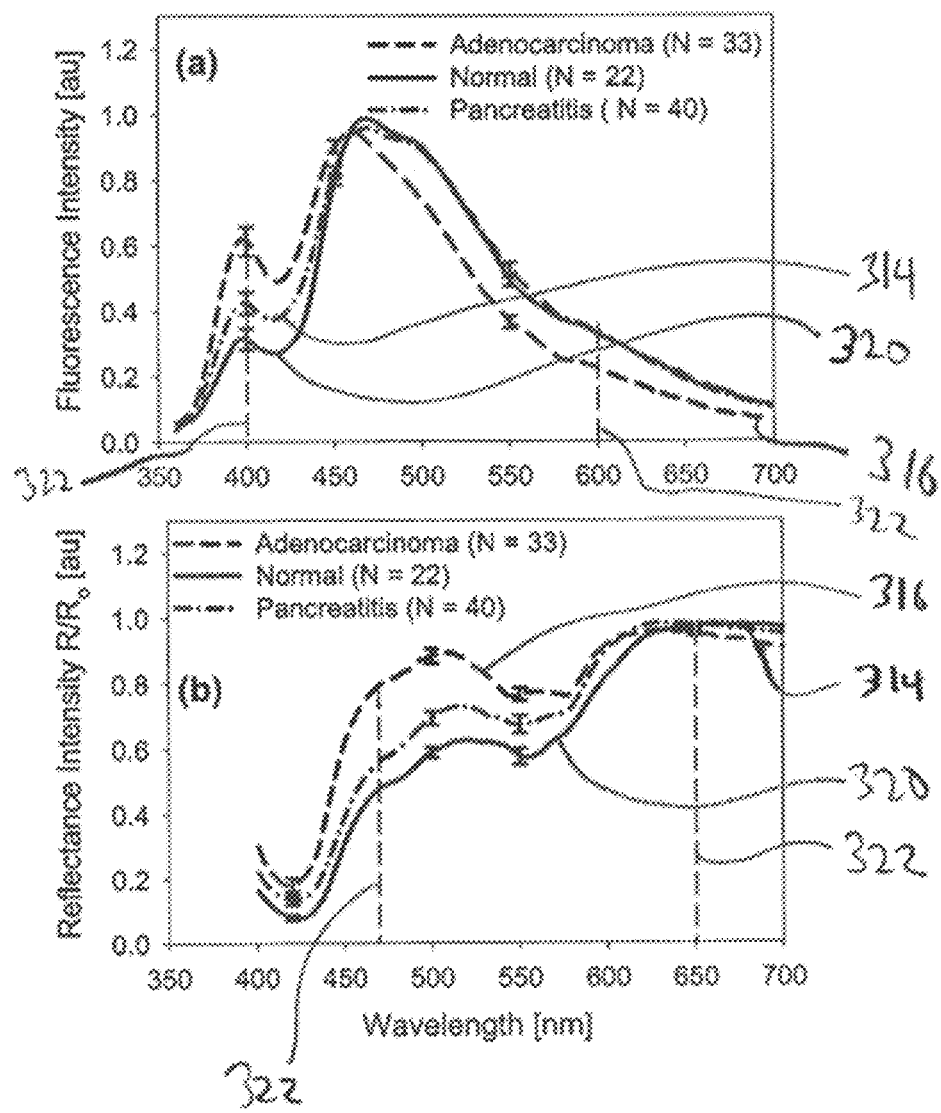
FIGS. 10a and 10b are graphs depicting the mean of normalized measured fluorescence (FIG. 10a) and reflectance (FIG. 10b) and spectra for adenocarcinoma, pancreatitis, and normal pancreatic tissues along with the standard error at select wavelengths in connection with some embodiments of the invention and Illustration IV.

FIG. 10a,b shows the mean of normalized measured reflectance and fluorescence spectra for adenocarcinoma (dashed line 316), pancreatitis (dot-dashed line 314), and normal (solid line 320) pancreatic tissues along with the standard error at select wavelengths. The adenocarcinoma sites showed a markedly higher reflectance than pancreatitis and normal tissue sites in the 450 to 540 nm range and a higher (lower) fluorescence at around 400 nm (450 to 700 nm range). To classify the tissue spectra based on these apparent differences, the ratio $R_{ratio}=R_{470}/R_{650}$ was calculated for each reflectance spectrum, the wavelength integrated fluorescence ($F_{area}$) was calculated as the area under each normalized fluorescence spectrum, and the ratio $F_{ratio}=F_{400}/F_{600}$, was calculated for each fluorescence spectrum. The vertical dashed lines 322 in FIG. 10a,b indicate the wavelength at which the ratios $R_{ratio}$ and $F_{ratio}$ were calculated.

Three different sets of these calculated spectral parameters ("classification variables") were employed to develop tissue classification algorithms for distinguishing (a) adenocarcinoma (A) from pancreatitis (P) and normal (N) tissue, (b) A from P tissue, (c) A from N tissue, and (d) P from N tissue. A leave-one-out cross-validation was undertaken to test the performance of the proposed tissue classification algorithms by considering each measured spectrum as the test data and by employing the remaining spectra as training data in the classification algorithm. Linear Discriminant Analysis (LDA) was employed using SPSS software to classify the test data using the three different sets of classification variables. LDA employs a linear combination of the classification variables to classify data. This process was repeated for each spectrum and the sensitivity, specificity, negative predictive value (NPV), and positive predictive value (PPV), of the classification algorithms were calculated.

The first classification algorithm, RSpARC (reflectance spectral areas and ratios classifier), employed $R_{ratio}$ as the sole classification variable for LDA and Table 32 provides the algorithm performance. The second algorithm, FSpARC (fluorescence spectral areas and ratios classifier), employed $F_{area}$ and $F_{ratio}$ as the classification variables for LDA and Table 33 gives that algorithm's performance. In the third algorithm, SpARC (spectral areas and ratios classifier), stepwise LDA was performed using minimization of Wilks' Lambda (Λ) criterion (P-to-enter 0.06; P-to-remove 0.01) to assess the discriminating power of the variables and to select the best set of variables from $R_{ratio}$, $F_{area}$, and $F_{ratio}$ for classification. The variables retained by the stepwise analysis were then employed to classify the data. Table 34 shows the performance of this algorithm along with the variables retained for each classification. For example, classification of A vs. P and N employed $R_{ratio}$ and $F_{ratio}$. The combination of classifiers extracted from both reflectance and fluorescence (Table 34) performed better than using information from either just reflectance (Table 32) or just fluorescence (Table 33), indicating that bi-modal optical spectroscopy with both fluorescence and reflectance is needed for pancreatic tissue classification.

TABLE 32

RSpARC algorithm - reflectance only

| Tissue Type | Sensitivity (%) | Specificity (%) | NPV (%) | PPV (%) |
|---|---|---|---|---|
| A vs. P and N | 85 | 85 | 91 | 76 |
| A vs. P | 85 | 85 | 87 | 82 |
| A vs. N | 88 | 95 | 84 | 97 |
| P vs. N | 58 | 82 | 51 | 85 |

N: Normal;
P: Pancreatitis;
A: Adenocarcinoma

TABLE 33

FSpARC algorithm - fluorescence only

| Tissue Type | Sensitivity (%) | Specificity (%) | NPV (%) | PPV (%) |
|---|---|---|---|---|
| A vs. P and N | 55 | 87 | 78 | 69 |
| A vs. P | 52 | 85 | 68 | 74 |
| A vs. N | 58 | 91 | 59 | 90 |
| P vs. N | 58 | 64 | 45 | 74 |

N: Normal;
P: Pancreatitis;
A: Adenocarcinoma

TABLE 34

SpARC algorithm - relectance and fluorescence

| Tissue Type | Sensitivity (%) | Specificity (%) | NPV (%) | PPV (%) |
|---|---|---|---|---|
| A vs. P and N[a,b] | 55 | 87 | 78 | 69 |
| A vs. P[a] | 52 | 85 | 68 | 74 |
| A vs. N[a] | 58 | 91 | 59 | 90 |
| P vs. N[a,c] | 58 | 64 | 45 | 74 |

Classification parameters
[a]$R_{ratio}$;
[b]$F_{ratio}$;
[c]$F_{area}$

Figure 11:
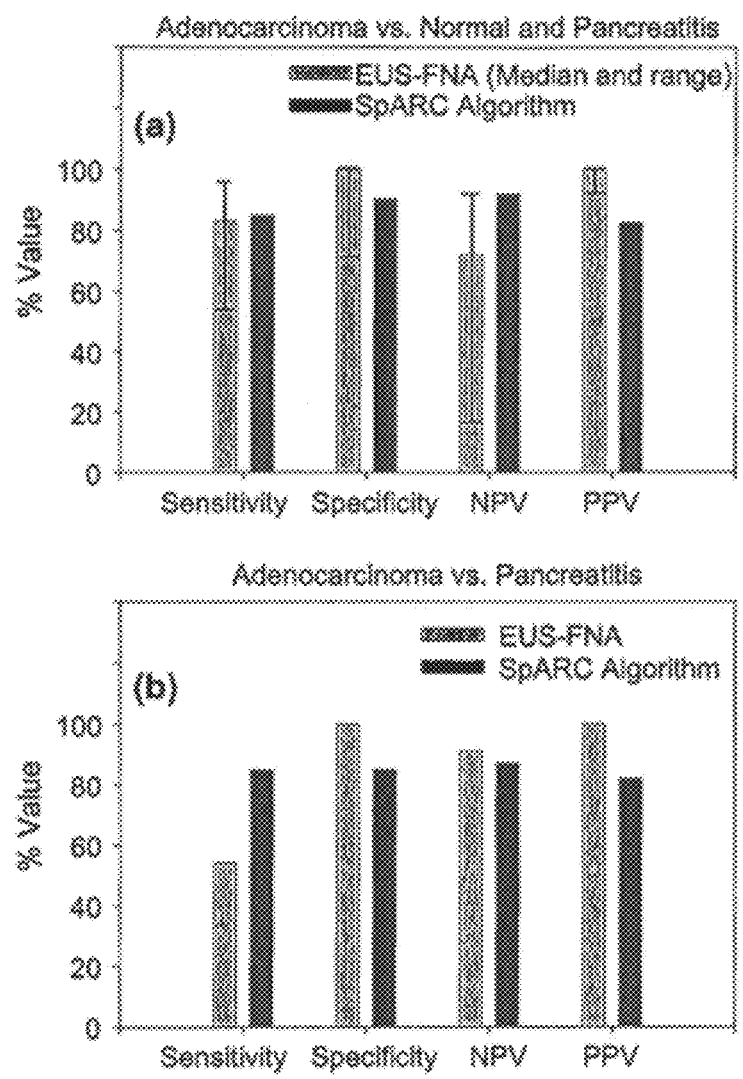
FIG. 11a is a bar graph depicting the median and range of sensitivity, specificity, NPV, and PPV for adenocarcinoma identification using clinical EUS-FNA and the SpARC algorithm
FIG. 11b is a bar graph depicting the performance of EUS-FNA (gray bars) and the SpARC algorithm for distinguishing between adenocarcinoma and pancreatitis in the setting of chronic pancreatitis according to some embodiments of the invention and Illustration IV.

The performance of the SpARC algorithm for adenocarcinoma distinction from normal tissue and chronic pancreatitis is comparable to that of, and in some cases better than, the reported performance of EUS-FNA, the currently accepted diagnostic standard. FIG. 11(a) plots in light gray the median (range) of reported EUS-FNA sensitivity: 83% (54-95%), specificity: 100% (71-100%), NPV: 72% (16-92%), and PPV: 100 (92-100%) for adenocarcinoma distinction from normal tissue and chronic pancreatitis. Plotted in dark gray for comparison is the performance of the SpARC algorithm (first row of Table 34). According to the results, the SpARC results exceed the NPV for EUS-FNA, which can be unreliable for ruling out malignancy.

In the setting of pancreatitis, i.e. when the patient has adenocarcinoma and pancreatitis, the sensitivity of SpARC (85%) is well above that of EUS-FNA (54%) (FIG. 11(b)) for distinguishing adenocarcinoma from pancreatitis, which is an unmet clinical need in pancreatic cancer detection. Based on the results in Table 34, a potential method for classifying an unknown tissue site could employ $R_{ratio}$ and $F_{ratio}$ to classify the data set as adenocarcinoma or not adenocarcinoma using LDA. If the data is classified as not cancer, then $R_{ratio}$ and $F_{area}$ could be employed to classify it as pancreatitis or normal tissue types.

While this Illustration involved an ex vivo setting, the performance of the developed tissue classification algorithm shows promise for clinical pancreatic tissue classification using bi-modal optical spectroscopy. In other embodiments, the methods described herein will also involve data acquisition in vivo, with the aim deploying the fiber-optic probe, as in system 10, through a needle for optically-guided EUS-FNA.

Illustration VI

1. Introduction

As discussed herein, reflectance and fluorescence spectral features could potentially be employed for human pancreatic cancer detection. An empirical PTI model to quantitatively link those spectroscopic measurements to histologically known characteristics of malignant and non-malignant human pancreatic tissues is also provided. The PTI reflectance model incorporated information about light scattering by cell nuclei and collagen fibers, as well as absorption by oxygenated and deoxygenated hemoglobin. The PTI fluorescence model then corrected fluorescence spectra measured at the same site as the reflectance spectra for absorption and scattering artifacts.

This Illustration provides, among other things, a further developed PTI model which is employed to analyze 96 pairs of reflectance and fluorescence spectra from freshly excised human pancreatic tissues. For each pair of spectra, the PTI model extracted a cellular nuclear size parameter from the measured reflectance, and the relative contributions of extracellular and intracellular fluorophores to the intrinsic fluorescence. The results indicated inter alia a statistically significant increase in the nuclear size of adenocarcinoma (relative to both normal pancreatic tissue and chronic pancreatitis) and a statistically significant increase in the extracellular collagen contribution to fluorescence in both adenocarcinoma and chronic pancreatitis (relative to normal pancreatic tissue). This suggests that reflectance and fluorescence spectroscopies have the potential to quantitatively distinguish among pancreatic tissue types, including normal pancreatic tissue, chronic pancreatitis, and pancreatic adenocarcinoma, via biophysical tissue properties extracted from the spectra.

2. Experimental Methods 2.1 Instrumentation

A RFLS device, such as system 10 and the embodiments thereof described herein, measured reflectance and fluorescence from human pancreatic tissue samples. At each tissue site, fluorescence and reflectance measurements were made in sequence by using shutters to block the other light source. Each fluorescence (reflectance) measurement had an associated acquisition time of 2 seconds (2.5 seconds). All measured reflectance and fluorescence spectra were background-corrected and corrected for the instrument response function. Corrected reflectance spectra $R/R_o$ were obtained by background subtraction and then dividing by the reflectance spectrum $R_o$ of the lamp. The lamp spectrum $R_o$ was measured by placing a reflectance standard (SRS-50-010, Labsphere, North Sutton, N.H.) or a neutral density filter (optical density 0.05) at the distal end of the probe and collecting the lamp light that was reflected from the surface of the reflectance standard. Each wavelength-resolved spectrum was normalized to peak intensity.

2.2 Human Studies

Reflectance and fluorescence spectra were measured from human pancreatic tissue samples within 30 minutes of excision, during operative procedures (Whipple procedure or distal pancreatectomy) performed on 9 patients (average age 62±11 years; 7 female, 2 male). The study received approval from the Institutional Review Board of the U of M Medical School. Prior to data acquisition, written consent was obtained from each patient.

Spectra were measured from 50 pancreatic tissue sites. Immediately following optical measurement, a tissue biopsy was taken from each of these sites and used for histopathologic analysis. Of the 50 sites, 11 were diagnosed by pathology as histologically normal, 22 were diagnosed as chronic pancreatitis (inflammation), and 17 were diagnosed as adenocarcinoma. All pancreatic adenocarcinoma spectra in this study were from patients who had concurrent histologic evidence of chronic pancreatitis in addition to pancreatic adenocarcinoma. Two wavelength-resolved reflectance spectra and two wavelength-resolved fluorescence spectra were taken from each tissue site, except for one adenocarcinoma site, from which only one set of these three measurements was taken.

Two pairs of chronic pancreatitis spectra were excluded because the fluorescence spectra had a signal-to-noise ratio (SNR) of less than 25, where SNR was defined to be the mean signal at peak fluorescence divided by the standard deviation of the noise in the measured spectrum. Another pair of chronic pancreatitis spectra was excluded because the intensity of the reflectance signal at 550 nm was less than 1/10 of that at 650 nm. The remaining 96 pairs of reflectance and fluorescence spectra (22 pairs of normal spectra, 41 pairs of chronic pancreatitis spectra, 33 pairs of adenocarcinoma spectra) were individually fit using the PTI model.

3. Photon-Tissue Interaction (PTI) Model 3.1 PTI Reflectance Model and Fitting Procedure The PTI model is described in detail herein. Briefly, an empirical model of reflectance $R^{EMP}(\mu_s, \mu_a; \lambda)$ as a function of the tissue scattering coefficient $\mu_s$ (related to the nuclear diameter L and nuclear refractive index $n_s$) and absorption coefficient $\mu_a$ (related to the total hemoglobin concentration $[Hb]_{tot}$ and blood oxygen saturation $SO_2$) was employed to construct a wavelength-resolved scaling factor to transform an average measured "canonical normal" pancreatic tissue reflectance spectrum $R^{MEASURED}_{NORMAL}(\mu_a, \mu_s; \lambda)$ into the PTI model spectrum $R^{PTI}_{UNKNOWN}(\mu_a, \mu_s; \lambda)$ for each of the 96 individual measured reflectance spectra:

$$R^{PTI}_{UNKNOWN}(\mu_a, \mu_s; \lambda) = (R^{MEASURED}_{NORMAL}(\mu_a, \mu_s; \lambda)) \left( \frac{R^{EMP}_{UNKNOWN}(\mu_a, \mu_s; \lambda)}{R^{EMP}_{NORMAL}(\mu_a, \mu_s; \lambda)} \right). \quad (14)$$

The PTI-modeled spectra are denoted "unknown" because the model was blinded to pancreatic tissue type. Each model spectrum $R^{PTI}_{UNKNOWN}(\mu_a, \mu_s; \lambda)$ resulting from Eq. (1) was individually fit to the corresponding measured reflectance spectrum $R^{MEASURED}(\mu_a, \mu_s; \lambda)$ by varying the nuclear diameter L, total hemoglobin concentration $[Hb]_{tot}$, and blood-oxygen saturation $SO_2$ over biologically reasonable ranges (Table 1) and minimizing the cost function $|R^{PTI}_{UNKNOWN} - R^{MEASURED}|$ over the wavelength range of 400 nm to 700 nm.

TABLE 35

Ranges and step sizes for tissue parameters in the PTI model

| Tissue parameter | Minimum value | Maximum value | Step size |
|---|---|---|---|
| L | 9 μm | 13.5 μm | 0.9 μm |
| $[Hb]_{tot}$ | 2.5 μm | 25 μm | 2.5 μm |
| $SO_2$ | 0.1 | 0.9 | 0.2 |

The fitting procedure in this study was identical to those discussed herein and in R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009), except for four changes: (1) The measured "canonical normal" spectrum was taken to be an average of all 22 measured normal spectra. (Each normal reflectance spectrum was first normalized to its peak value in the 400-700 nm wavelength range, then all 22 of these spectra were averaged, and, finally, the resulting spectrum was normalized to the peak again to create the "canonical normal" spectrum.). (2) The concentration of collagen fibers (cylindrical scatterers) for all unknown reflectance spectra was set to three times that of the canonical normal (motivated by previous work demonstrating that the mean collagen content of both pancreatic cancer and tumor-associated chronic pancreatitis was roughly three times as high as that of normal pancreatic tissue). This approximation was not expected to have a significant effect on the fitting procedure, because the key disease-related changes in the reflectance spectra were expected to be captured by changes in the variable L. (3) The refractive index of cell nuclei for all tissue types was set to a constant value of 1.375, which was in good agreement with the previous results. (4) The nuclear diameter L was varied from 9 μm to 13.5 μm, which contains the anticipated range for the pancreatic tissue types examined in this study.

Thus, the parameters extracted from the best fit of each "unknown" reflectance spectrum to the PTI model were the mean diameter L of the cell nuclei, as well as the total hemoglobin concentration and blood-oxygen saturation. The value of L from each "unknown" reflectance spectrum was compared to the value $L_o$ (set to 9 μm) that had been input into the PTI model for the mean cellular nuclear diameter of the "canonical normal" tissue. The ratio of $L/L_o$, termed the nuclear dilation factor, was calculated for each "unknown" reflectance spectrum. The tissue scattering properties extracted from the PTI model were then employed to correct the corresponding fluorescence spectra for attenuation artifacts, as described in the following Section 3.2 of this Illustration.

3.2 PTI Fluorescence Model and Fitting Procedure

Once the model described above was fit to an individual measured reflectance spectrum, the corresponding measured fluorescence spectrum $F_{MEASURED}(\lambda)$ was corrected for scattering and absorption attenuation artifacts with a Beer-Lambert factor, where the scattering coefficient was obtained from fitting the reflectance spectrum, as discussed above in Section 3.1. The resulting "intrinsic" fluorescence spectrum $F_{INTRINSIC}(\lambda)$ was fit to a linear combination of the basis spectra from three endogenous tissue fluorophores: extracellular collagen, intracellular NADH, and intracellular FAD, as described previously:

$$F_{INTRINSIC}(\lambda) = C_{COLL}F_{COLL}(\lambda) + C_{NADH}F_{NADH}(\lambda) + C_{FAD}F_{FAD}(\lambda). \quad (15)$$

The extracted fit coefficients $C_{COLL}$, $C_{NADH}$, and $C_{FAD}$ were then normalized via division by their sum, in order to obtain the percentage contributions % COLL, % NADH, and % FAD from the constituent endogenous tissue fluorophores. These percentages summed to 100% for each measured fluorescence spectrum.

4. Results 4.1 Measured Reflectance and Fluorescence Spectra from Human Pancreatic Tissues FIG. 12$a,b$ shows representative reflectance and fluorescence spectra measured from normal pancreatic tissue (solid line 420), chronic pancreatitis (dotted line 414), and pancreatic adenocarcinoma (dashed line 416). As reported previously, there are noticeable differences between the spectra of the different tissue types. From 450 nm to 530 nm, there is a significant increase in the amplitude of the adenocarcinoma reflectance spectrum (relative to normal and chronic pancreatitis), attributed to the increased size of cell nuclei in adenocarcinoma. Near 400 nm, there are notable increases in the amplitude of the adenocarcinoma and chronic pancreatitis fluorescence spectra (relative to normal), attributed to the increased extracellular collagen content in adenocarcinoma and chronic pancreatitis.

4.2 Fits of PTI Model to Reflectance and Fluorescence Spectra

Figure 12:
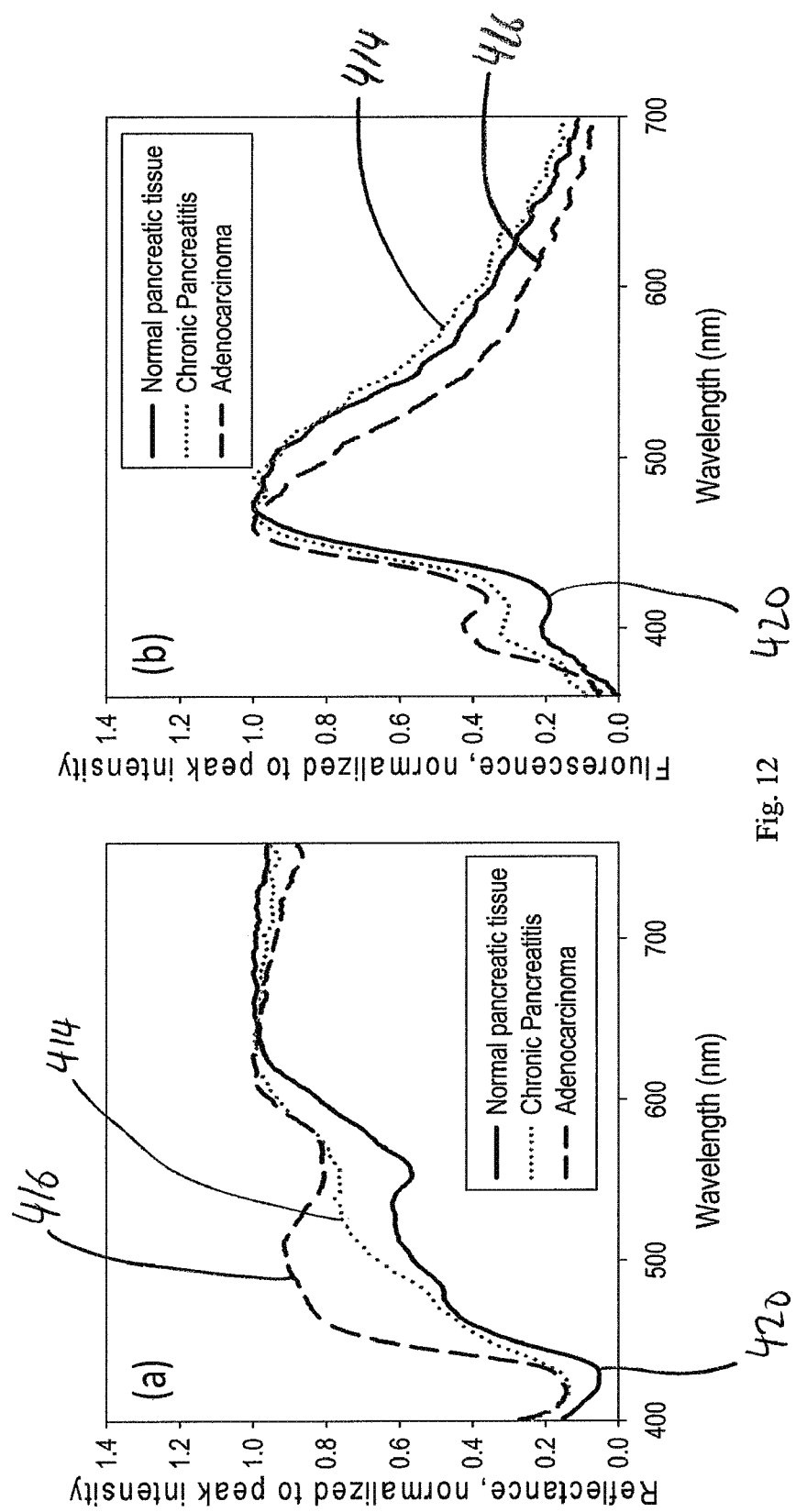
FIG. 12a,b are graphs which are representative of reflectance (FIG. 12a) and fluorescence (FIG. 12b) spectra of normal pancreatic tissue, chronic pancreatitis, and pancreatic adenocarcinoma in connection with some embodiments of the invention and Illustration VI.
Figure 13:
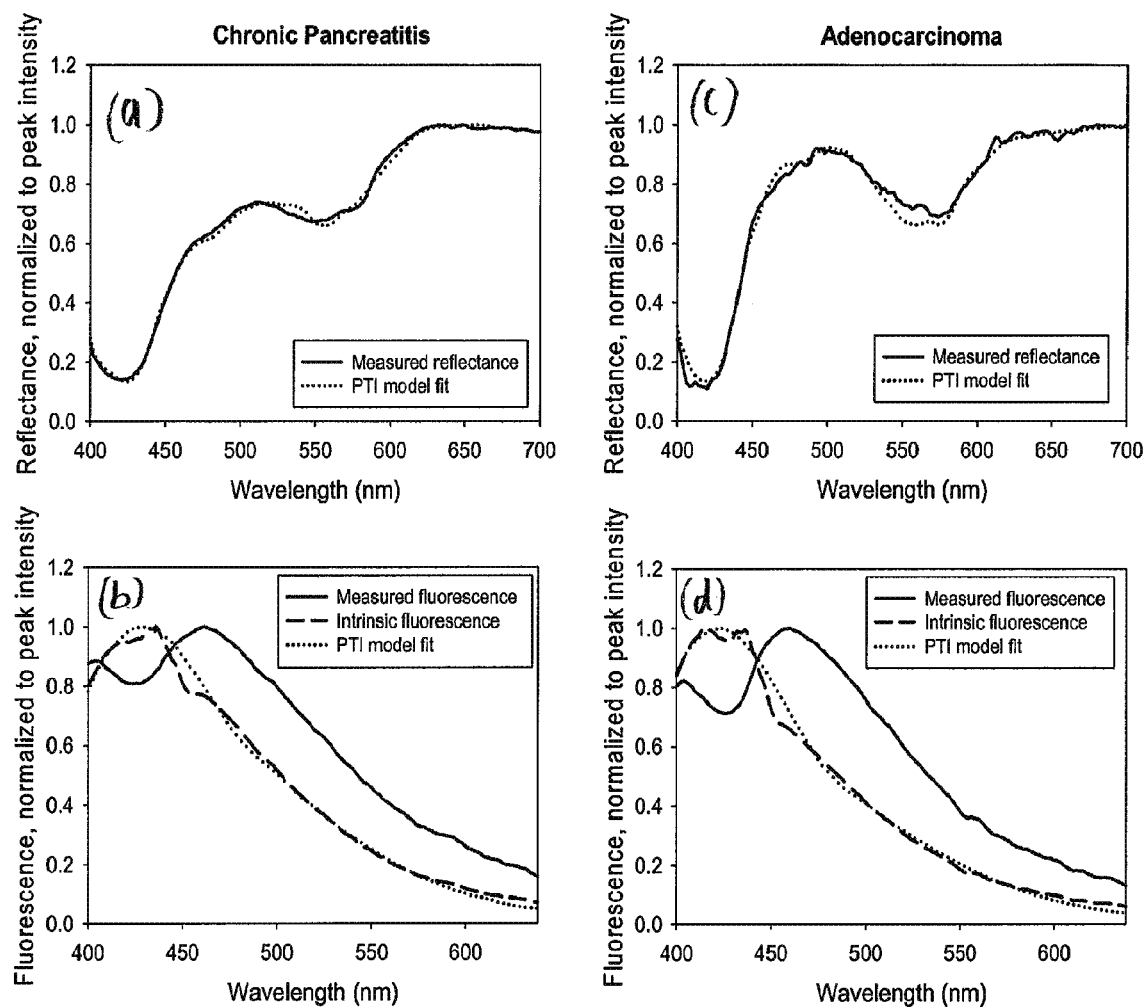
FIG. 13 includes graphs of the best fits of the PTI model to measured reflectance spectra and intrinsic fluorescence spectra for chronic pancreatitis (FIG. 13a and FIG. 13b, respectively) and adenocarcinoma spectra (FIG. 13c and FIG. 13d, respectively) in connection with some embodiments of the invention and Illustration VI.

FIG. 13 shows best fits of the PTI model to reflectance and fluorescence spectra from chronic pancreatitis (FIG. 13$a,b$) and pancreatic adenocarcinoma (FIG. 13$c,d$). The average error in fit of the PTI reflectance model to the 96 measured spectra was less than 15% in the wavelength range 450-530 nm. This spectral range is where significant differences in spectral amplitude were reported for adenocarcinoma, relative to normal pancreatic tissue and pancreatitis, as can be seen in FIG. 12($a$). The average error in fit of the PTI fluorescence model to the 96 "intrinsic" fluorescence spectra was less than 6% in the wavelength range of 500-550 nm, in which key differences in spectral amplitude were reported for the different pancreatic tissue types (see FIG. 12($b$)). When the 11 (out of 96) reflectance spectra with the highest cost functions were discarded, the average error in fit of the PTI reflectance model to the remaining 85 reflectance spectra fell below 10% in the 450-530 nm wavelength range, the average error in fit of the PTI fluorescence model to the 85 corresponding fluorescence spectra in the 500-550 nm wavelength range was nearly unchanged (remaining at less than 6%), and there was no significant change to the mean or standard error for the extracted parameters (see Sections 4.3 and 4.4 below in connection with this Illustration).

4.3 PTI Reflectance Model Extracts Cellular Nuclear Dilation Factor

Figure 14A:
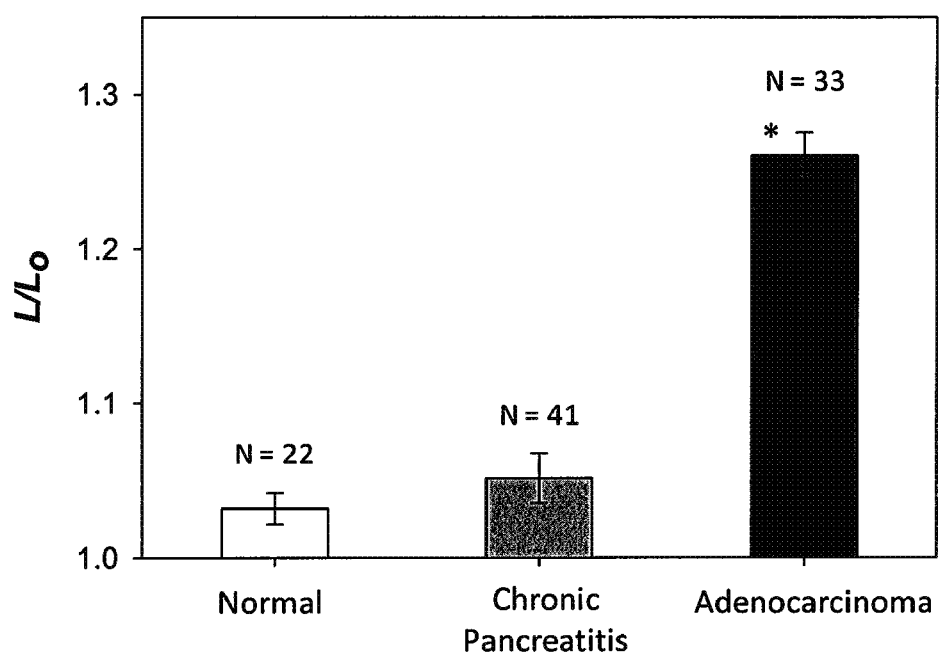
FIG. 14a is a bar graph depicting extracted nuclear dilation factor $L/L_o$ for normal pancreatic tissue (N=22 spectra), chronic pancreatitis (N=41 spectra), and pancreatic adenocarcinoma (N=33 spectra), which shows differences that were statistically significant (*, $p<2\times10^{-9}$ from Wilcoxon rank-sum tests) for distinguishing adenocarcinoma from normal pancreatic tissue as well as distinguishing adenocarcinoma from chronic pancreatitis, among other things, in connection with Illustration VI.
Figure 14B:
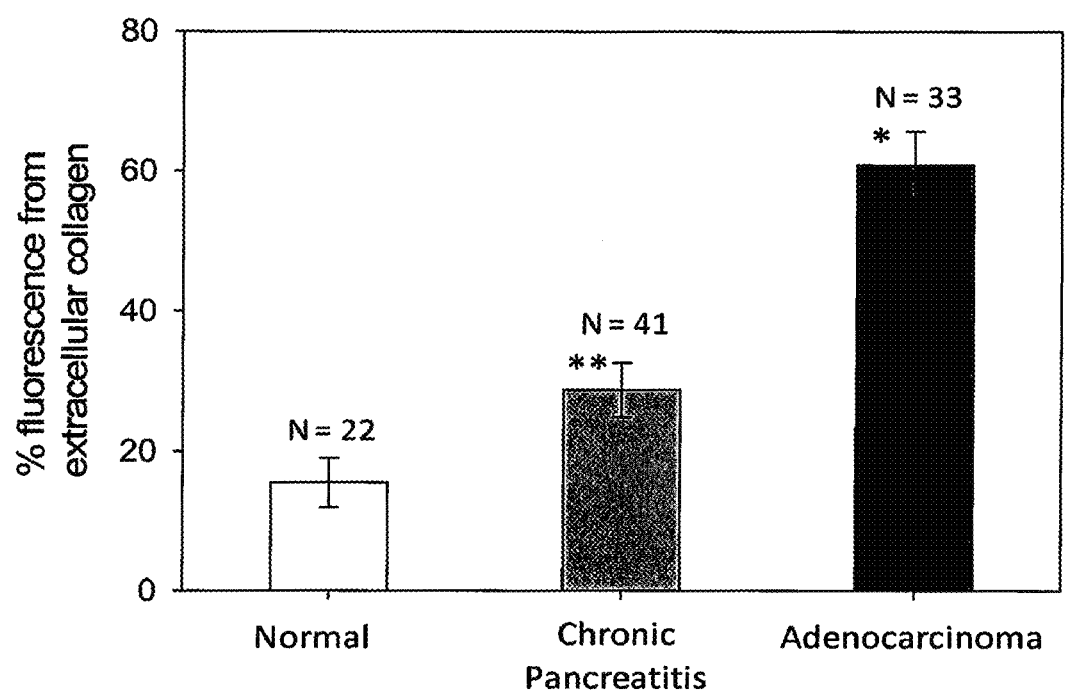
FIG. 14b is a bar graph depicting extracted percentage contributions of extracellular collagen to intrinsic fluorescence spectra of normal pancreatic tissue (N=22 spectra), chronic pancreatitis (N=41 spectra), and pancreatic adenocarcinoma (N=33 spectra) which shows differences that were statistically significant for distinguishing adenocarcinoma from normal pancreatic tissue as well as distinguishing adenocarcinoma from chronic pancreatitis (*, $p<2\times10^{-5}$ from Wilcoxon rank-sum tests) and differences were also statistically significant for distinguishing chronic pancreatitis from normal pancreatic tissue (**, $p<5\times10^{-2}$ from Wilcoxon rank-sum test), among other things, in connection with Illustration VI.

FIG. 14$a$ shows the cellular nuclear dilation factor $L/L_o$ extracted from the PTI model for each pancreatic tissue type. The mean±standard error values of $L/L_o$ extracted for normal pancreatic tissue, chronic pancreatitis, and pancreatic adenocarcinoma were 1.03±0.01, 1.05±0.02, and 1.26±0.02, respectively. The extracted parameter $L/L_o$ can distinguish between adenocarcinoma and normal pancreatic tissue, as well as between adenocarcinoma and chronic pancreatitis ($p<2\times10^{-9}$ from Wilcoxon rank-sum tests). This result is consistent with the larger average cellular nuclear diameters found in histopathological analysis of pancreatic adenocarcinoma relative to normal pancreatic tissue and chronic pancreatitis.

Figure 15:
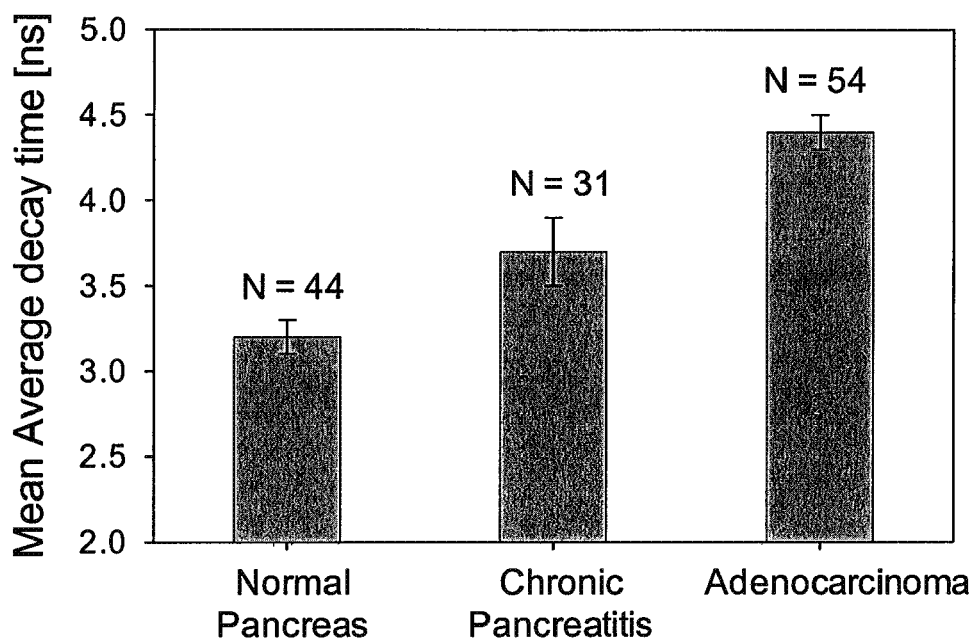
FIG. 15 is a bar graph depicting the mean average decay times for different pancreatic tissue types in connection with Illustration VII.

FIG. 14$b$ shows the percentage contribution of extracellular collagen to the intrinsic fluorescence of normal pancreatic tissue, chronic pancreatitis, and pancreatic adenocarcinoma. The mean±standard error values of the percent contributions of extracellular collagen fluorescence to the spectra of normal pancreatic tissue, pancreatitis, and adenocarcinoma were 15.5±3.5, 28.7±3.8, and 60.9±4.8, respectively. The results shown in FIG. 15 suggest that the percentage contribution of extracellular collagen to the intrinsic fluorescence is potentially useful (*, $p<2\times10^{-5}$ from Wilcoxon rank-sum tests) for distinguishing adenocarcinoma from normal pancreatic tissue, as well as distinguishing adenocarcinoma from chronic pancreatitis. FIG. 15 also shows that the percentage contribution of extracellular collagen to the intrinsic fluorescence is potentially useful (**, $p<5\times10^{-2}$ from Wilcoxon rank-sum test) for distinguishing chronic pancreatitis from normal pancreatic tissue. These results agree with qualitative histopathological observation and hydroxyproline content analysis, both of which have revealed increases in the amount of collagen found in chronic pancreatitis and pancreatic adenocarcinoma, relative to normal pancreatic tissue.

5. Discussion

The results shown in FIGS. 13 and 14$a,b$ suggest that reflectance and fluorescence spectroscopies have the potential to distinguish among pancreatic tissue types, including normal pancreatic tissues, chronic pancreatitis, and pancreatic adenocarcinoma, using biophysical tissue parameters extracted from the data via the PTI model of light propagation. The relevant biophysical parameters for distinguishing the different pancreatic tissue types were the nuclear dilation factor $L/L_o$ and the percentage contribution of extracellular collagen to the intrinsic fluorescence. The observed increase in the nuclear dilation factor $L/L_o$ for adenocarcinoma, relative to normal pancreatic tissue and chronic pancreatitis, is in agreement with the findings of histopathology that the mean cellular nuclear diameter is larger in pancreatic adenocarcinoma than in normal pancreatic tissue and chronic pancreatitis. The increased percentage contributions of extracellular collagen to the intrinsic fluorescence for adenocarcinoma and chronic pancreatitis (relative to normal pancreatic tissue) are in agreement with studies demonstrating that there is increased collagen content in both pancreatic adenocarcinoma and tumor-associated chronic pancreatitis, relative to normal pancreatic tissue.

Since different source fibers were used for reflectance and fluorescence measurements, the light paths of the detected reflectance and fluorescence photons likely interrogated slightly different regions of each tissue site. However, since the reflectance and fluorescence photons were both collected by the same detector fiber, and all three fibers were positioned adjacent to each other in a triangular geometry, we used Monte Carlo simulations to estimate that the majority of reflectance and fluorescence photons collected at a given tissue site visited roughly the same (~1 mm$^3$) region of tissue.

The PTI model reported here does not make use of the hemoglobin concentration and blood-oxygen saturation parameters extracted from the reflectance fits. Since the measurements used for training the PTI model in this study were all obtained ex vivo, much of the hemoglobin absorption information obtained from these measurements is likely most directly related to the amount of blood that drained from each tissue sample and the time that each sample was exposed to air prior to measurement. We note that the blood absorption features present in the measured reflectance spectra were likely similar for measurements made on patients who underwent either type of pancreatic surgery (Whipple procedure or distal pancreatectomy). This is a reasonable assumption because in the distal pancreatectomy procedure, the splenic artery was divided early, producing a level of ischemia that was likely similar to that associated with the Whipple surgery.

In an in vivo setting, we expect to see changes in the measured reflectance spectra that can be linked to differences in the vasculature and blood oxygenation (and hence, the hemoglobin absorption) of pancreatic adenocarcinoma, chronic pancreatitis, and normal pancreatic tissue. We also expect the PTI model to be capable of describing these changes in terms of the total hemoglobin concentration, blood-oxygen saturation, and mean blood vessel radius, as well as the possible addition of a variable to represent the packaging of hemoglobin into erythrocytes. In preparation for future in vivo studies, we are working to further refine the PTI model and examine in greater detail the effect of the hemoglobin absorption parameters on the modeled reflectance. We do not anticipate that the accuracy of the PTI model will be significantly affected by the transition to an in vivo setting, since the model can account for increased levels of absorption due to blood. Thus, the results reported in this study illustrate the potential of the PTI model to address the clinical need for accurate detection of pancreatic adenocarcinoma in the setting of chronic pancreatitis. An optical sensing technique involving the PTI model could potentially be employed in a clinical setting to guide EUS-FNA biopsy.

6. Conclusions

In this study, we demonstrate the first-ever use of a photon-tissue interaction (PTI) model to fit individual reflectance and fluorescence spectra from human pancreatic tissues, among other things. The best fits of the PTI model to the optical spectra extracted diagnostically-relevant biophysical parameters. The nuclear dilation factor was extracted from the PTI reflectance model, and the percent contribution of extracellular collagen to the intrinsic fluorescence was extracted from the PTI fluorescence model. Both of these parameters were statistically significant for distinguishing pancreatic adenocarcinoma from normal pancreatic tissue, as well as for distinguishing adenocarcinoma from chronic pancreatitis. Furthermore, the percent contribution of extracellular collagen to the intrinsic fluorescence was also statistically significant for distinguishing chronic pancreatitis from normal pancreatic tissue. These results indicate that optical spectroscopy involving a photon-tissue interaction model has the potential to quantitatively distinguish between different pancreatic tissue types and to provide an inroad toward addressing the clinical need for accurate detection of early-stage pancreatic cancer.

Illustration VII

1. Introduction

Data described herein were acquired with a RFLS constructed as described herein, such as the exemplary system 10. See also the following peer-reviewed publications: M. Chandra, J. Scheiman, D. Simeone, B. McKenna, J. Purdy, and M.-A. Mycek, "Spectral areas and ratios classifier algorithm for pancreatic tissue classification using optical spectroscopy," J. Biomed. Opt. 15, 010514 (2010); M. Chandra, J. Scheiman, D. Heidt, D. Simeone, B. McKenna, and M.-A. Mycek, "Probing Pancreatic Disease using Tissue Optical Spectroscopy," J. Biomed. Opt. 12, 060501 (2007); and M. Chandra, D. Heidt, D. Simeone, B. McKenna, J. Scheiman, and M.-A. Mycek, "Pancreatic tissue assessment using fluorescence and reflectance spectroscopy," Proc. SPIE 6628, 66281R (2007).

2. Methods

Overall, 231 measurements from 116 tissue sites (normal pancreas, chronic pancreatitis, adenocarcinoma) of 18 patients were acquired with RFLS. However, eight of these measurements were excluded, either because the ratio of the reflectance at 550 nm was less than 10% of that at 650 nm, or because the fluorescence signal-to-noise ratio was less than 25. The remaining wavelength-resolved reflectance and fluorescence data was subdivided into two main sets as described below.

A data set A for the first 9 patients consists of 50 sites (11 normal pancreas, 22 chronic pancreatitis, 17 adenocarcinoma) and 96 measurements (22 normal pancreas, 41 chronic pancreatitis, 33 adenocarcinoma).

A data set B for the remaining 9 patients consists of 66 sites (33 normal pancreas, 16 chronic pancreatitis, 17 adenocarcinoma) and 127 measurements (61 normal pancreas, 32 chronic pancreatitis, 34 adenocarcinoma).

2.1 Time-Resolved Fluorescence Data

The time-resolved fluorescence data was divided into two different subsets. The first subset includes data acquired without the long-pass filter, in which all wavelengths from 360-700 nm were used, and consists of 8 patients, 29 sites (18 normal pancreas, 9 chronic pancreatitis, 2 adenocarcinoma) and 56 measurements (34 normal pancreas, 18 chronic pancreatitis, 4 adenocarcinoma). The second subset includes data acquired with the long-pass filter, in which only wavelengths from 500-760 nm were used, and consists of 10 patients, 66 sites (24 normal pancreas, 15 chronic pancreatitis, 27 adenocarcinoma) and 128 measurements (44 normal pancreas, 30 chronic pancreatitis, 54 adenocarcinoma).

A mean average decay time was extracted from each time-resolved fluorescence decay curve for the above subsets of the pancreatic tissue data, by fitting each decay curve to a tri-exponential decay function of the form $A_1 e^{-t/\tau_1} + A_2 e^{-t/\tau_2} + A_3 e^{-t/\tau_3}$, extracting the values of $A_1, A_2, A_3, \tau_1, \tau_2$, and $\tau_3$ from an optimal fit, and then calculating the mean average decay time $\tau_{avg}$ from the equation:

$$\tau_{avg} = [(A_1\tau_1^2) + (A_2\tau_2^2) + (A_3\tau_3^2)]/[(A_1\tau_1) + (A_2\tau_2) + (A_3\tau_3)]. \quad (16)$$

Figure 16:
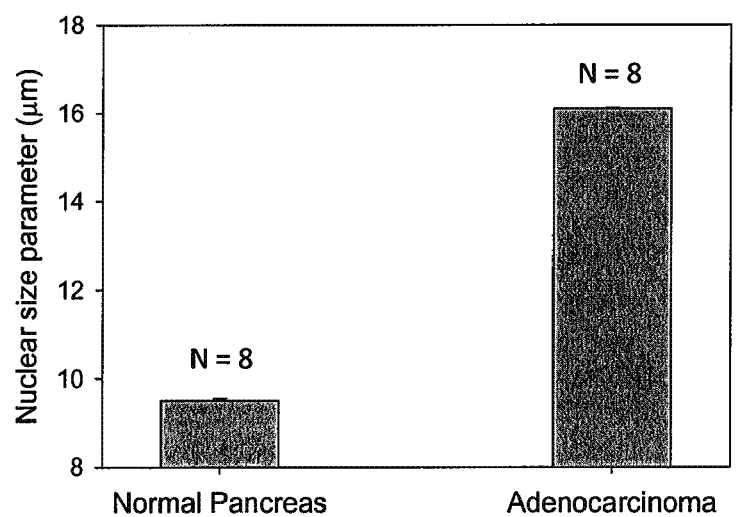
FIG. 16 is a bar graph illustrating the nuclear size parameter extracted from PTI2 reflectance model for normal pancreas (eight spectra) and adenocarcinoma (eight spectra) in connection with Illustration VII.
Figure 17:
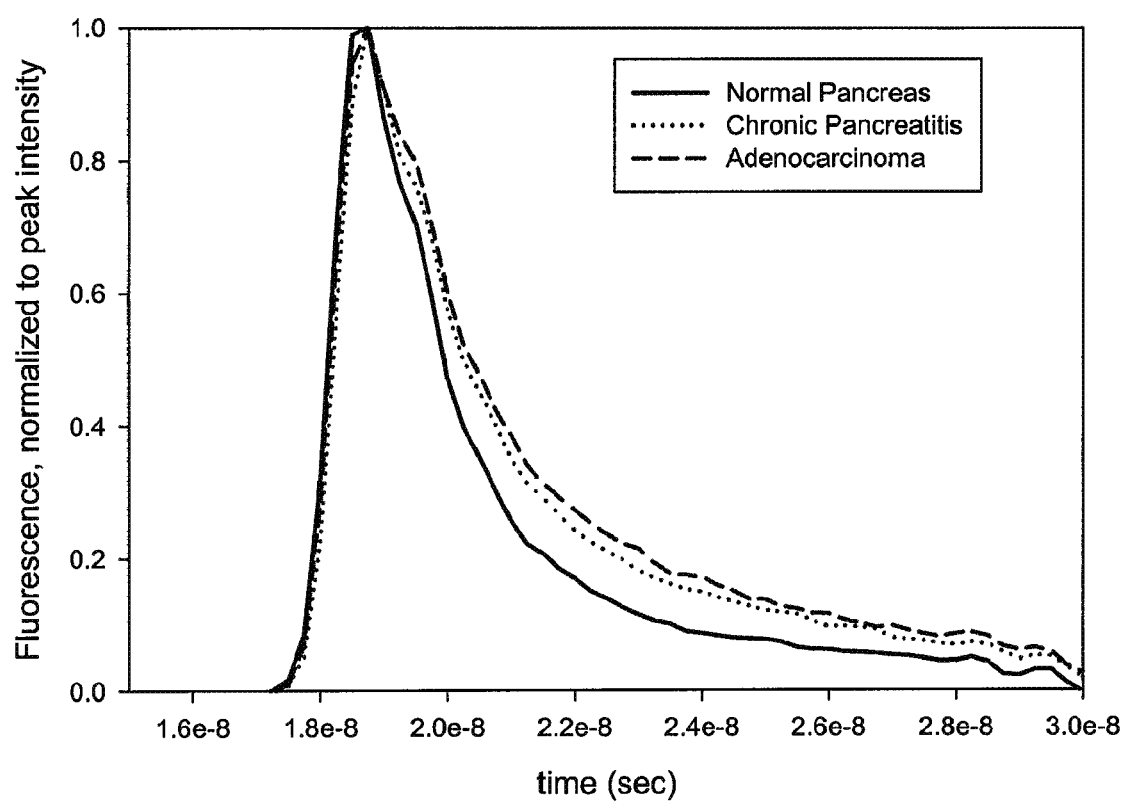
FIG. 17 illustrates representative time-resolved fluorescence decay curves from normal pancreatic tissue, chronic pancreatitis, and adenocarcinoma with respect to Illustration VII.

The value of the mean average decay time parameter was found to be significantly different ($p < 5 \times 10^{-2}$) for distinguishing between normal pancreas, chronic pancreatitis, and adenocarcinoma, as shown by the following Table 36 and bar graphs shown in FIGS. 15 and 16. FIG. 17 illustrates representative time-resolved fluorescence decay curves from normal pancreatic tissue, chronic pancreatitis, and adenocarcinoma.

TABLE 36 p-values for using mean average decay time to distinguish between pancreatic tissue types

| Classification | p-value from Wilcoxon rank-sum test |
|---|---|
| Malignant pancreatic tissue (adenocarcinoma) vs benign pancreatic tissue (normal pancreas and chronic pancreatitis) | $p = 1 \times 10^{-9}$ |
| Adenocarcinoma vs normal pancreas | $p = 4 \times 10^{-10}$ |
| Adenocarcinoma vs chronic pancreatitis | $p = 3 \times 10^{-4}$ |
| Chronic pancreatitis vs normal pancreas | $p = 4 \times 10^{-3}$ |

*All p-values reported here are statistically significant for classification

Illustration VIII

1. Introduction

Data described herein were acquired with a RFLS constructed as described herein, such as the exemplary system 10.

2. Methods for Tissue Classification

Principal Component Analysis (PCA) and Photon-Tissue Interaction algorithms were employed to extract classification parameters from the measured pancreatic tissue reflectance and fluorescence spectra.

PCA was undertaken on the fluorescence and reflectance spectral data separately. Two different sets of inputs were employed for classification. In the PCA 99% method, the first seven fluorescence and first five reflectance Principal Component (PC) scores were employed as classification variables that were input to a Generalized Estimating Equations (GEE) algorithm. These PCs explained 99% of the variance in the data. In the PCA 95% method, the first three fluorescence and first three reflectance PC scores were employed as classification variables that were input to the GEE algorithm. These PCs explained 95% of the variance in the data.

A Photon-Tissue Interaction model referred to as the "PTI1" model is described herein and in the following references: R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009) and R. H. Wilson, M. Chandra, L.-C. Chen, W. Lloyd, J. Scheiman, D. Simeone, J. Purdy, B. McKenna, and M.-A. Mycek, "Photon-tissue interaction model enables quantitative optical analysis of human pancreatic tissues" (submitted to Opt. Express).

The PTI1 model fits mathematical models of reflectance and fluorescence to individual measured wavelength-resolved spectra, and values of the nuclear diameter (L) and percentage contributions of collagen, NADH, and FAD to the fluorescence (% COLL, % NADH, % FAD) are extracted from the best fits. Another model, the "PTI1b" model, behaves in the same way as PTI1, except that an additional parameter is extracted from the best fit of the reflectance model to each measured wavelength-resolved reflectance spectrum. This additional parameter is the nuclear refractive index ($n_s$), which is then used along with L, % COLL, % NADH, and % FAD in the classification algorithms.

In order to classify a given spectrum as "normal," "chronic pancreatitis," or "adenocarcinoma," a GEE model was employed. The GEE model was chosen because it can correct the acquired data set for intra-patient correlations (classification algorithm errors caused by the fact that there were multiple spectra acquired from each patient).

Prior to analysis with the classification algorithms, the following tissue sites were flagged as "outliers" and removed from the data set: (1) sites where the reflectance at 550 nm was less than 20% of that at 650 nm, (2) sites where the fluorescence signal-to-noise ratio was less than 30, and (3) sites where the two measurements were very different from each other.

3. Results

For the data analysis reported here, the initial data set (Data Set (A+B)) consisted of 116 tissue sites from 18 patients, and the data set used for analysis (following outlier removal) contained 105 tissue sites from 18 patients (9% of the sites were removed). Preliminary results of the GEE algorithm with parameters extracted from the PCA and PTI models are shown in Table 37 below:

TABLE 37

GEE tissue classification results for PCA and PTI:

| Method | Sensitivity | Specificity | PPV | NPV |
|---|---|---|---|---|
| For distinguishing malignant pancreatic tissue (adenocarcinoma) from benign pancreatic tissue (normal and chronic pancreatitis): | | | | |
| PCA 99% | 87% | 88% | 74% | 94% |
| PCA 95% | 90% | 80% | 64% | 95% |
| PTI 1 | 83% | 87% | 71% | 93% |
| PTI 1b | 87% | 85% | 70% | 94% |
| For distinguishing pancreatic adenocarcinoma from chronic pancreatitis: | | | | |
| PCA 99% | 53% | 69% | 59% | 63% |
| PCA 95% | 80% | 60% | 63% | 78% |
| PTI 1 | 80% | 77% | 75% | 82% |
| PTI 1b | 90% | 74% | 75% | 90% |

PCA 99% = Principal Component Analysis model using PCs that explain 99% of the variance in the data
PCA 95% = Principal Component Analysis model using PCs that explain 95% of the variance in the data
PTI 1 = Photon-Tissue Interaction model reported in manuscript submitted to Optics Express (Mycek_PTI_6-2010-OE.vf.doc)
PTI 1b = same as PTI 1, except that an additional parameter (the nuclear refractive index) was extracted from the best fit of the model to each spectrum The previously-published PTI1 reflectance model (see above) uses an average measured "canonical normal" reflectance spectrum as a starting point. Another PTI reflectance model (referred to as "PTI2") has been developed and is disclosed herein. The PTI2 reflectance model employs a "direct fitting" approach in which each measured reflectance spectrum is fit directly with an empirical equation for the reflectance as a function of the tissue and probe properties. Therefore, the PTI2 reflectance model does not use a "canonical normal" spectrum as a starting point, so it does not require the use of parameters related to the "canonical normal" spectrum (such as for example, the hemoglobin concentration and blood oxygen saturation of the "canonical normal" spectrum). The PTI2 model also accounts for the packaging of hemoglobin into red blood cells; the PTI1 and PTI1b models did not account for this effect.

A version of the PTI2 model was run for eight normal pancreas reflectance spectra and eight adenocarcinoma reflectance spectra. The free parameters were the nuclear diameter, oxy-hemoglobin concentration, deoxy-hemoglobin concentration, beta-carotene concentration, and pigment packaging factor; the PTI1 and PTI1b models did not include the beta-carotene concentration or pigment packaging factor.

Figure 18:
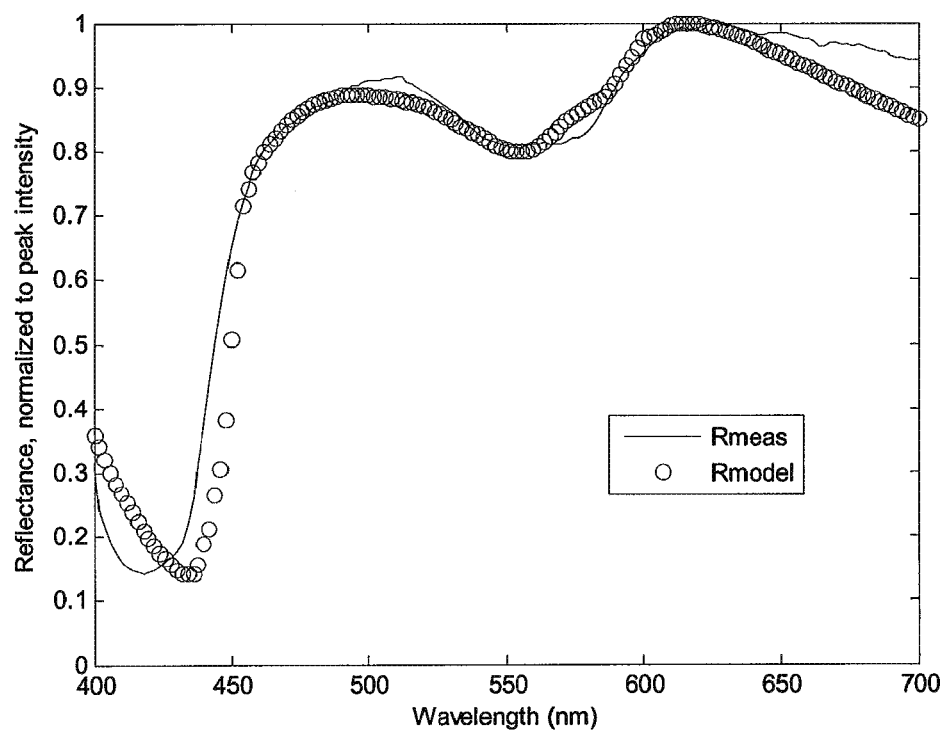
FIGS. 18 and 19 provide representative graphical plots fitting the PTI2 model to the adenocarcinoma spectrum (FIG. 18) and the normal pancreas reflectance spectrum (FIG. 19) in connection with some embodiments of the invention and Illustration VIII.
Figure 19:
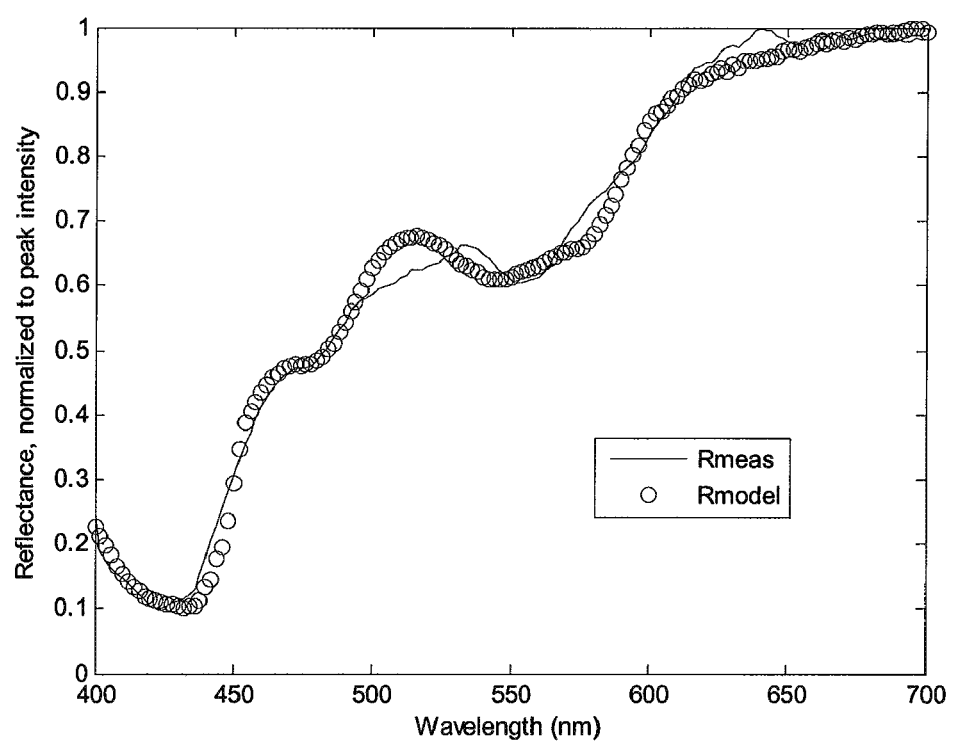

Representative fits of the PTI2 model, as shown in FIGS. 18 and 19, to the data show good agreement, and the extracted (mean±standard error) nuclear diameter was 16.1 μm±0.01 μm for pancreatic adenocarcinoma, as compared to 9.50 μm±0.05 μm for normal pancreas. These results suggest that the PTI2 model has the potential to provide accurate fits, including in the regions where hemoglobin absorption is high (near about 420 nm and near about 550 nm), which may be of important for in vivo work, where the presence of blood will likely be more significant. These results also show that the PTI2 model can extract diagnostically important information about the changes in nuclear size associated with adenocarcinoma, relative to normal pancreatic tissue. The GEE tissue classification outcomes for Data Set (A+B) are summarized in Table 37 below.

TABLE 37

GEE tissue classification results including PTI2

| Method | Sensitivity | Specificity | PPV | NPV |
|---|---|---|---|---|
| For distinguishing malignant pancreatic tissue (adenocarcinoma) from benign pancreatic tissue (normal and chronic pancreatitis): | | | | |
| PCA 99% | 87% | 88% | 74% | 94% |
| PCA 95% | 90% | 80% | 64% | 95% |
| PTI 1 | 83% | 87% | 71% | 93% |
| PTI 1b | 87% | 85% | 70% | 94% |
| PTI 2 | 87% | 88% | 74% | 94% |
| PTI 2b | 87% | 87% | 72% | 94% |
| For distinguishing pancreatic adenocarcinoma from chronic pancreatitis: | | | | |
| PCA 99% | 53% | 69% | 59% | 63% |
| PCA 95% | 80% | 60% | 63% | 78% |
| PTI 1 | 80% | 77% | 75% | 82% |
| PTI 1b | 90% | 74% | 75% | 90% |
| PTI 2 | 87% | 74% | 74% | 87% |
| PTI 2b | 83% | 74% | 74% | 84% |

PCA 99% = Principal Component Analysis model using PCs that explain 99% of the variance in the data
PCA 95% = Principal Component Analysis model using PCs that explain 95% of the variance in the data
PTI 1 = Photon-Tissue Interaction model reported in manuscript submitted to Optics Express (incorporated herein)
PTI 1b = same as PTI 1, except that an additional parameter (the nuclear refractive index) was extracted from the best fit of the model to each spectrum
PTI 2 = "Direct fit" Photon-Tissue Interaction model described herein and in references incorporated herein.
PTI 2b = same as PTI 2, except that an additional parameter (the nuclear refractive index) was extracted from the best fit of the model to each spectrum Illustration IX 1. Introduction As discussed above, an optical spectroscopic system and method has been developed and employed for classification of human pancreatic tissues. Further examples of the embodiments of the invention are discussed in the following Illustration, including alternatives on classification steps discussed above.

In these examples, prototype clinically-compatible instrumentation was employed to acquire steady-state reflectance, steady-state fluorescence, and time-resolved fluorescence from human pancreatic tissues. Mathematical models of the steady-state optical data were employed to extract diagnostically-useful tissue parameters. The tissue parameters extracted from the steady-state reflectance and fluorescence data were input into a tissue classification algorithm that employed Generalized Estimating Equations to account for intra-patient correlations in the data. Two different data sets of time-resolved fluorescence measurements were obtained. These two data sets had different methods of acquisition ("No LP" and "With LP"). The measured time-resolved fluorescence data were analyzed with a set of mathematical methods. The methods included a tri-exponential decay model, a stretched exponential decay model, a bi-stretched exponential decay model, a Laguerre deconvolution model, and a phasor analysis algorithm. For both data sets, the aforementioned mathematical methods were shown to extract statistically-significant parameters for distinguishing between different pancreatic tissue types (normal, pancreatitis, adenocarcinoma), both by measurement and by site.

All data described herein were acquired with a prototype Reflectance and Fluorescence Lifetime Spectrometer (RFLS), as described herein.

Two different sets of time-resolved fluorescence data were acquired (as shown in Table 38):

"No LP": Time-resolved fluorescence was collected from wavelengths of 360 nm onward;

"With LP": Time-resolved fluorescence was collected from wavelengths of 500 nm onward because long-pass (LP) filter was placed in front of the detector; and Time-resolved fluorescence measurements for which the peak signal of either the tissue measurement or the corresponding instrument response function exceeded 0.5 V or fell below 0.15 V were excluded from the data sets.

TABLE 38

Time-resolved fluorescence data sets from human pancreatic tissues.

| Data Set | Patients | Sites | Measurements |
|---|---|---|---|
| No LP | 6 | 8 normal | 16 normal |
| | | 17 pancreatitis | 29 pancreatitis |
| With LP | 10 | 29 normal | 52 normal |
| | | 16 pancreatitis | 31 pancreatitis |
| | | 27 adenocarcinoma | 52 adenocarcinoma |

2. Data Analysis Methods: Tissue Classification Algorithm

A tissue classification algorithm for optical data was developed in accordance with the protocol outlined in the flow charts below. The algorithm described and shown in FIGS. 20 and 21 is an alternative version of those discussed above.

Figure 20:
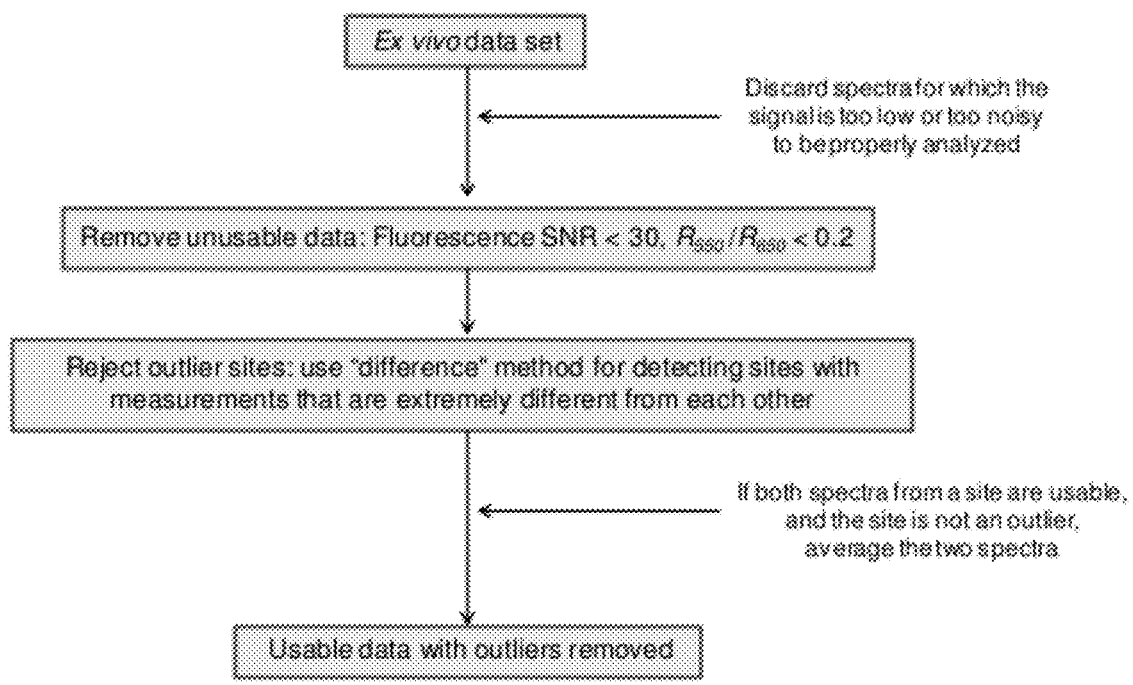
FIGS. 20 and 21 provide flow diagrams illustrating two parts (Parts 1 and 2) of a data analysis protocol for a tissue classification algorithm in accordance with some embodiments of the invention.
Figure 21:
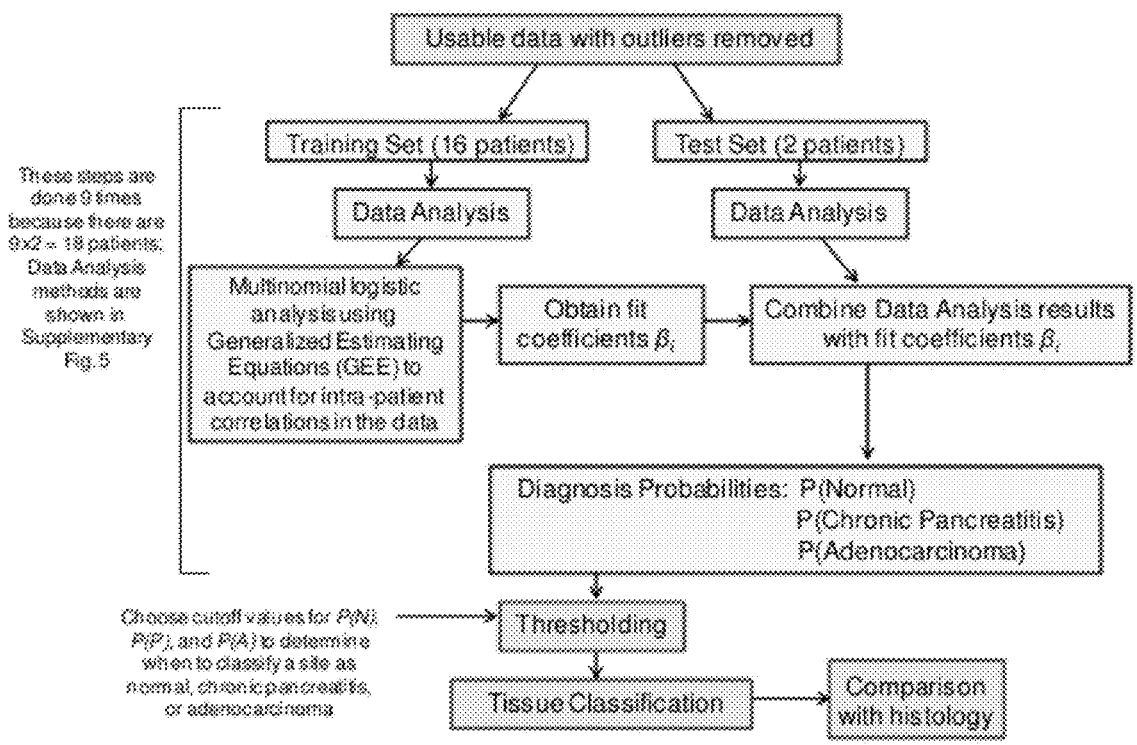
Figure 22:
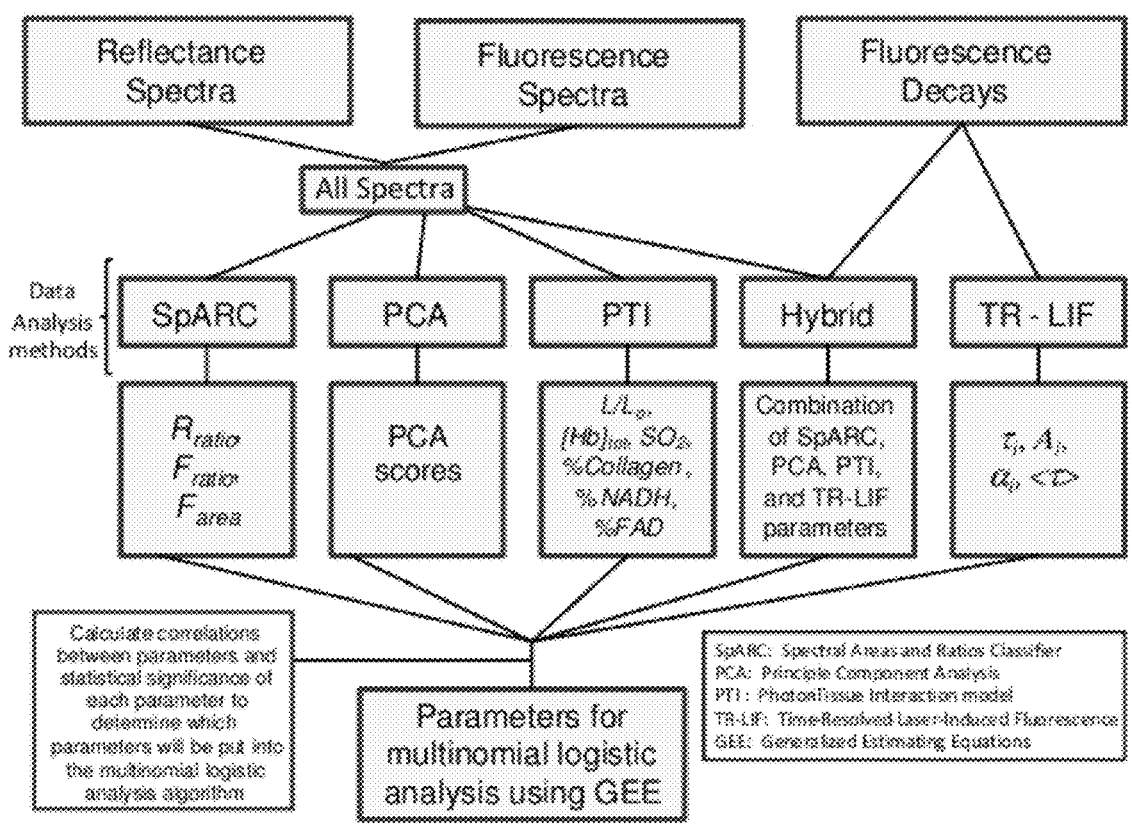
FIG. 22 provides a flow diagram illustrating data analysis methods for optical data acquired from human pancreatic tissues according to some embodiments of the invention.

As shown in FIG. 20, from the entire ex vivo data set, spectra are removed if their signal is too low or too noisy for proper analysis. Then, outlier sites are removed via an algorithm that determines the degree of difference between pairs of measurements taken from the same site. For sites with two usable spectra, the two spectra are averaged. After Part 1 of the protocol shown in FIG. 20 is completed, the remaining data is split into training sets (16 patients) and testing sets (2 patients). This step is performed nine times, so that data from each of the 18 patients will be included in one of the testing sets. Data analysis of the testing and training sets extracts tissue parameters for every site in both sets. The parameters extracted from the training set are put into a multinomial logistic analysis method using Generalized Estimating Equations (GEE) to account for intra-patient correlations in the data. The resulting fit coefficients $\beta_i$ are combined with the data analysis results from the testing set to provide diagnostic probabilities of adenocarcinoma, normal pancreatic tissue, and pancreatitis. Thresholds are placed on these probabilities to determine when to classify a given site as a given tissue type. The results of the classification algorithm are compared with those of histology to test the classification accuracy. Each data analysis method provides a set of tissue parameters that can then be input into the tissue classification algorithm (FIG. 21, FIG. 22). Multinomial logistic analysis with Generalized Estimating Equations (GEE) is employed to account for intra-patient correlations in the data.

2.2 Time-Resolved Fluorescence Data

Individual time-resolved fluorescence decay curves were analyzed with a variety of mathematical modeling techniques, including tri-exponential decay, stretched exponential decay, bi-stretched exponential decay, Laguerre deconvolution and phasor analysis. For each mathematical technique, the statistical significance of the extracted parameters was assessed in two ways, that is, using Wilcoxon rank-sum tests for distinguishing between individual measurements from different pancreatic tissue types (normal, pancreatitis, adenocarcinoma), and using Wilcoxon rank-sum tests for distinguishing between individual sites from different pancreatic tissue types (normal, pancreatitis, adenocarcinoma).

3. Results: Pancreatic Tissue Classification Algorithm Including Steady-State and Time-Resolved Optical Data from Human Pancreatic Tissues For the sites that were in both the "With LP" data set and the steady-state data set (26 normal, 15 pancreatitis, 16 adenocarcinoma), the mean lifetime <τ> extracted from the tri-exponential model of the time-resolved data was included alongside steady-state reflectance and fluorescence parameters in a tissue classification algorithm. This algorithm employed a multinomial logistic analysis method using Generalized Estimating Equations (GEE) in order to account for intra-patient correlations in the measured data.

The preliminary results of the tissue classification algorithm are shown below in Table 39. These results suggest that including time-resolved data has the potential to provide higher sensitivity for classification of adenocarcinoma as well as significantly improved accuracy for distinguishing pancreatitis from normal pancreatic tissue.

TABLE 39

Malignant (adenocarcinoma, 26 sites) vs. Benign (normal and pancreatitis, 41 sites)

| | |
|---|---|
| Sensitivity | 92.3% |
| Specificity | 82.9% |
| Positive Predictive Value (PPV) | 77.4% |
| Negative Predictive Value (NPV) | 94.4% |

Adenocarcinoma (26 sites) vs. Pancreatitis (15 sites)

| | |
|---|---|
| Sensitivity | 92.3% |
| Specificity | 73.3% |
| Positive Predictive Value (PPV) | 85.7% |
| Negative Predictive Value (NPV) | 84.6% |

Pancreatitis (15 sites) vs. Normal (26 sites)

| | |
|---|---|
| Sensitivity | 93.3% |
| Specificity | 84.6% |
| Positive Predictive Value (PPV) | 77.8% |
| Negative Predictive Value (NPV) | 95.7% |

4. Conclusions

The following conclusions relate to the examples herein as well as include support for the embodiments discussed above. In particular, with respect to this Illustration the tissue classification algorithm results from human pancreatic tissues supporting the following findings. With respect to steady-state optical spectroscopy, it was found that the algorithms have the potential to accurately distinguish pancreatic cancer from normal pancreatic tissue and chronic pancreatitis; different data analysis methods have different merits, depending on the specific biomedical problem at hand; a hybrid method (combining PTI and PCA) was the most accurate overall and results were Malignant (adenocarcinoma) vs. benign (normal and pancreatitis): Sensitivity=87.5%, Specificity=89.0%, PPV=77.8%, NPV=94.2% and Adenocarcinoma vs. pancreatitis: Sensitivity=87.5%, Specificity=79.4%, PPV=80.0%, NPV=87.1%); and sensitivity and NPV can be increased using any of the data analysis methods, but there is a corresponding drop in specificity and PPV, among other things.

EXAMPLE 1

Malignant Vs. Benign Using Hybrid Method with Manual Thresholds Yields P(A)>0.23 and P(N)<0.26: Sensitivity=90.6%, Specificity=86.3%, PPV=74.4%, NPV=95.5%; and

EXAMPLE 2

Adenocarcinoma Vs. Pancreatitis Using PTI Method with Manual Thresholds Yields P(A)>0.25 and P(P)<0.5: Sensitivity=90.6%, Specificity=70.6%, PPV=74.4%, NPV=88.9%

With respect to time-resolved optical data, it was found that time-resolved optical spectroscopy has the potential to accurately distinguish pancreatic cancer from normal pancreatic tissue and chronic pancreatitis. Using the hybrid method (combining TR, PTI, and PCA) the classification results were as follows: Malignant (adenocarcinoma) vs. benign (normal and pancreatitis): Sensitivity=92.3%, Specificity=82.9%, PPV=77.4%, NPV=94.4%, Adenocarcinoma vs. pancreatitis: Sensitivity=92.3%, Specificity=73.3%, PPV=85.7%, NPV=84.6%, and Pancreatitis vs. normal: Sensitivity=93.3%, Specificity=84.6%, PPV=77.8%, NPV=95.7%. The mean lifetime parameter extracted from the tri-exponential decay model for the "With LP" data set was incorporated into a tissue classification algorithm that employed Generalized Estimating Equations to account for intra-patient correlations. Although not to be construed as a limitation, in the examples discussed herein the addition of time-resolved fluorescence data to the tissue classification algorithm demonstrated the potential to increase the sensitivity of the algorithm for distinguishing adenocarcinoma from benign tissues (normal and pancreatitis), as well as to significantly improve the ability of the algorithm to distinguish between pancreatitis and normal pancreatic tissue.

Illustration X

1. Introduction

An in-depth analysis of the PTI model was performed in accordance with the invention and various embodiments discussed herein. A systematic study of how individual absorption and scattering parameters affect the semi-empirical reflectance equations used in the PTI model was conducted. Then, the manner in which the PTI model is employed to mathematically transform an average measured "canonical normal" pancreatic tissue reflectance spectrum into an accurate model for pancreatitis (by increasing the collagen concentration) and adenocarcinoma (by increasing the collagen concentration and the mean size of the cell nuclei) was analyzed. The PTI model predictions were compared with average measured data from pancreatitis and adenocarcinoma to illustrate the effectiveness of the PTI model at linking changes in specific biophysically-relevant tissue parameters to specific changes in distinct regions of the reflectance spectrum. These systematic tests of the PTI model serve to separate the effects of the individual absorption and scattering parameters on the modeled reflectance. Once the effects of the individual parameters had been characterized in this way, the effect of changing blood content on the extracted tissue parameters was investigated. It became apparent that since the absorption and scattering parameters in the PTI model affect distinct regions of the modeled reflectance spectrum, the extracted scattering parameters remain consistent even for tissue sites at which the two measured spectra appear very different due to blood draining from the tissue over the course of measurement.

2. Experimental Methods 2.1 Instrumentation

Prototype clinically-compatible instrumentation was developed (such as instrumentation as described in M. Chandra, J. Scheiman, D. Simeone, B. McKenna, J. Purdy, and M.-A. Mycek, "Spectral areas and ratios classifier algorithm for pancreatic tissue classification using optical spectroscopy," J. Biomed. Opt. 15, 010514 (2010); M. Chandra, K. Vishwanath, G. D. Fichter, E. Liao, S. J. Hollister, and M.-A. Mycek, "Quantitative molecular sensing in biological tissues: an approach to non-invasive optical characterization," Opt. Express 14, 6157-6171 (2006); and M. Chandra, J. Scheiman, D. Heidt, D. Simeone, B. McKenna, and M.-A. Mycek, "Probing pancreatic disease using tissue optical spectroscopy," J. Biomed. Opt. 12, 060501 (2007), all of which are incorporated herein by reference). This instrumentation was employed to acquire reflectance spectra from human pancreatic tissues within 30 minutes of resection during pancreatic surgery at the University of Michigan (U-M) Medical Center. A tungsten-halogen lamp was employed as the reflectance source and light from the lamp was directed onto the tissue surface with an optical fiber of 600 µm core diameter. Reflectance photons were collected by a separate 600 µm diameter detector fiber placed adjacent to the source fiber. Light from the detector fiber was directed toward a spectrograph-coupled ICCD camera for spectral detection.

2.2 Data Acquisition Protocol

Optical data was acquired from each of nine patients within 30 minutes of excision of the pancreatic tissue. Prior to measurement, excess blood was wiped off of the tissue with gauze. The on-site pathologist then identified sites of interest on the excised tissue and the optical probe was placed on those tissue sites for data acquisition. Some of these sites were beneath the surface of the tissue; in these cases the tissue was cut in order to provide access to the fiber-probe. At each site, the probe was held in position by hand and its position was monitored by the pathologist and the person taking the measurement. Two sets of measurements of steady-state reflectance, steady-state fluorescence, and time-resolved fluorescence decay were made at each site without removing the probe. Each set of measurements took approximately 40 seconds to obtain. After completion of the measurements at a given site, the probe was removed and the pathologist immediately excised a portion of the tissue from that site for histopathologic analysis, which was considered the "gold-standard" for this study. In this manner, optical measurements were obtained at multiple sites from each patient, depending on the size of the resected tissue sample.

Data analysis was performed on sites from which two usable measurements were acquired. Non-usable measurements (fluorescence signal-to-noise ratio<25, or reflectance intensity at 550 nm<10% of that at 650 nm) were discarded. An additional five sites were removed due to artifacts from room lights. The resulting data set contained 42 sites (10 normal, 19 chronic pancreatitis, 13 adenocarcinoma), and since two reflectance measurements were taken at each site, there were a total of 84 measured reflectance spectra.

In this study, the variations in tissue blood content were not experimentally-controlled. Absorption-related variations were observed in the two reflectance spectra acquired at each site, and it was presumed that this variability was caused by changes in the concentration and oxygenation of blood in the freshly-excised tissues. This hypothesis makes sense because variations in tissue blood content are known to occur post-resection and these variations have been shown to impact the measured optical spectra.

3. Systematic Analysis of Photon-Tissue Interaction (PTI) Model

A PTI model using semi-empirical reflectance equations (such as those described herein and in R. H. Wilson, M. Chandra, L.-C. Chen, W. Lloyd, J. Scheiman, D. Simeone, J. Purdy, B. McKenna, and M.-A. Mycek, "Photon-tissue interaction model enables quantitative optical analysis of human pancreatic tissues," Opt. Express 18, 21612-21621 (2010) and R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009), incorporated herein by reference) was employed to extract absorption- and scattering-related tissue parameters (Table 40) from the measured reflectance spectra.

TABLE 40

Tissue parameters that can be extracted by photon-tissue interaction (PTI) model of reflectance.

| Scattering | Absorption |
|---|---|
| Mean diameter of cell nuclei, <L> | Total hemoglobin concentration, $[Hb]_{tot}$ |
| Refractive index of cell nuclei, $n_s$ | Blood-oxygen saturation, $SO_2$ |
| Concentration of collagen fibers, $\rho_c$ | Mean blood vessel radius, $r_{bl}$ |

The starting point of the PTI model is an average measured "canonical normal" reflectance spectrum, $N_{measured}(\lambda)$ obtained by averaging all reflectance measurements from normal tissue sites in the data set. This "canonical normal" spectrum is then mathematically transformed to produce a PTI model spectrum $R_{PTI}(\lambda)$ that can be fit to an individual reflectance measurement of "unknown" tissue type. This mathematical transformation takes the form:

$$R_{PTI}(\lambda) = N_{measured}(\lambda) \frac{R_{empirical}(\lambda)}{N_{empirical}(\lambda)}. \quad (17)$$

In Eq. (17), $R_{empirical}(\lambda)$ and $N_{empirical}(\lambda)$ are semi-empirical equations describing the "unknown" reflectance measurement and the "canonical normal" reflectance, respectively. Both of these semi-empirical equations take the following general form $R(\lambda)$:

$$R(\lambda) = \mu_s'(\lambda) \exp\left(-\frac{C_{corr}\mu_a(\lambda)b}{[C_{corr}(\lambda)\mu_a(\lambda)\mu_s'(\lambda)]^c}\right). \quad (18)$$

In Eq. (18), $\mu_a(\lambda)$ is the tissue absorption coefficient and $\mu_s'(\lambda)$ is the reduced scattering coefficient, defined as $\mu_s'(\lambda) = \mu_s(\lambda)(1-g)$, where g is the anisotropy (set equal to 0.9 here). The variables b and c are related to tissue and fiber-probe properties. Tissue scattering was attributed to cell nuclei (modeled as spheres with mean diameter <L> and refractive index $n_s$) and collagen fibers (modeled as cylinders with concentration $\rho_c$). Tissue absorption was attributed to oxy- and deoxy-hemoglobin, with a correction factor $C_{corr}(\lambda)$ that accounted for the confinement of blood to cylindrical blood vessels with mean radius $r_{bl}$. From each reflectance measurement, a cellular nuclear enlargement factor $L/L_o$ and the total hemoglobin concentration $[Hb]_{tot}$ were extracted. The nuclear enlargement factor was a ratio between the mean (ensemble average) diameter <L> of cell nuclei at a given site and the mean size $L_o$ of normal pancreatic cell nuclei. The value of $L/L_o$ was previously shown to be larger for adenocarcinoma than for normal pancreatic tissue or pancreatitis, a result that agreed with histopathological observation.

Figure 23:
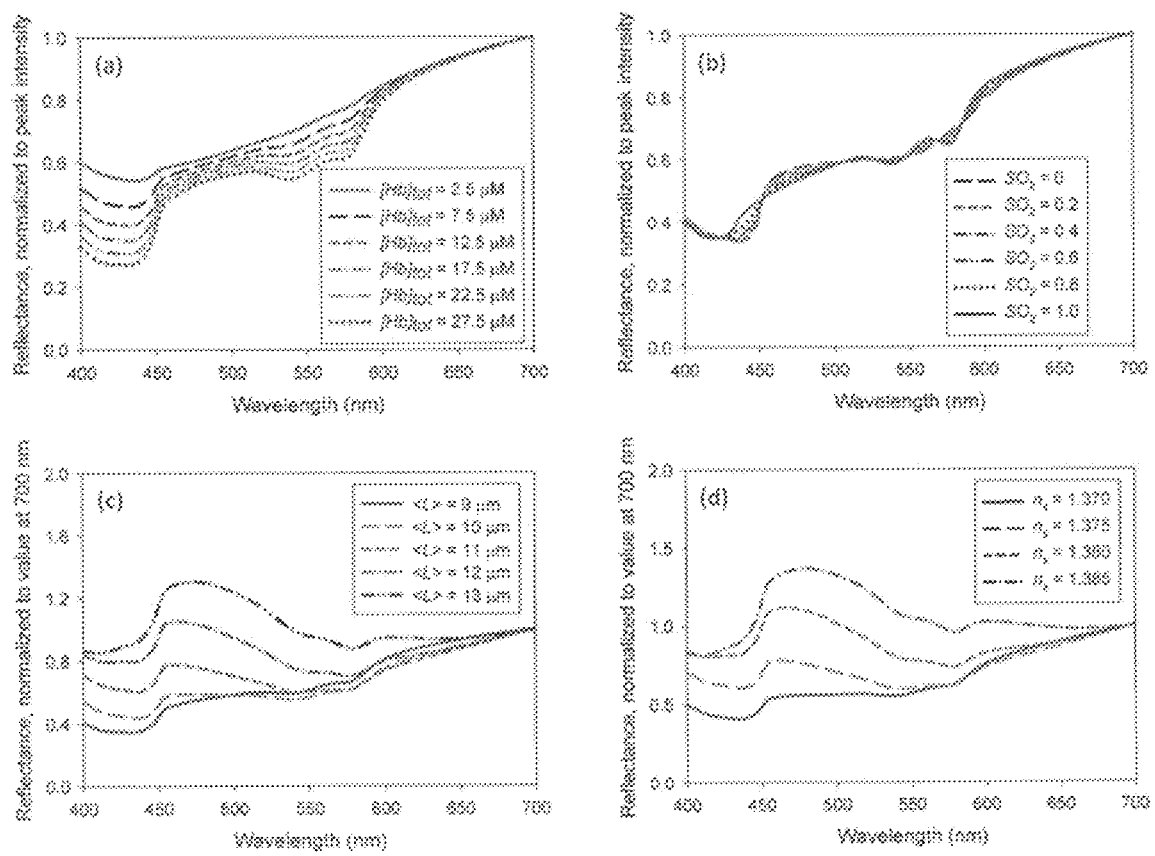
FIG. 23 provides a systematic examination of changes in the semi-empirical reflectance equation when different parameters are varied.

To systematically examine the effect of the different tissue properties on the semi-empirical reflectance equation $R_{empirical}(\lambda)$, the total hemoglobin concentration, blood-oxygen saturation, mean nuclear diameter, and nuclear refractive index were varied individually while all of the remaining parameters were kept constant. FIG. 23 shows the effect of each of these variations. From FIGS. 23(a) and 23(b), it can be seen that changing the hemoglobin concentration and blood oxygenation primarily affects the amplitude of the reflectance from 400-450 nm and from 525-600 nm. FIG. 23(c) shows that changing the mean nuclear diameter has a significant effect on the amplitude of the modeled reflectance in the 450-525 nm range. This result is consistent with the experimentally-observed trend that reflectance spectra from pancreatic adenocarcinoma (which is expected to exhibit enlarged cell nuclei) typically have higher amplitude in the 450-525 nm range than the spectra of normal pancreas or pancreatitis. FIGS. 23(c) and 23(d) both illustrate that changing the tissue scattering properties can affect the slope of the reflectance spectrum between 600 nm and 700 nm. The results in FIG. 23 are consistent with the experimentally-observed trends that reflectance spectra of adenocarcinoma, pancreatitis, and normal pancreatic tissue have different amplitudes in the 450-525 nm wavelength range and different slopes in the 600-700 nm wavelength range. These findings suggest that the semi-empirical reflectance equation (Eq. (18)) is sensible to incorporate into the PTI model because it has the potential to link specific biophysically-relevant tissue parameters to specific trends in the measured reflectance spectra that are related to the progression of pancreatic disease.

Figure 24:
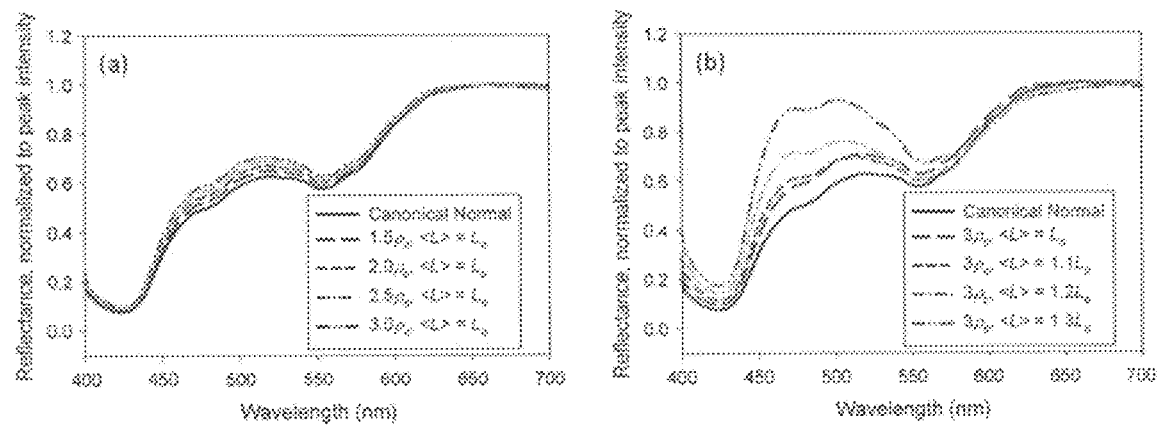
FIG. 24 provides an illustration of the effect of varying the collagen concentration and mean cellular nuclear size in the PTI reflectance model.

FIG. 24 illustrates how Eqs. (17) and (18) can be employed to mathematically transform an average measured "canonical normal" spectrum (obtained here by averaging 20 reflectance measurements from normal pancreatic tissues) into a PTI reflectance model $R_{PTI}(\lambda)$ for pancreatic tissues with different scattering properties. In FIG. 24(a), the concentration $\rho_c$ of the collagen fibers is varied, and in FIG. 24(b), the mean size <L> of the cell nuclei is varied. In both cases, the region of the spectrum from 450-525 nm is most prominently affected.

Figure 25:
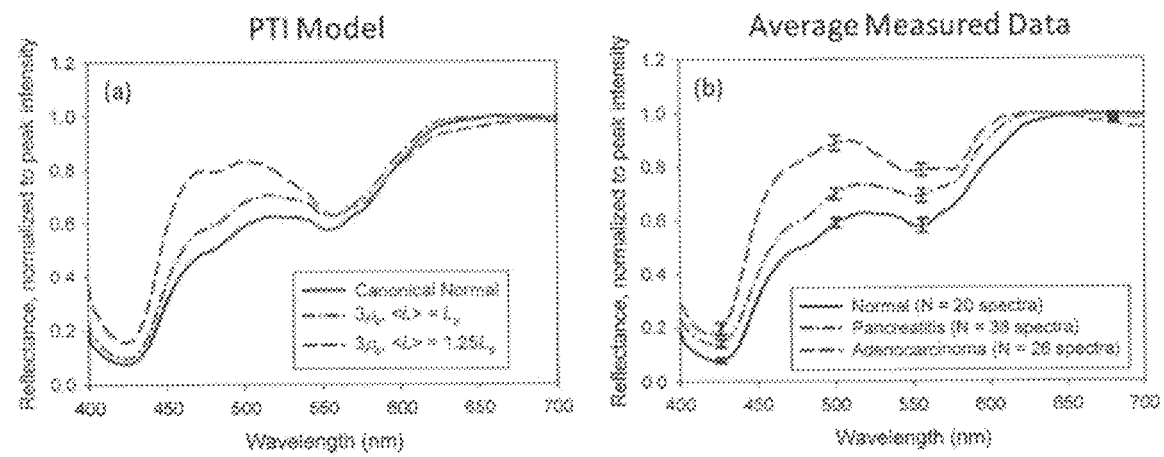
FIG. 25 provides a comparison of the PTI reflectance model for different scattering parameters and average experimentally-measured reflectance data from normal pancreatic tissue, pancreatitis, and adenocarcinoma.

Using FIG. 24 as a guideline, FIG. 25 shows how some key features of the reflectance spectra from the PTI model (FIG. 25(a)) match up with those of average measured reflectance data from pancreatitis and adenocarcinoma (FIG. 25(b)). First, the mean nuclear size is kept constant but the collagen concentration is multiplied by a factor of three, which has been shown in the medical literature to be indicative of both pancreatitis and adenocarcinoma. In this case, the PTI reflectance model (dot-dashed line in FIG. 25(a)) looks similar to the average measured reflectance from pancreatitis (dot-dashed line in FIG. 25(b)). This result is consistent with the observation at histopathology that pancreatitis is characterized by increased extracellular collagen but no significant increase in the mean size of cell nuclei (relative to normal tissue). Next, the concentration of collagen is kept at three times that of normal tissue, but the mean nuclear size <L> is increased from its initial value of $L_o$ to a value of $1.25L_o$. For this larger value of <L>, one can see the similarity between the PTI reflectance model (dashed line in FIG. 25(a)) and the average measured reflectance from adenocarcinoma (dashed line in FIG. 25(b)). This result agrees with the observation at histopathology that adenocarcinoma is characterized by increased extracellular collagen and enlarged cell nuclei.

Sites at which there was a significant degree of difference between the two reflectance measurements $R_1(\lambda)$ and $R_2(\lambda)$ were identified by using the manually-selected criterion $\Sigma|R_2(\lambda)-R_1(\lambda)|>4.25$. Here, $\Sigma$ denotes a sum over all wavelengths between 400 nm and 700 nm (the same range over which the PTI model was fit to each reflectance spectrum). Using these criteria, 26 of the 42 sites exhibited significant variation between the two measured reflectance spectra (attributed to variations in the amount of blood during the time-course of the experiment). For the other 16 sites, there was no significant variation between the two reflectance measurements (illustrating the capability of the instrumentation and experimental protocol to provide consistent measurements).

The PTI model was fit to each of the two reflectance spectra acquired from all 42 sites. In the fitting procedure, the value of the nuclear enlargement factor $L/L_o$ was varied from 1.0 to 1.5 (in steps of 0.1). The total hemoglobin concentration $[Hb]_{tot}$ was varied over an expanded range (from 1 μM to 401 μM, in steps of 5 μM) to better account for the blood content of the tissue. For each measurement, the best fit of the PTI model to the data was defined to be the fit that minimized the cost function $C_R=\Sigma|R_{measured}(\lambda)-R_{PTI}(\lambda)|$, where $R_{measured}(\lambda)$ was the measured reflectance spectrum, $R_{PTI}(\lambda)$ was the PTI reflectance model, and $\Sigma$ represented a sum over all wavelengths from 400-700 nm. For each site, the values of $L/L_o$ and $[Hb]_{tot}$ extracted from the best fits were compared for the two measurements. The parameter $L/L_o$ was used in this analysis because changes in $L/L_o$ have previously been shown to distinguish the adenocarcinoma spectra from the normal and chronic pancreatitis spectra.

Figure 26:
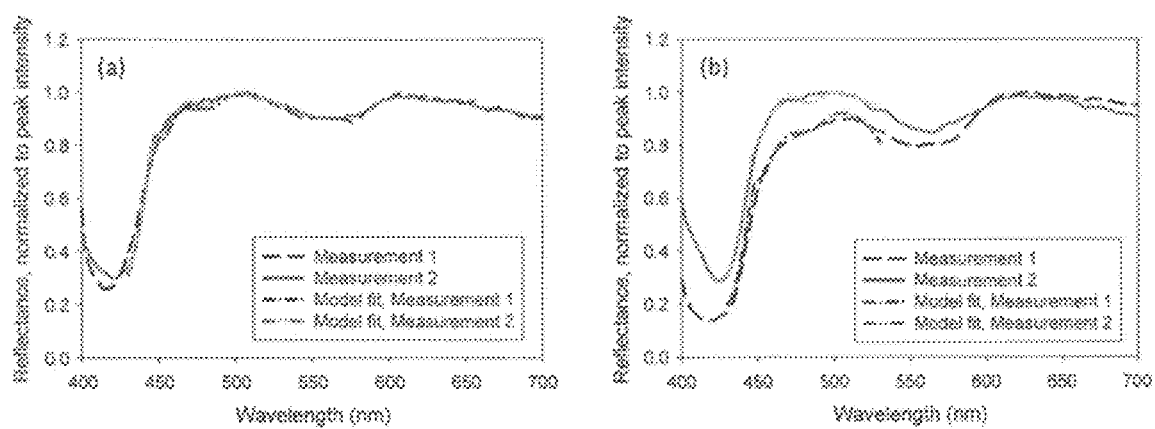
FIG. 26 provides fits of the PTI reflectance model from 430-500 nm for multiple measurements acquired from two different pancreatic tissue sites: one site from which the two measurements were very similar, and one site from which the two measurements were notably different.

FIG. 26(a) shows two measured reflectance spectra from a single adenocarcinoma site, along with the corresponding fits of the PTI model to each spectrum. According to the criterion described in, the two measurements shown in FIG. 26(a) were not considered to be significantly different. As expected, the extracted values of the nuclear enlargement factor $L/L_o$ and the mean reduced scattering coefficient $<\mu_s'>$ were identical for the two measurements. FIG. 26(b) shows two measured reflectance spectra from a second adenocarcinoma site, along with the corresponding fits of the PTI model to each spectrum. Here, according to the criterion described in, the two measurements were considered to be significantly different. However, the extracted values of the nuclear enlargement factor $L/L_o$ and the mean reduced scattering coefficient $<\mu_s'>$ were still identical for the two measurements. These results demonstrate the ability of the PTI model to extract consistent values of the tissue scattering properties even when there are noticeable variations in the amount of blood at a given site.

Figure 27:
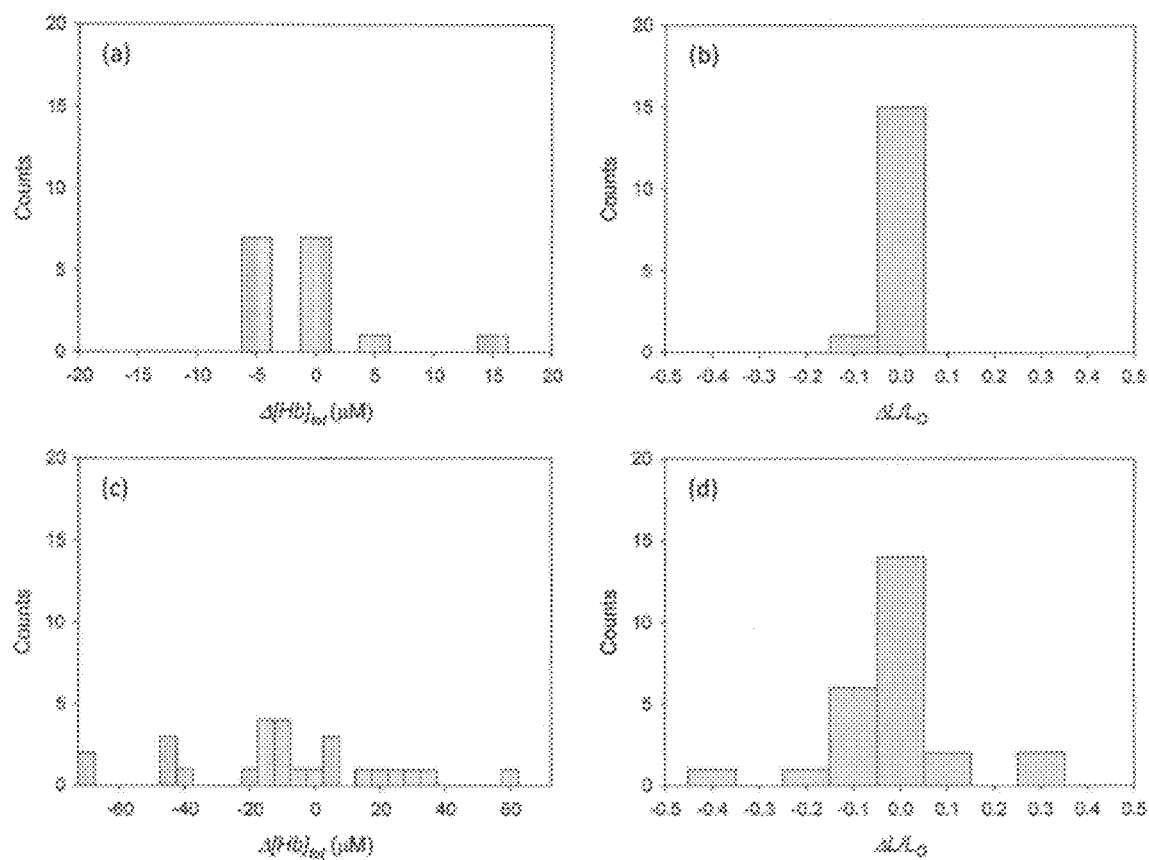
FIG. 27 provides histograms of differences in total hemoglobin concentration and mean cellular nuclear size from sites at which the two measured reflectance spectra were very similar and from sites at which the two reflectance measurements were notably different.

FIG. 27(a) shows a histogram of the differences between the total hemoglobin concentration values $[Hb]_{tot}$ acquired at the sites (N=16) for which there was no significant difference between the two measured spectra (including the site shown in FIG. 26(a)) according to the criterion described in. FIG. 27(b) shows the corresponding histogram of the differences between the $L/L_o$ values extracted from the two reflectance spectra extracted from each of these sites. The differences $\Delta[Hb]_{tot}$ and $\Delta L/L_o$ were defined as $[Hb]_{tot2}-[Hb]_{tot1}$ and $(L/L_o)_2-(L/L_o)_1$, respectively, where the subscripts 1 and 2 denoted the first and second measurements taken from a given site. For 15 of these 16 sites (94%), the $[Hb]_{tot}$ values extracted from the two measurements differed by less than 10 μM. Furthermore, for this set of 16 sites, the average difference between the $L/L_o$ values extracted from the two measurements was less than 1%. FIG. 27(b) shows that for 15 of these 16 sites, the $L/L_o$ values extracted from the two measurements were identical. In addition, the average difference between the $<\mu_s'>$ values extracted from the two measurements was less than 1%. These results demonstrate the robustness of the data collection method and the stability of the PTI model. FIG. 27(c) shows a histogram of the differences between the $[Hb]_{tot}$ values extracted from the two reflectance spectra acquired at the sites (N=26) for which there were significant differences between the two measured spectra (including the site shown in FIG. 26(b)) according to the criterion described in. FIG. 27(d) shows the corresponding histogram of the differences between the $L/L_o$ values extracted from each of these sites. For 21 of these 26 sites (81%), the $[Hb]_{tot}$ values from the two measurements differed by at least 10 μM. However, the average difference between the $L/L_o$ values extracted from the two measurements was less than 7%. FIG. 27(d) shows that for 22 of these 26 sites (85%), the magnitude of $\Delta L/L_o$ was no greater than 0.1 (the step size for $L/L_o$ in the PTI fitting procedure described in). In addition, the average difference between the $<\mu_s'>$ values extracted from the two measurements was less than 8%. These results indicate that the PTI model extracted consistent values of the tissue scattering properties even when the tissue blood content was varying.

For each tissue type, the five sites for which the two reflectance measurements were the most different from each other were determined by maximizing the function $\text{Diff}(R_1(\lambda), R_2(\lambda)) = \Sigma R_2(\lambda) - R_1(\lambda))$, where $R_1(\lambda)$ and $R_2(\lambda)$ were the two reflectance spectra measured from each site and $\Sigma$ represented a sum over the wavelengths from 400-700 nm. For this reduced data set, the mean $L/L_o$ value for adenocarcinoma ($L/L_o=1.28$) was still 22% larger than that of normal pancreatic tissue ($L/L_o=1.05$) and 20% larger than that of chronic pancreatitis ($L/L_o=1.07$). Using Wilcoxon rank-sum tests, the p-values for using $L/L_o$ to distinguish adenocarcinoma from normal tissue ($p<2\times10^{-3}$) and to distinguish adenocarcinoma from chronic pancreatitis ($p<7\times10^{-3}$) were still statistically significant for this reduced data set. These results suggest that the PTI algorithm has the potential to distinguish between different pancreatic tissue types even for sites with notable variations in blood content.

Figure 28:
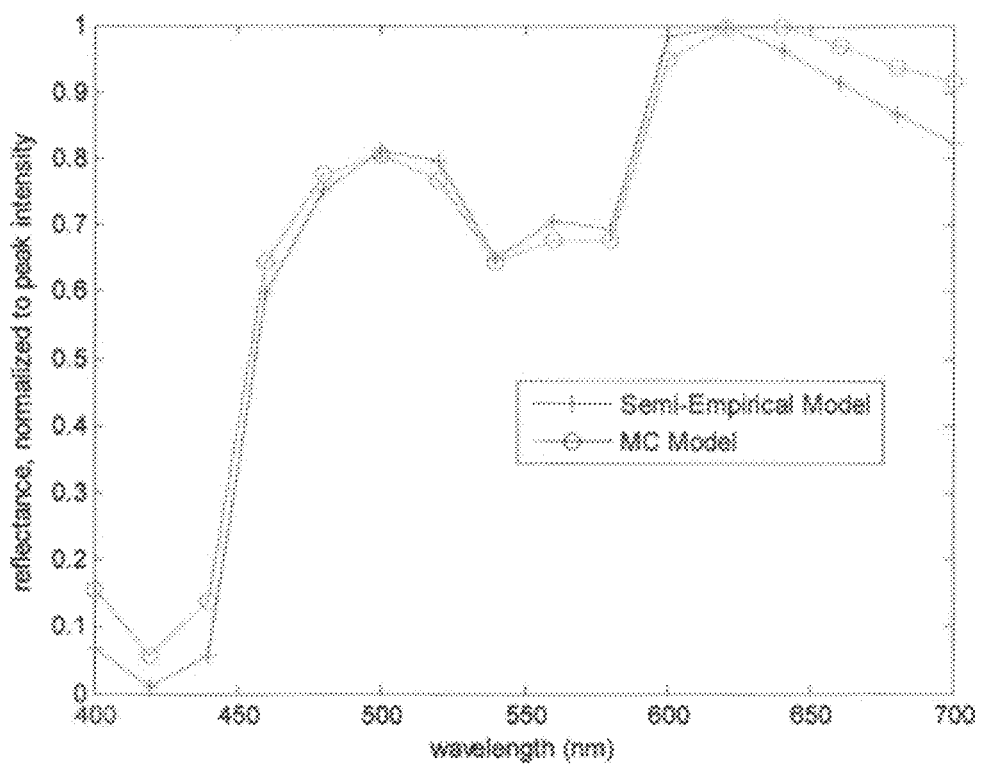
FIG. 28 provides the fit of the semi-empirical reflectance equation to Monte Carlo simulated reflectance for a computational verification of the semi-empirical equation.

A computational verification of the Photon-Tissue Interaction (PTI) reflectance model was also performed by using the semi-empirical reflectance model to fit the reflectance generated by a Monte Carlo (MC) code. A set of Monte Carlo (MC) simulations were run for tissue models with different absorption and scattering coefficients indicative of those of human pancreatic tissue at wavelengths interrogated by the clinically-compatible optical instrumentation. The absorption coefficient was calculated as a linear concentration of the molar extinction coefficients of oxy- and deoxy-hemoglobin. The oxy- and deoxy-hemoglobin concentrations were both set to 10 μM, a value within the range pertinent to the human pancreatic tissue measurements. The scattering coefficient was calculated by using the Van de Hulst approximation to Mie theory for spherical scatterers of mean diameter 9 μm, refractive index 1.41, and concentration $7\times10^7$ cm$^{-3}$ (values that were also pertinent to the human pancreatic tissue measurements). The surrounding medium was assumed to have refractive index of 1.33 (equal to that of water) and the tissue was modeled to have an overall anisotropy of 0.7. Using the above parameters, the absorption and scattering coefficients were calculated for 16 wavelengths between 400 nm to 700 nm (in evenly-spaced steps of 20 nm). Then, a MC reflectance simulation was run for each of these 16 pairs of absorption and scattering coefficients, using the fiber-probe geometry from the optical instrument employed to measure human pancreatic tissues. The simulated reflectance was compared with that predicted by the semi-empirical reflectance model for various values of the fit coefficients b and c, which are calibration parameters related to tissue and probe properties. When the same absorption and scattering parameters were used in the semi-empirical equation as were used in the MC simulations, the semi-empirical equation was fit to the MC-generated data with a mean percent error in fit of less than 16% for b=0.3 and c=0.05 (FIG. 28). The mean percent error in fit was less than 4% in the 460-540 nm range where increased amplitude has been observed in measured pancreatic cancer reflectance (relative to normal pancreatic tissue and pancreatitis).

4. Conclusions

The photon-tissue interaction (PTI) model for extracting biophysically-relevant tissue absorption and scattering parameters from measured reflectance spectra uses semi-empirical equations to scale an average measured "canonical normal" reflectance spectrum such that disease-related changes in the reflectance spectra are quantitatively linked to parameters related to tissue structure (such as mean size of cell nuclei and concentration of collagen fibers). The effect of the different tissue properties on the semi-empirical reflectance equations was systematically examined, and the semi-empirical equation was verified against a computational Monte Carlo code. In addition, the potential of optical spectroscopy to provide consistent values of tissue scattering parameters at a given tissue site, even when the measured spectra at that site are varying noticeably in time due to changes in absorption from blood, has been demonstrated. These results illustrate the feasibility of employing optical spectroscopy for consistent characterization of disease-related changes in human pancreatic tissues, among other things, and these findings should also be applicable to a wide range of other tissue types.

Illustration XI

1. Introduction

Clinically-compatible instrumentation such as those described herein was employed in the operating room to acquire reflectance and fluorescence spectra from freshly-excised human pancreatic tissues from 18 patients. Optical measurements were taken at multiple tissue sites from each patient using a customized fiber-optic probe and followed by biopsy at each site and histopathology. Care was taken to ensure the biopsy was done at the same site as where the optical measurement was made. In all, 39 normal sites, 34 pancreatitis sites, and 32 adenocarcinoma sites were evaluated. Differences among the tissue types were observed in both the reflectance and the fluorescence spectra. To quantitatively characterize these differences, two mathematical models were employed: a standard Principal Component Analysis (PCA) model and a newly-developed Photon-Tissue Interaction (PTI) model as described herein. Variables extracted from each of these models were then input into a statistically rigorous tissue classification algorithm that employed Generalized Estimating Equations (GEE) to account for the fact that measurements were obtained at multiple sites from each tissue specimen.

2. Methods

To acquire optical spectra from human pancreatic tissues, prototype clinically-compatible instrumentation as described herein in accordance with some embodiments of the invention was employed. The instrumentation included two light sources: a continuous-wave tungsten-halogen lamp (HL 2000FHSA, Ocean Optics, Dunedin, Fla.) for reflectance and a 355 nm laser (PNV001525-140, JDS Uniphase, San Jose, Calif.) to excite tissue fluorescence. To deliver light to and collect light from the tissue surface, a custom fiber-optic probe (Ocean Optics) was employed. The probe contained three fibers, each with diameter 660 □m, arranged in a triangular configuration as discussed herein. One fiber delivered light from the lamp to the tissue, the second fiber delivered laser light to the tissue, and the third fiber collected light that returned to the tissue surface. The collected light was sent to a spectrograph (MS 125, Oriel Instruments, Stratford, Conn.) and an intensified charge-coupled device (ICCD 2063, Andor Technology, Belfast, Northern Ireland) for wavelength-resolved detection. The reflectance and fluorescence measurements were performed sequentially.

Reflectance and fluorescence spectra were acquired from freshly-excised human pancreatic tissues within 30 minutes of excision. Multiple sites from each tissue specimen were measured, and two reflectance and two fluorescence measurements were acquired from each site (with the exception of one site, from which only one of each measurement was taken). After the optical measurements were acquired at a given site, the fiber-optic probe was kept in position at that site to mark the location of the site until the pathologist was ready to perform a biopsy of the site, and the biopsy was obtained by the pathologist immediately after the probe was removed. Biopsies were 3-5 mm in diameter, comparable to the ~1 mm-diameter region of tissue interrogated by the fiber-optic probe. These biopsies were subsequently fixed in formalin, paraffin-embedded, sectioned, stained with hematoxylin and eosin for histologic examination, and analyzed via histopathology.

Reflectance spectra for which the detected signal at 550 nm divided by the detected signal at 650 nm ($R_{550}/R_{650}$) was less than 0.2 were removed from the data set because these spectra were dominated by absorption from blood. It is important to note that the presence of blood is not considered problematic in tissue-optics studies because blood can be avoided by repositioning the tip of the probe, removed by suctioning the region of interest, or accounted for mathematically with the PTI model. Fluorescence spectra with a signal-to-noise ratio (SNR) of less than 30 were also removed, because these spectra were considered too noisy to properly analyze. Prior to data analysis, all raw spectra were background-corrected, corrected for instrument response, smoothed, and normalized to peak intensity.

A residual-based method was employed to detect and remove outlier sites for which the two measured fluorescence or reflectance spectra were extremely different from each other. This was done through a series of linear mixed models where the spectrum measurements at specific wavelengths were regressed on the tissue diagnosis with a random intercept to account for correlation among sites that originated from the same patient. Ten regressions were performed on the fluorescence spectra at wavelengths of 375.18, 417.19, 423.38, 427.52, 444.04, 452.99, 466.08, 479.16, 502.57, and 511.52 nm, and ten regressions were also performed on the reflectance spectra at wavelengths of 426.827, 440.598, 461.255, 481.913, 490.175, 541.130, 544.573, 612.053, 625.135, and 755.964 nm. Transformations were necessary to ensure that the spectral measurements had the Gaussian shape necessary for the linear regressions. For each of the regressions, the difference between the residuals of the two duplicate measurements at each site were calculated and ranked in order of magnitude. The ranks for the ten regressions were then averaged to give an overall fluorescence or reflectance average rank for each site. Sites whose overall mean rank exceeded the $85^{th}$ percentile of the total number of sites were flagged as potential outliers. Through this method five sites were identified as having a pair of very different reflectance spectra, and four additional sites were identified as having a pair of very different fluorescence spectra. Each site with two extremely different measurements was removed from the analysis (unless one of those two measurements had been removed from the data set previously due to low $R_{550}/R_{650}$ value or low fluorescence SNR), and for the remaining sites, the two measured spectra were averaged. The resulting spectral data from each site is referred to as the "measured data" in this Report. Of the 117 sites from which measurements were acquired, a total of 12 sites were removed from the data set due to low $R_{550}/R_{650}$ value, low fluorescence SNR, or high degree of difference between the two reflectance or fluorescence measurements.

The PCA code was written in MATLAB using functions that were built into the MATLAB programming language. The inputs to the PCA code were the measured reflectance and fluorescence spectra, without any prior correction of the spectra for attenuation artifacts. The PTI model was written in MATLAB employing a combination of equation to describe the measured reflectance and fluorescence data as functions of tissue properties related to absorption, scattering, and concentration of endogenous tissue fluorophores. In the PTI reflectance model, changes in the measured reflectance spectra were quantified by variations in the mean cellular nuclear diameter, hemoglobin concentration, and blood oxygenation. In the PTI fluorescence model, the measured fluorescence was first corrected for tissue absorption and scattering, and the resulting "intrinsic" fluorescence was then modeled as a linear combination of fluorescence emission spectra from collagen, NADH, and FAD.

Selection of the variables used in the tissue classification algorithm was determined through multinomial logistic regression using Generalized Estimating Equations (GEE) to statistically account for the intra-patient correlations in the data arising from the fact that the data set included multiple tissue sites from each patient. GEE has been previously employed in medical physics studies to correct for intra-patient correlations, for instance, in ophthalmology, in which there are correlations between data taken from each of the two eyes of a single patient.

Specifically, for each variable extracted by the PCA and PTI models, a GEE model with an exchangeable correlation structure was employed to contrast the differences between the mean values of that variable for each pair of tissue types. For each contrast, a Wald test statistic using the robust covariance matrix was calculated to account for the repeatedly measured observations from the same patients.

Following the identification of significant predictor variables, correlations between the selected variables were calculated and highly correlated variables were removed to minimize the multicollinearity. The variables used in the algorithm that included reflectance and fluorescence were the nuclear enlargement factor $L/L_o$ and percent collagen contribution % Collagen from the PTI model algorithm, the scores of the first three reflectance principal components (RPC1, RPC2, RPC3), and the score of the third fluorescence principal component (FPC3). The scores of the first two fluorescence principal components (FPC1, FPC2) were dropped due to their extreme correlation with other variables. The Pearson correlation between the first principal component of fluorescence and the percent collagen contribution was −0.92, and the Pearson correlation between the second principal component of fluorescence and the second principal component of reflectance was 0.76. The third fluorescence principal component FPC3 was used in the classification algorithm despite its lack of statistical significance because the cost associated with the multinomial logistic regression model was minimized when FPC3 was included.

For tissue classification, a "leave-two-patients-out" cross-validation method was employed. The classification algorithm was run nine times, and each time, the data set was split into a training set of 16 patients and a test set of two patients. The algorithm was executed nine times because there were 18 patients overall and each patient was put into the test set exactly once. For each pair of training and test data sets a standard multinomial logistic regression was fit to the training dataset, which is then used to generate optical diagnosis probabilities of adenocarcinoma, pancreatitis, and normal tissue types for the observations in the test data set. Thresholds were then applied to these probabilities to determine the sensitivity, specificity, positive predictive value, negative predictive value, and area under the ROC curve for distinguishing cancer sites from non-cancer (normal and chronic pancreatitis) sites.

Ternary plots of the optical diagnosis probabilities P(N), P(P), and P(A) were created for the hybrid algorithm using both PCA and PTI variables from both reflectance and fluorescence measurements (FIG. 29), the algorithm using only PCA variables (FIG. 30(a, c)) and the algorithm using only PTI variables (FIG. 30(b, d)). When the threshold on P(A) was varied to produce ROC curves for distinguishing cancer from non-cancer (normal and chronic pancreatitis) sites, the area under the ROC curve was 0.906 for the hybrid algorithm, 0.881 for the algorithm using only PCA variables, and 0.847 for the algorithm using only PTI variables (FIG. 31).

For the classification algorithm including reflectance and fluorescence variables, the thresholding method in which sites with P(A)>0.27 and P(N)<0.36 were diagnosed as cancer, was compared with a cost-function-based technique for calculating the optimal thresholds for determining a diagnosis of normal, chronic pancreatitis, or adenocarcinoma from the optical diagnosis probabilities (FIG. 30(c, d)). In cost-based classification techniques, penalties are assigned to each of the potential errors that can occur with prediction. For the cost function employed in this Illustration, incorrectly predicting a site as either chronic pancreatitis or normal tissue when it was actually adenocarcinoma was considered the worst possible error and assigned a high cost of 12. Predicting cancer for either normal or chronic pancreatitis sites resulted in a cost of 6. Finally, incorrectly predicting chronic pancreatitis as normal or vice versa was assigned a cost of 1. The optimal thresholds were those that minimized the total cost for the given model and were found through a grid search. The cost-based thresholding method distinguished adenocarcinoma from non-cancerous tissue with sensitivity, specificity, PPV, and NPV of 90.6%, 86.3%, 74.4%, and 95.5%, respectively, similar to those of the thresholding method in which sites with P(A)>0.27 were diagnosed as cancer (90.6%, 87.7%, 76.3%, and 95.5%, respectively).

Figure 31:
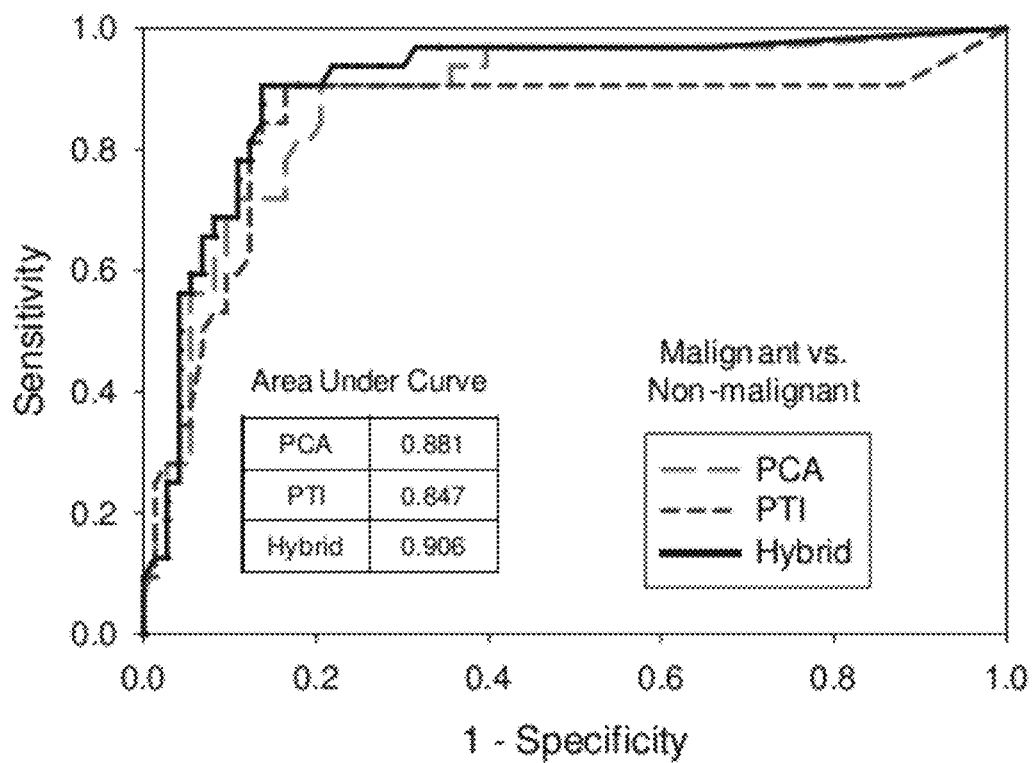
FIG. 31 provides ROC curves for distinguishing malignant from non-malignant (normal and pancreatitis) human pancreatic tissues, using parameters from the PCA model alone, parameters from the PTI model alone, and parameters from a hybrid model combining PCA and PTI results.
Figure 32B:
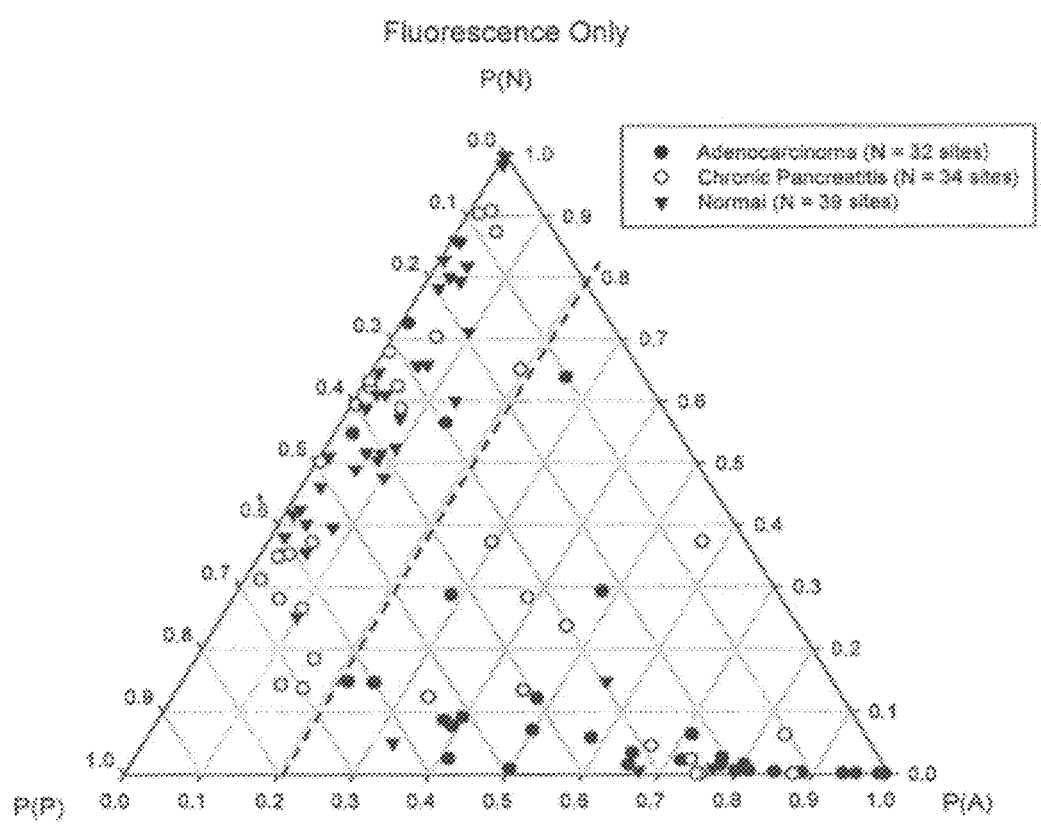
FIG. 32 provides ternary plots of optical diagnosis probabilities for distinguishing adenocarcinoma, pancreatitis, and normal pancreatic tissue, using (a) only parameters from reflectance, and (b) only parameters from fluorescence, with manually-selected thresholds on the probability of adenocarcinoma for optimal classification of malignant (adenocarcinoma) versus non-malignant (normal and pancreatitis) human pancreatic tissues.
Figure 33:
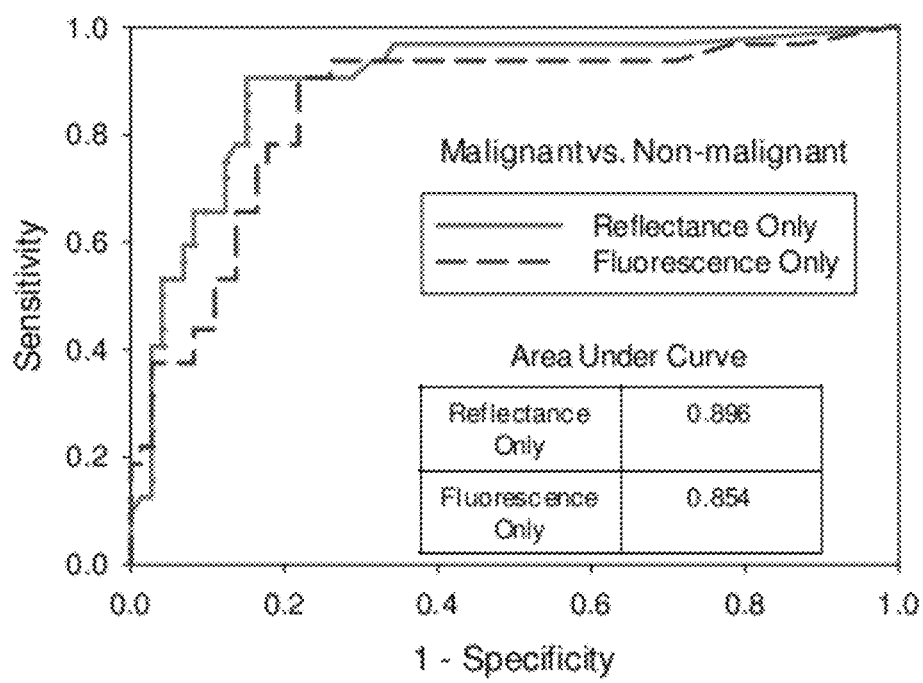
FIG. 33 provides ROC curves for distinguishing malignant from non-malignant (normal and pancreatitis) human pancreatic tissues, using parameters from reflectance alone and parameters from fluorescence alone.

Additional variations of the classification algorithm were run to compare the results obtained by using only reflectance variables (RPC1, RPC2, RPC3, L/L$_o$, [Hb]$_{tot}$) (FIG. 32(a), FIG. 33) and only fluorescence variables (FPC1, FPC2, FPC3) (FIG. 32(b), FIG. 33) with those obtained by using a combination of reflectance and fluorescence variables (RPC1, RPC2, RPC3, FPC3, L/L$_o$, % Collagen) (FIG. 29, FIG. 31). For these comparisons, thresholds were manually selected such that the resulting sensitivity was the same (90.6%) for all three algorithms, and then the corresponding specificity, PPV, and NPV of the three algorithms were compared. The PTI fluorescence variables (% Collagen, % NADH, % FAD) were not included in the classification algorithm that used only fluorescence data because the PTI model employed information from the reflectance to correct the measured fluorescence for attenuation artifacts before the resulting "intrinsic" fluorescence was fit with the PTI fluorescence equation.

Using only reflectance variables, and a manually-selected threshold of P(A)>0.19 for cancer diagnosis (FIG. 32(a)), the sensitivity, specificity, PPV, and NPV for distinguishing adenocarcinoma from non-cancerous tissues were 90.6%, 84.9%, 72.5%, and 95.4%. The area under the ROC curve was 0.896 when only reflectance variables were employed (FIG. 33). Using only fluorescence variables, and a manually-selected threshold of P(A)>0.21 for cancer diagnosis (FIG. 32(b)), the sensitivity, specificity, PPV, and NPV for distinguishing adenocarcinoma from non-cancerous tissues were 90.6%, 78.1%, 64.4%, and 95.0%. The area under the ROC curve was 0.854 when only fluorescence variables were employed (FIG. 33). For comparison, when reflectance and fluorescence variables were both included and the manually-selected threshold condition of (P(A)>0.27 and P(N)<0.36) was employed to diagnose adenocarcinoma sites, the sensitivity, specificity, PPV, and NPV for distinguishing adenocarcinoma from non-cancerous tissues were 90.6%, 87.7%, 76.3%, and 95.5% (FIG. 29), and the area under the ROC curve was 0.906 (FIG. 31) when reflectance and fluorescence were employed in tandem. A second threshold was not employed for the algorithms that used reflectance alone and fluorescence alone because adding this second threshold did not improve the cancer classification results in those cases. These results show that using a combination of reflectance and fluorescence provided improved classification of adenocarcinoma sites, relative to non-cancerous sites. However, the use of reflectance alone provided nearly the same cancer diagnostic accuracy as that of reflectance and fluorescence combined, a significant result since an optical device with only reflectance would be less expensive, more compact, and quicker when performing measurements.

In Vivo Optical Spectroscopic Embodiments

In this embodiment, in vivo optical spectroscopic measurements of human pancreatic tissues were conducted. The results demonstrated, among other things, the capability of the instrumentation as discussed herein to obtain in vivo optical data from three different data acquisition modalities: steady-state reflectance, steady-state fluorescence, and time-resolved fluorescence. In addition, the instrumentation of the invention was used to obtain in vivo and ex vivo data from the same tissue site, using the aforementioned data acquisition modalities. As a result, additional versions of the Photon-Tissue Interaction (PTI) model of steady-state reflectance and fluorescence have been developed and used to fit the in vivo data.

It has been found that the mean nuclear size parameter extracted by the PTI model from the reflectance (N=4 patients) was consistent (to within 2%) between the two in vivo measurements from a single site and the mean nuclear size parameter extracted by the PTI model from the reflectance (N=4 patients) was consistent (to within 5%) between the in vivo and ex vivo measurements from a single site. For the patient from which all three modalities of data were acquired in vivo and ex vivo, the mean fluorescence lifetime extracted from the time-resolved fluorescence was consistent (to within 3%) between the two in vivo measurements from a single site. For the patient from which all three modalities of data were acquired in vivo and ex vivo, the mean fluorescence lifetime extracted from the time-resolved fluorescence was consistent (to within 2%) between the in vivo and ex vivo measurements from a single site.

In vivo data collection procedures were developed to measure pancreatic tissues during Whipple surgical procedures. The probe descried herein for ex vivo measurements was redesigned to be suitable for the new procedure, including (i) sterilization and (ii) suitability for procedure.

With regard to sterilization, an Ethylene Oxide sterilization protocol was developed for probes designed as shown herein and developed in collaboration with FiberGuide Industries (Stirling, N.J.) with materials capable of undergoing at least 5 sterilization procedures with minimal optical loss. In addition to material changes, redesigns included lengthening the probe to a total length of 7 m. This additional length allows the probe to traverse from the non-sterile zone (location of instrument) into the sterile-zone (location of patient) for in vivo measurements.

Additionally, an in vivo measurement protocol was developed. Approximately ten minutes prior to in vivo measurement, the sterilized fiber-optic probe is opened onto the sterile field to the scrub nurse. Additionally, four angiocatheters are opened onto the sterile field, to mimic fiber-optic probe measurements as anticipated during endoscopic ultrasound-guided fine-needle aspiration measurement conditions, primarily mimicking the insertion of a fiber-optic probe tip through a needle-like delivery channel. Prior to measurements, the three proximal fiber legs (one for laser delivery, one for light delivery, and one for photon collection) are passed from the scrub nurse in the sterile zone to the experimentalist in the non-sterile zone to connect to the RFLS.

When the surgeon is ready to take measurements, an angiocatheter is inserted into a location of interest suspicious of pancreatic cancer. Duplicate measurements are taken at each site. For each surgery, at least two sites are measured at the surgeon's discretion. In order to replicate measurements ex vivo, ideally the surgeon will cut the angiocatheter flush to the tissue surface and differentiate the measurement sites with different length stitches. Alternatively, if the angiocatheters are at locations unsuitable to remain in the tissue specimen, entry sites are marked with different length stitches.

As during previous ex vivo data collection, a pathologist guides measurements to preserve sample integrity. At each measured in vivo site, the remaining angiocatheter is used to guide the fiber-optic probe to the tissue site or the pathologist uses an additional angiocatheter to penetrate the tissue at the approximate location of the in vivo measurement. After a duplicate measurement at each in vivo site, the pathologist resects a tissue specimen collocated to the distal fiber end as a 'gold standard' for optical measurements. When time permits, additional measurements are collected ex vivo for an expanded data set with the developed in vivo experimental procedures.

Figure 34:
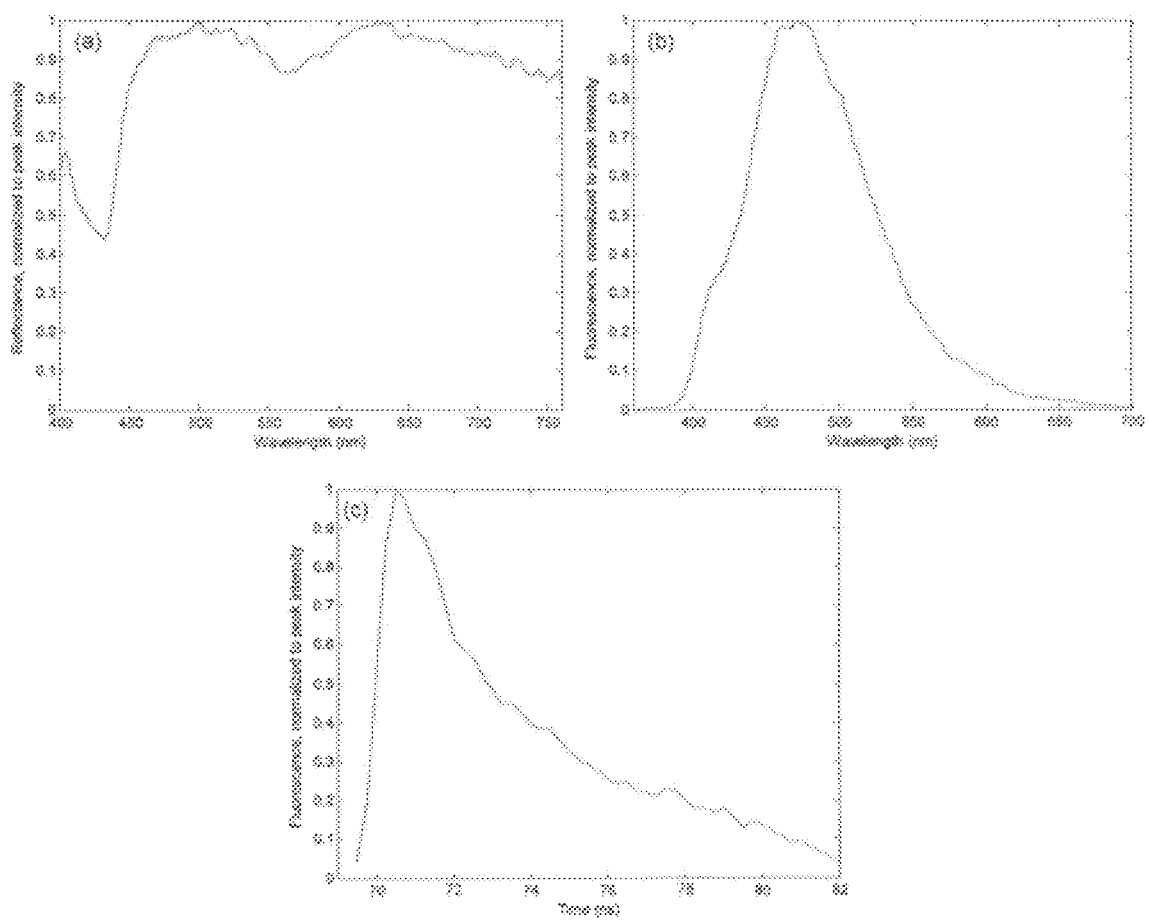
FIG. 34 provides graphs illustrating steady-state reflectance (a), steady-state fluorescence (b), and time-resolved fluorescence (c), acquired in vivo from a single human pancreatic tissue site.
Figure 35:
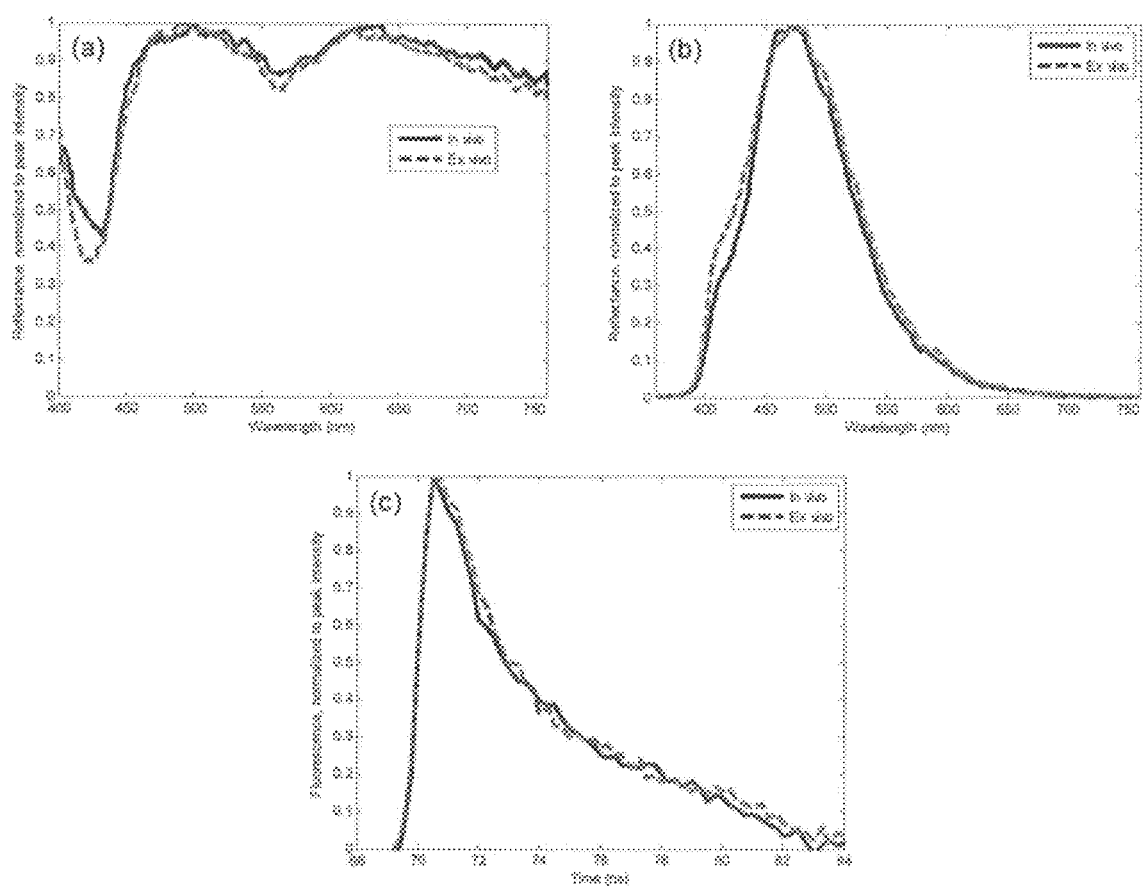
FIG. 35 provides graphs illustrating steady-state reflectance (a), steady-state fluorescence (b), and time-resolved fluorescence (c), acquired in vivo and ex vivo from a single human pancreatic tissue site. Visual inspection shows that the in vivo and ex vivo data share similar spectral and temporal features.

Using an updated data collection procedure (described below) with clinically-compatible instrumentation as described herein in accordance with some embodiments of the invention, steady-state reflectance (4 patients, 7 sites, 14 measurements), steady-state fluorescence (2 patients, 3 sites, 6 measurements), and time-resolved fluorescence (3 patients, 5 sites, 10 measurements) were acquired in vivo from human pancreatic tissues. For one patient (two sites), all three of these types of data were acquired in vivo and ex vivo. In vivo data of all three types, acquired at one of these sites, is shown in FIG. 34. A comparison of in vivo and ex vivo data from this site is shown in FIG. 35.

For this embodiment, the PTI model employed to analyze the steady-state reflectance and fluorescence data has been updated in one or more of the following primary ways:

(i) The model employs a direct fit of the semi-empirical reflectance equation to the data instead of scaling an average measured "canonical normal" spectrum.
(ii) The model includes packaging of blood into red blood cells and cylindrical blood vessels.
(iii) The model includes expanded ranges of oxy- and deoxy-hemoglobin concentrations that range from 2 µM to 2.048 mM, as defined by the formula $[Hb]=(1 \mu M)(2^k)$, where k is varied from 1-11 when the model is being fit to the data.
(iv) The model directly uses both the absorption and scattering coefficients extracted from the best fit of the reflectance model to correct the fluorescence for attenuation artifacts to obtain the intrinsic fluorescence.
(v) The model corrects the non-normalized fluorescence data for attenuation artifacts to obtain the intrinsic fluorescence.
(vi) The model fits the intrinsic fluorescence with a linear combination of basis spectra without blue-shifting the basis spectra.
(vii) In some embodiments, the model also includes varying absorption from beta-carotene, using pre-published beta-carotene absorption spectrum (which may be found at the website-http://omlc.ogi.edu/spectra/PhotochemCAD/html/beta-carotene.html)
(viii) In some embodiments, the model also varies the refractive indices of the cell nuclei and the surrounding medium.
(ix) In some embodiments, the model varies the mean blood vessel radius.
(x) In some embodiments, the features described in (ii) and/or (iii) are combined with other PTI models described herein to scale an average measured "canonical normal" reflectance spectrum to model the measured reflectance data.
(xi) In some embodiments, the model is fit to non-normalized reflectance data and the amplitude and shift in the semi-empirical equation are allowed to vary.

PTI Modeling of In Vivo Steady-State Reflectance Data

Figure 36:
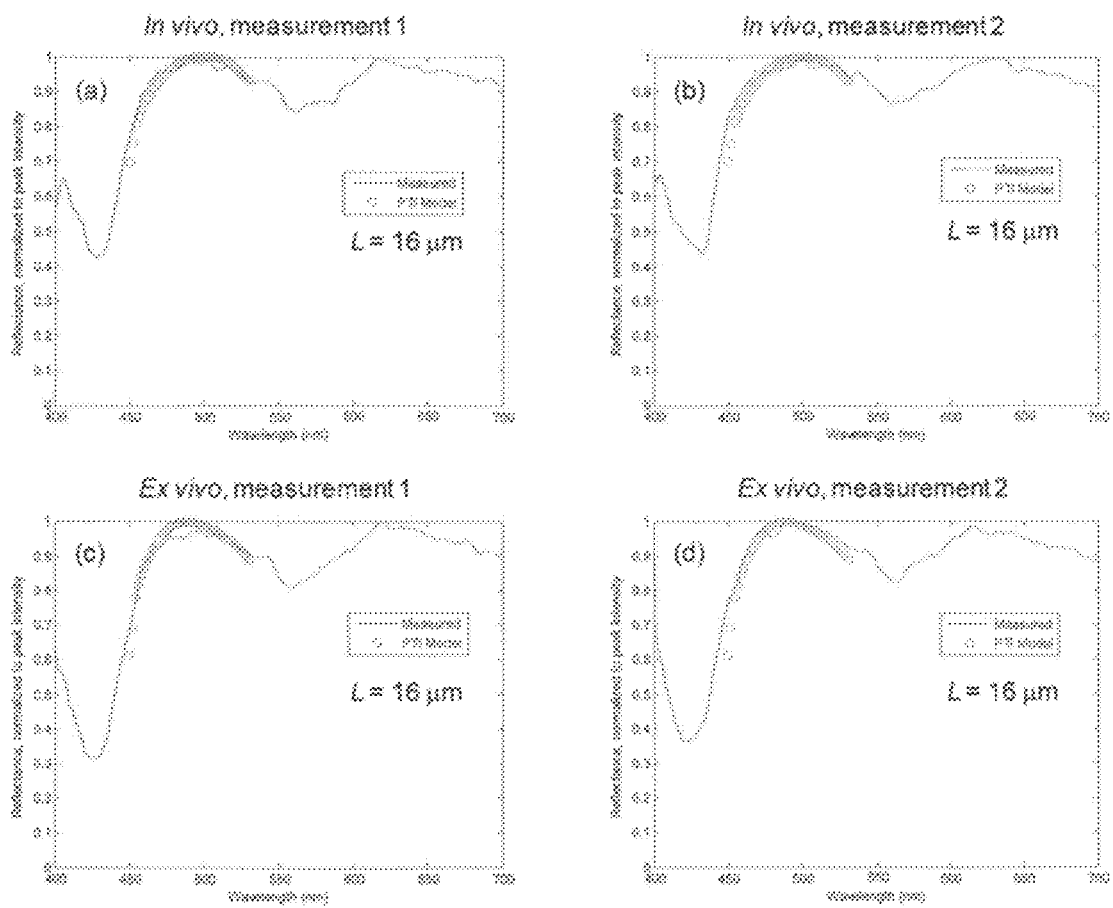
FIG. 36 provides graphs illustrating fits of the PTI model (from 450-530 nm) to two reflectance spectra measured in vivo at a human pancreatic tissue site, along with the PTI model fits to two reflectance spectra measured ex vivo at that site. The 450-530 nm wavelength range is emphasized because the spectral amplitude in that region is significantly affected by changes in scattering due to disease-related variations in parameters such as the mean diameter L of cell nuclei. For a data set of 7 sites from 4 patients, the extracted value of the mean nuclear diameter L was consistent (to within 2%) between the two in vivo measurements from a single site. For this same data set, the mean extracted value of L was also consistent (to within 5%) between the in vivo and ex vivo measurements from a single site.

The updated PTI model described above was employed to model the in vivo human pancreatic tissue steady-state reflectance data. Fits of the PTI reflectance model to the data from one tissue site, along with the extracted nuclear diameter L, are shown in FIG. 36. For the 7 sites (4 patients) from which reflectance spectra were obtained in vivo and ex vivo, the PTI model extracted the mean nuclear diameter L. For 6 of these 7 sites, the mean value of L extracted from the in vivo data was the same as that extracted for the ex vivo data. This result suggests that the optical instrumentation and the PTI model can provide the same diagnostic information in vivo as they have been previously shown to provide ex vivo in other embodiments herein.

Exponential Decay Modeling of In Vivo Time-Resolved Fluorescence Data

Figure 37:
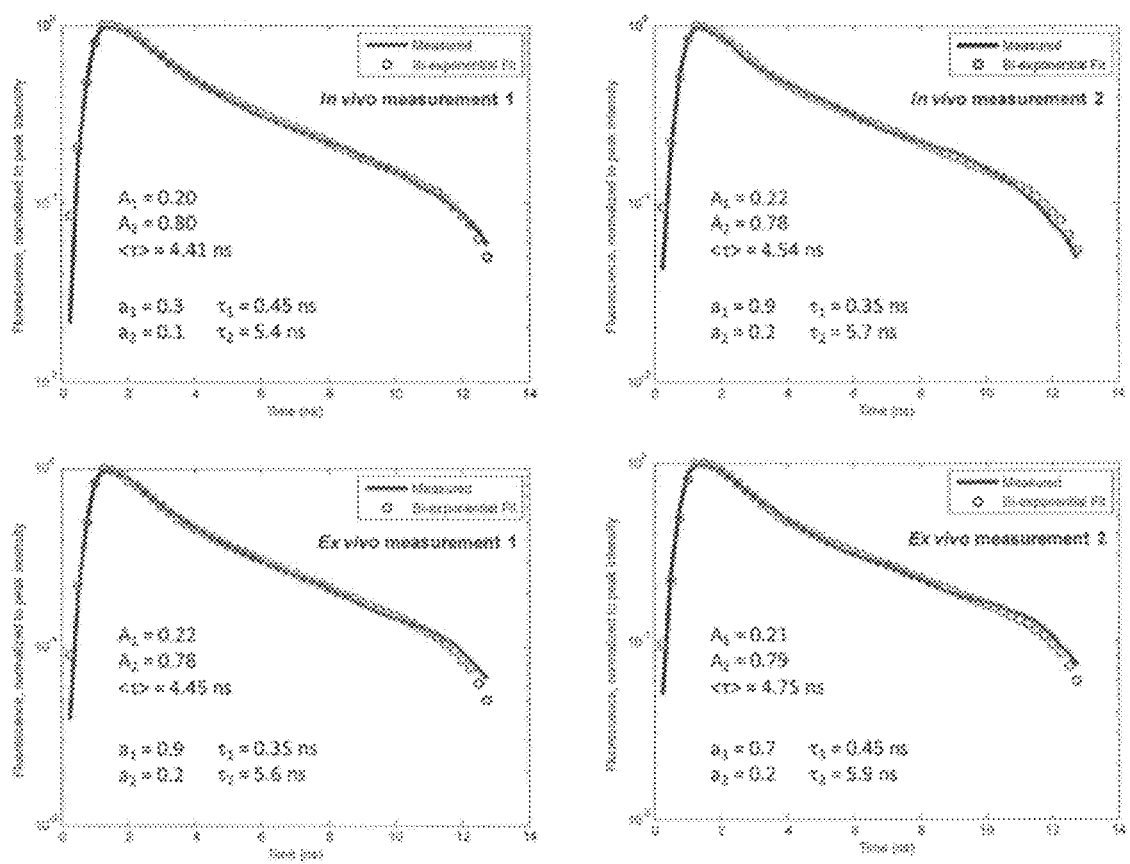
FIG. 37 provides graphs illustrating fits of a bi-exponential decay model to two time-resolved fluorescence decay curves measured in vivo at a human pancreatic tissue site, along with the model fits to two decay curves measured ex vivo at that site. For the patient from which all three types of data were acquired in vivo and ex vivo, the extracted mean lifetimes $<\tau>$ were consistent to within 3% between the two in vivo measurements from a single site and to within 2% between the in vivo and ex vivo measurements from a single site.

A bi-exponential decay equation was employed to model the in vivo human pancreatic tissue time-resolved fluorescence data. Fits of this model to the data from one tissue site and extracted parameters related to amplitude and lifetime are shown in FIG. 37 and Table 41, respectively.

TABLE 41

Mean lifetimes extracted in vivo and ex vivo from time-resolved fluorescence for the patient from which all three types of data were collected in vivo and ex vivo.

| Site | Measurement | Mean Lifetime, In Vivo (ns) | Mean Lifetime, Ex Vivo (ns) |
|---|---|---|---|
| 1 | 1 | 4.41 | 4.45 |
|   | 2 | 4.54 | 4.75 |
| 2 | 1 | 5.58 | 5.51 |
|   | 2 | 5.46 | 5.59 |

It should be understood that any of the methods described herein may be incorporated and provided through a system which includes one or more probe members in communication with a processing device, database, memory device, data input/output device and display device.

While exemplary systems and methods, and applications of methods of the invention, have been described herein, it should also be understood that the foregoing is only illustrative of a few particular embodiments with exemplary and/or preferred features, as well as principles of the invention, and that various modifications can be made by those skilled in the art without departing from the scope and spirit of the invention. Therefore, the described embodiments should not be considered as limiting of the scope of the invention in any way. Accordingly, the invention embraces alternatives, modifications and variations which fall within the spirit and scope of the invention as set forth in the claims and further include equivalents thereto.

What is claimed is:

1. A method of employing multimodal spectroscopy to classify pancreatic tissue in vivo comprising the steps of:

transforming reflectance and fluorescence spectra for normal pancreatic tissue by varying the concentration of collagen in the tissue, mean size of cell nuclei, or both, to develop a photon-tissue interaction model including simulations of the reflectance and fluorescence spectra for adenocarcinoma and pancreatitis;

illuminating pancreatic tissue having an unknown classification in vivo to produce a spectroscopic event from which steady-state reflectance, steady-state fluorescence, and time-resolved fluorescence signals may be obtained;

collecting spectroscopic response data from the spectroscopic event, wherein the response data includes measurements derived from steady-state reflectance, steady-state fluorescence, and time-resolved fluorescence signals associated with the tissue;

comparing the spectroscopic response data with the a photon-tissue interaction model for the reflectance and fluorescence spectra to extract tissue parameters from the measured data, wherein the tissue parameters include the concentration of collagen and mean size of cell nuclei in the illuminated pancreatic tissue, and a multi-exponential decay model of the time-resolved fluorescence in order to extract amplitudes and lifetimes from the measured data; and classifying the tissue as either normal, adenocarcinoma or pancreatitis based on the comparisons.

2. A method according to claim 1, wherein the step of illuminating the biological tissue sample is configured to produce a plurality of measurable spectroscopic events.

3. A method according to claim 2, wherein the illuminating step includes an event including illumination wavelengths of about 400 nm to about 750 nm to facilitate collecting reflectance signal measurements and an event including illumination wavelengths of about 355 nm to facilitate collecting fluorescence signal measurements.

4. A method according to claim 1, wherein the photon-tissue interaction model for the reflectance is modified to include a direct fit of the semi-empirical reflectance equation to the data instead of scaling an average measured canonical normal spectrum.

5. A method according to claim 1, wherein the photon-tissue interaction model for the reflectance is modified to consider the packaging of blood into red blood cells and cylindrical blood vessels.

6. A method according to claim 1, wherein the photon-tissue interaction model for the reflectance is modified to include expanded ranges of oxy- and deoxy-hemoglobin concentrations that range from about 2 μM to about 2.048 mM, as defined by the formula $[Hb]=(1\ \mu M)(2^k)$, where k is varied from 1-11 when the model is being fit to the data.

7. A method according to claim 1, wherein the photon-tissue interaction model for the fluorescence is modified such that the absorption and scattering coefficients extracted from the best fit of the reflectance model are both used to correct the fluorescence for attenuation artifacts to obtain the intrinsic fluorescence.

8. A method according to claim 1, wherein the photon-tissue interaction model for the fluorescence is modified such that the non-normalized fluorescence data is corrected for attenuation artifacts to obtain the intrinsic fluorescence.

9. A method according to claim 1, wherein the photon-tissue interaction model for the fluorescence is modified wherein the intrinsic fluorescence is fit with a linear combination of basis spectra without blue-shifting the basis spectra.

10. A method according to claim 1, wherein the photon-tissue interaction model for the reflectance is modified to consider varying absorption from beta-carotene, using a pre-published beta-carotene absorption spectrum.

11. A method according to claim 1, wherein the photon-tissue interaction model for the reflectance is modified to consider varying the refractive indices of the cell nuclei and the surrounding medium.

12. A method according to claim 1, wherein the photon-tissue interaction model for the reflectance is modified to consider varying the mean blood vessel radius.

13. A method according to claim 1, wherein the photon-tissue interaction model for the reflectance is modified to fit to non-normalized reflectance data and the amplitude and shift in the semi-empirical equation are allowed to vary.

* * * * *